(12) United States Patent
Zhang et al.

(10) Patent No.: US 11,117,123 B2
(45) Date of Patent: *Sep. 14, 2021

(54) COMPOSITIONS AND METHODS FOR CATALYSTS BASED ON BRIDGED CHIRAL AMIDOPORPHYRINS AND THEIR METAL COMPLEXES

(71) Applicant: Trustees of Boston College, Chestnut Hill, MA (US)

(72) Inventors: Xiao-Xiang Zhang, Newton, MA (US); Yang Hu, Hockesssin, DE (US)

(73) Assignee: The Trustees of Boston College, Chestnut Hill, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/851,041

(22) Filed: Apr. 16, 2020

(65) Prior Publication Data

US 2020/0330968 A1    Oct. 22, 2020

Related U.S. Application Data

(60) Provisional application No. 62/834,528, filed on Apr. 16, 2019.

(51) Int. Cl.
*B01J 31/18*      (2006.01)
*C07C 67/347*     (2006.01)
*C07D 203/24*     (2006.01)

(52) U.S. Cl.
CPC .......... *B01J 31/183* (2013.01); *C07C 67/347* (2013.01); *C07C 2601/02* (2017.05); *C07D 203/24* (2013.01)

(58) Field of Classification Search
None
See application file for complete search history.

(56) References Cited

U.S. PATENT DOCUMENTS

2012/0077990 A1* 3/2012 Zhang ............... C07D 203/24
                                                          548/961
2020/0317627 A1* 10/2020 Zhang ............... C07D 285/10

OTHER PUBLICATIONS

Hu et al. "Next-Generation D2-Symmetric Chiral Porphyrins for Cobalt(II)-Based MetalloradicalCatalysis: Catalyst EngineeringbyDistalBridging" Angewandte Chemie International Edition, 2019, vol. 58, pp. 2670-2674.*

Lang et al. "Asymmetric Induction and Enantiodivergence in Catalytic Radical C—H Amination via Enantiodifferentiative H-Atom Abstraction and Stereoretentive Radical Substitution" Journal of the American Chemical Society, 2019, vol. 141, pp. 12388-12396.*

Denney et al. "Formation of Cyclopropanes From Phosphoranes and Epoxides" Journal of the American Chemical Society, 1959, vol. 81, pp. 6330-6331.*

* cited by examiner

*Primary Examiner* — Joseph R Kosack
(74) *Attorney, Agent, or Firm* — Lei Fang; Smith Tempel Blaha LLC

(57) ABSTRACT

In one aspect, the disclosure relates to a mode of asymmetric induction in radical processes based on enhanced hydrogen-bonding capability and the situation of metal centers in cavity-like chiral environments. Also disclosed is an asymmetric system for stereoselective synthesis of cyclopropane and aziridine derivatives. The disclosed Co(II)-based metalloradical system has been shown to have an unusual capability of controlling both the degree and sense of asymmetric induction in cyclopropanation and aziridination reactions in a systematic manner. The disclosed system is applicable to a broad scope of substrates having diazo or azido moieties and exhibits a remarkable profile of reactivity and selectivity, providing access to cyclopropane diastereomers and aziridine enantiomers in highly enantioenriched forms. Also disclosed are catalysts useful in the disclosed processes. This abstract is intended as a scanning tool for purposes of searching in the particular art and is not intended to be limiting of the present disclosure.

16 Claims, 29 Drawing Sheets

COMPOSITIONS AND METHODS FOR CATALYSTS BASED ON BRIDGED CHIRAL AMIDOPORPHYRINS AND THEIR METAL COMPLEXES

CROSS-REFERENCE TO RELATED APPLICATIONS

This application claims the benefit of U.S. Provisional Application No. 62/834,528, filed on Apr. 16, 2019.

STATEMENT REGARDING FEDERALLY SPONSORED RESEARCH OR DEVELOPMENT

This invention was made with U.S. Government support under grant number GM102554 awarded by the National Institutes of Health and CHE-162416 awarded by the National Science Foundation. The U.S. government has certain rights in the invention.

FIELD OF INVENTION

The present disclosure is directed to new generation catalysts based on bridged chiral amidoporphyrins and their metal complexes; and reactions utilizing the catalysts to prepare chiral cyclopropane derivatives and chiral aziridine derivatives.

BACKGROUND

Homolytic radical chemistry has been increasingly explored for the development of alternative tools for bond-breaking and bond-forming that may shape the state of the art of organic synthesis. Despite significant advancements in this endeavor, general strategies for addressing the enduring issues of controlling reactivity and selectivity in radical reactions, particularly enantioselectivity, remain to be uncovered. Among recent developments, metalloradical catalysis (MRC), which explores the use of metalloradical complexes as open-shell catalysts for catalytically generating organic radical intermediates as well as controlling subsequent homolytic radical transformations, has emerged as a conceptually new approach. In this context, Co(II) complexes of porphyrins, as 15e stable metalloradicals, have exhibited unusual efficiency in radical activation of diazo compounds to generate the fundamentally new α-Co(III)-alkyl radicals A1 (FIG. 1A). The resulting Co-stabilized C-centered radical intermediates can undergo radical addition to alkenes for generation of α-Co(III)-alkyl radicals A2, which subsequently proceed intramolecular homolytic radical substitution (3-exo-tet radical cyclization) to produce cyclopropanes upon regeneration of Co(II)-based metalloradicals. The outcome of this Co(II)-based metalloradical catalysis (Co(II)-MRC) is the revelation of an unprecedented catalytic pathway for olefin cyclopropanation that operates via a stepwise radical mechanism (Scheme 1A). In parallel, the application of Co(II)-MRC with organic azides has resulted in the disclosure of a new radical pathway for catalytic olefin aziridination that involves α-Co(III)-aminyl radicals B1[8] and α-Co(III)-alkyl radicals B2 as key intermediates (FIG. 1B). Despite their underlying radical mechanisms, catalytic transformations via Co(II)-MRC can be rendered stereoselective because the radical intermediates involved are no longer "free" but controlled by the catalysts. In practice, the formidable challenge associated with controlling stereoselectivity of radical reactions can essentially be translated to a solvable problem of catalyst design and development.

Since first introduced, the family of $D_2$-symmetric chiral amidoporphyrins ($D_2$-Por*) have proved particularly effective in controlling reactivity as well as stereoselectivity of various radical transformations via Co(II)-MRC. In addition to the pocket-like chiral environment with tunable electronic and steric properties, the effectiveness of this family of ligands in supporting Co(II)-MRC is also attributed to the postulated H-bonding interactions between N—H units of the amides on the amidoporphyrin ligand as the HB-donors and the substituents on the C- or N-centered radical moiety as the HB-acceptors, as illustrated (FIG. 1C) with the common metalloradical catalyst [Co(P1)] (P1: 3,5-Di$^t$Bu-ChenPhyrin). While existing $D_2$-symmetric chiral amidoporphyrins have been successfully applied for a number of catalytic radical processes, the need to design the next generation of MRC catalysts with improved catalytic properties has become increasingly evident.

Ideally, a method for catalytic asymmetric radical cyclopropanation and aziridination reactions would be capable of controlling the degree and sense of asymmetric induction in a systematic manner, would be applicable to a broad scope of substrates having diazo or azido moieties, and would be reactive and selective in providing target compounds in a highly enantioenriched form. These needs and other needs are satisfied by the present disclosure.

SUMMARY

In accordance with the purpose(s) of the present disclosure, as embodied and broadly described herein, the disclosure, in one aspect, relates to a mode of asymmetric induction in radical processes that is based on enhanced hydrogen-bonding capability and situation of metal centers in cavity-like chiral environments. Also disclosed is an asymmetric system for stereoselective synthesis of cyclopropane and aziridine derivatives. The disclosed Co(II)-based metalloradical system has been shown to have an unusual capability of controlling both the degree and sense of asymmetric induction in the disclosed cyclopropanation and aziridination reactions in a systematic manner. The disclosed system is applicable to a broad scope of substrates having diazo or azido moieties and exhibits a remarkable profile of reactivity and selectivity, providing access to cyclopropane diastereomers and aziridine enantiomers in highly enantioenriched forms. Also disclosed are catalysts useful in the disclosed processes.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims. In addition, all optional and preferred features and modifications of the described embodiments are usable in all aspects of the disclosure taught herein. Furthermore, the individual features of the dependent claims, as well as all optional and preferred features and modifications of the described embodiments are combinable and interchangeable with one another.

BRIEF DESCRIPTION OF THE DRAWINGS

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIG. 1 shows radical pathways for cyclopropanation and aziridination as described in the present disclosure.

FIGS. 4A-4B show, respectively, spectra for P1 and P2, or open (unbridged) amidoporphyrins, while FIGS. 4C-4D show, respectively, spectra for porphyrins P3 ($C_4$ bridged) and $P_4$ ($C_6$ bridged).

FIG. 10 shows cavity-size approximations for chiral bridged-amidoporphyrins of the present disclosure.

FIGS. 13A and 13B show, respectively, $^1$H and $^{13}$C NMR spectra for compound 4a.

FIG. 17 shows characterization data for the reaction to produce chiral compound 5.

FIG. 18 shows characterization data for the reaction to produce chiral compound 6.

Figures 1A, 1B:
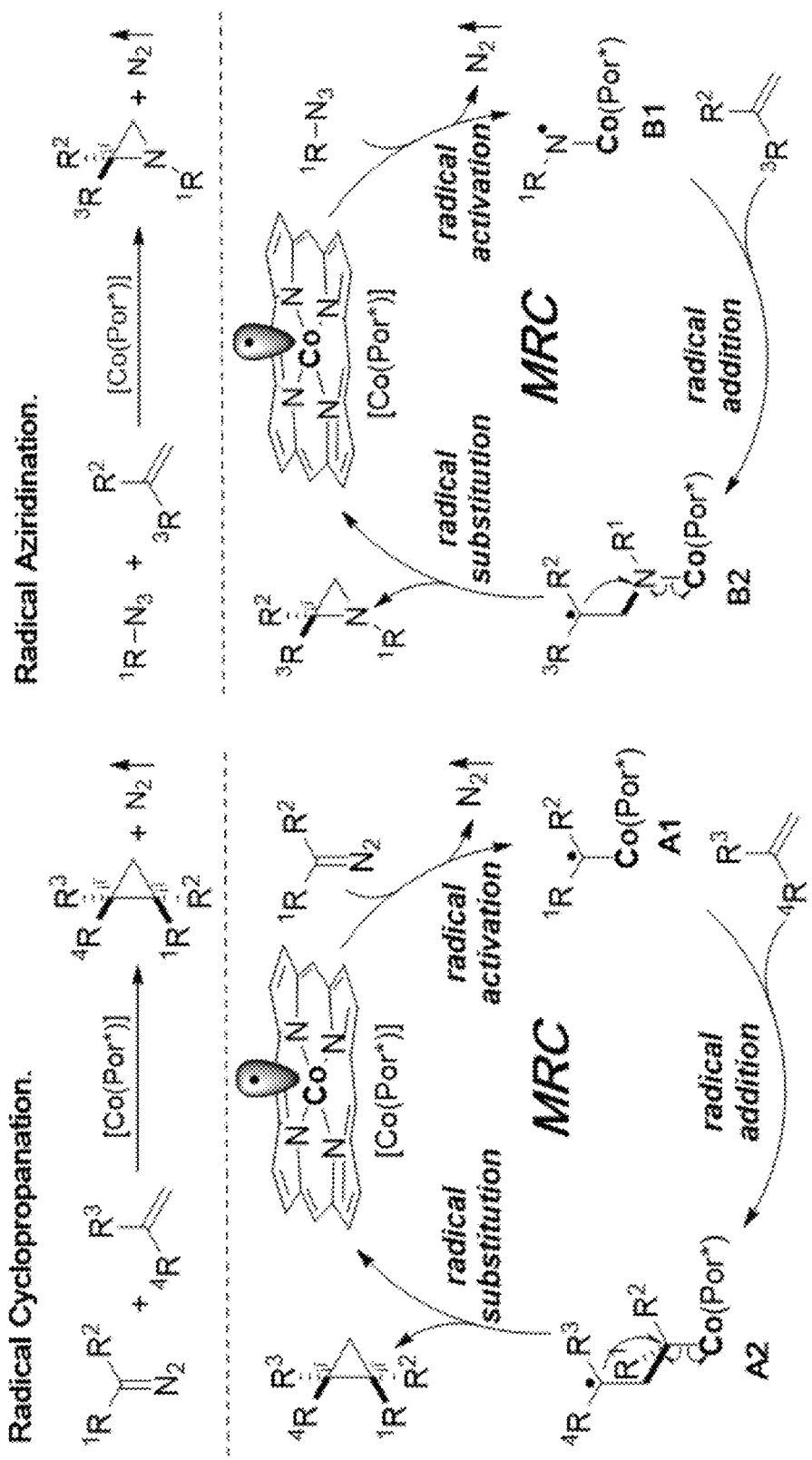
FIG. 1A shows radical cyclopropanation.
FIG. 1B shows radical aziridination.
Figure 1C:
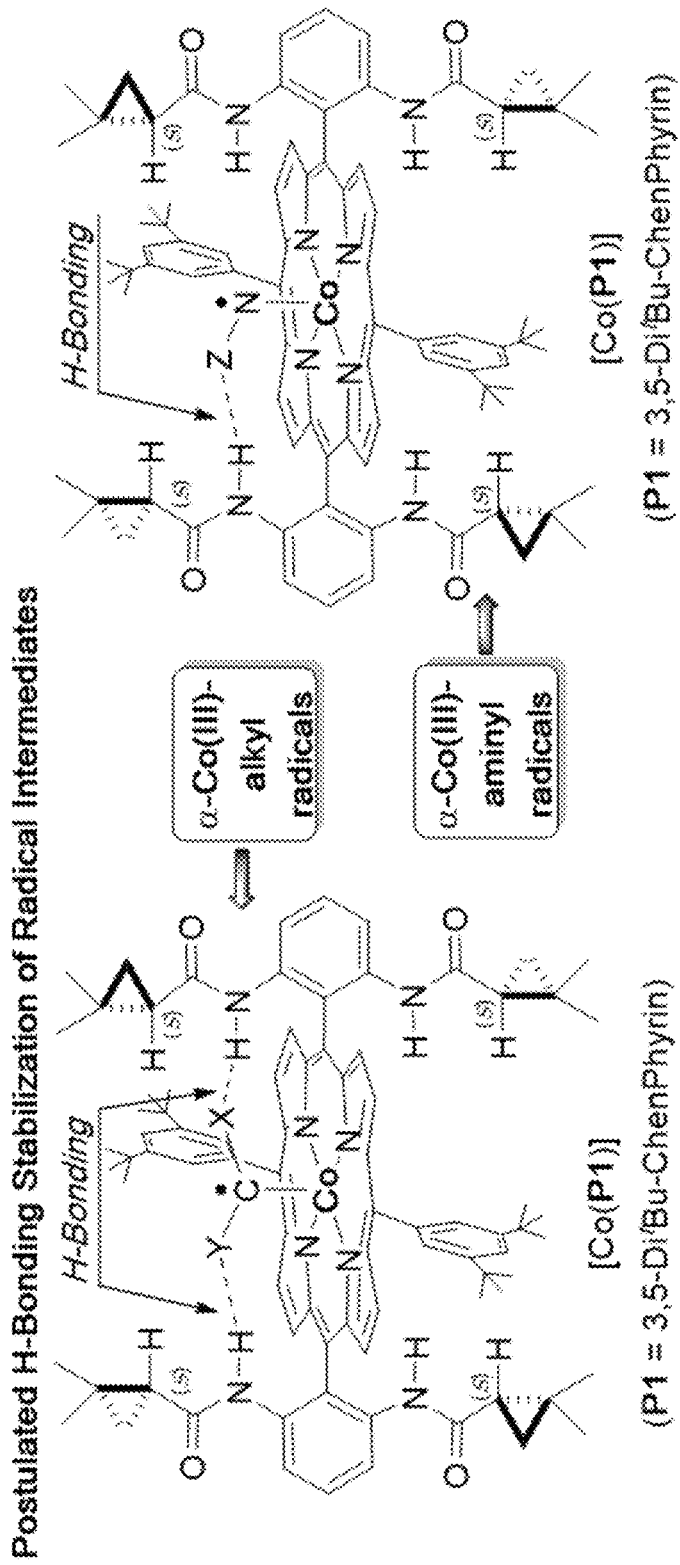
FIG. 1C shows postulated H-bonding stabilization of radical intermediates.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

Many modifications and other embodiments disclosed herein will come to mind to one skilled in the art to which the disclosed compositions and methods pertain having the benefit of the teachings presented in the foregoing descriptions and the associated drawings. Therefore, it is to be understood that the disclosures are not to be limited to the specific embodiments disclosed and that modifications and other embodiments are intended to be included within the scope of the appended claims. The skilled artisan will recognize many variants and adaptations of the aspects described herein. These variants and adaptations are intended to be included in the teachings of this disclosure and to be encompassed by the claims herein.

Although specific terms are employed herein, they are used in a generic and descriptive sense only and not for purposes of limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure.

Any recited method can be carried out in the order of events recited or in any other order that is logically possible. That is, unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

While aspects of the present disclosure can be described and claimed in a particular statutory class, such as the system statutory class, this is for convenience only and one of skill in the art will understand that each aspect of the present disclosure can be described and claimed in any statutory class.

It is also to be understood that the terminology used herein is for the purpose of describing particular aspects only and is not intended to be limiting. Unless defined otherwise, all technical and scientific terms used herein have the same meaning as commonly understood by one of ordinary skill in the art to which the disclosed compositions and methods belong. It will be further understood that terms, such as those defined in commonly used dictionaries, should be interpreted as having a meaning that is consistent with their meaning in the context of the specification and relevant art and should not be interpreted in an idealized or overly formal sense unless expressly defined herein.

Prior to describing the various aspects of the present disclosure, the following definitions are provided and should be used unless otherwise indicated. Additional terms may be defined elsewhere in the present disclosure.

Definitions

As used herein, "comprising" is to be interpreted as specifying the presence of the stated features, integers, steps, or components as referred to, but does not preclude the presence or addition of one or more features, integers, steps, or components, or groups thereof. Moreover, each of the terms "by", "comprising," "comprises", "comprised of," "including," "includes," "included," "involving," "involves," "involved," and "such as" are used in their open, non-limiting sense and may be used interchangeably. Further, the term "comprising" is intended to include examples and aspects encompassed by the terms "consisting essentially of" and "consisting of." Similarly, the term "consisting essentially of" is intended to include examples encompassed by the term "consisting of.

As used in the specification and the appended claims, the singular forms "a," "an" and "the" include plural referents unless the context clearly dictates otherwise. Thus, for example, reference to "a cyclopropane derivative," "a catalyst," or "a stereocenter," includes, but is not limited to, mixtures or combinations of two or more such cyclopropane derivatives, catalysts, or stereocenters, and the like.

It should be noted that ratios, concentrations, amounts, and other numerical data can be expressed herein in a range format. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. Ranges can be expressed herein as from "about" one particular value, and/or to "about" another particular value. Similarly, when values are expressed as approximations, by use of the antecedent "about," it will be understood that the particular value forms a further aspect. For example, if the value "about 10" is disclosed, then "10" is also disclosed.

When a range is expressed, a further aspect includes from the one particular value and/or to the other particular value. For example, where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In addition, the phrase "about 'x' to 'y'", where 'x' and 'y' are numerical values, includes "about 'x' to about 'y'".

It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to 5%" should be interpreted to include not only the explicitly recited values of about 0.1% to about 5%, but also include individual values (e.g., about 1%, about 2%, about 3%, and about 4%) and the sub-ranges (e.g., about 0.5% to about 1.1%; about 5% to about 2.4%; about 0.5% to about 3.2%, and about 0.5% to about 4.4%, and other possible sub-ranges) within the indicated range.

As used herein, the terms "about," "approximate," "at or about," and "substantially" mean that the amount or value in question can be the exact value or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In such cases, it is generally understood, as used herein, that "about" and "at or about" mean the nominal value indicated ±10% variation unless otherwise indicated or inferred. In general, an amount, size, formulation, parameter or other quantity or characteristic is "about," "approximate," or "at or about" whether or not expressly stated to be such. It is understood that where "about," "approximate," or "at or about" is used before a quantitative value, the parameter also includes the specific quantitative value itself, unless specifically stated otherwise.

As used herein, the term "effective amount" refers to an amount that is sufficient to achieve the desired modification of a physical property of the composition or material. For example, an "effective amount" of a catalyst refers to an amount that is sufficient to achieve the desired improvement in the property modulated by the formulation component, e.g. achieving the desired level of modulus. The specific level in terms of wt % in a composition required as an effective amount will depend upon a variety of factors including the amount and type of substrate, solvent system, reaction temperature, and desired level of enantiomeric or diastereomeric excess.

As used herein, the terms "optional" or "optionally" means that the subsequently described event or circumstance can or cannot occur, and that the description includes instances where said event or circumstance occurs and instances where it does not.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —OCH$_2$CH$_2$O— units in the polyester, regardless of whether ethylene glycol was used to prepare the polyester. Similarly, a sebacic acid residue in a polyester refers to one or more —CO(CH$_2$)$_8$CO— moieties in the polyester, regardless of whether the residue is obtained by reacting sebacic acid or an ester thereof to obtain the polyester.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, "$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

The term "aliphatic" or "aliphatic group," as used herein, denotes a hydrocarbon moiety that may be straight-chain (i.e., unbranched), branched, or cyclic (including fused, bridging, and spirofused polycyclic) and may be completely saturated or may contain one or more units of unsaturation, but which is not aromatic. Unless otherwise specified, aliphatic groups contain 1-20 carbon atoms. Aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms. The term alkyl group can also be a C1 alkyl, C1-C2 alkyl, C1-C3 alkyl, C1-C4 alkyl, C1-C5 alkyl, C1-C6 alkyl, C1-C7 alkyl, C1-C8 alkyl, C1-C9 alkyl, C1-C10 alkyl, and the like up to and including a C1-C24 alkyl.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" or "haloalkyl" specifically refers to an alkyl group that is substituted with one or more halide, e.g., fluorine, chlorine, bromine, or iodine. Alternatively, the term "monohaloalkyl" specifically refers to an alkyl group that is substituted with a single halide, e.g. fluorine, chlorine, bromine, or iodine. The term "polyhaloalkyl" specifically refers to an alkyl group that is independently substituted with two or more halides, i.e. each halide substituent need not be the same halide as another halide substituent, nor do the multiple instances of a halide substituent need to be on the same carbon. The term "alkoxyalkyl" specifically refers to an alkyl group that is substituted with one or more alkoxy groups, as described below. The term "aminoalkyl" specifically refers to an alkyl group that is substituted with one or more amino groups. The term "hydroxyalkyl" specifically refers to an alkyl group that is substituted with one or more hydroxy groups. When "alkyl" is used in one instance and a specific term such as "hydroxyalkyl" is used in another, it is not meant to imply that the term "alkyl" does not also refer to specific terms such as "hydroxyalkyl" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, cycloalkyl, alkoxy, amino, ether, halide, hydroxy, nitro, silyl, sulfo-oxo, or thiol as described herein.

The term "alkanediyl" as used herein, refers to a divalent saturated aliphatic group, with one or two saturated carbon atom(s) as the point(s) of attachment, a linear or branched, cyclo, cyclic or acyclic structure, no carbon-carbon double or triple bonds, and no atoms other than carbon and hydrogen. The groups, —$CH_2$-(methylene), —$CH_2CH_2$—, —$CH_2C(CH_3)_2CH_2$—, and —$CH_2CH_2CH_2$— are non-limiting examples of alkanediyl groups.

The terms "alkoxy" and "alkoxyl" as used herein to refer to an alkyl or cycloalkyl group bonded through an ether linkage; that is, an "alkoxy" group can be defined as —$OA^1$ where $A^1$ is alkyl or cycloalkyl as defined above. "Alkoxy" also includes polymers of alkoxy groups as just described; that is, an alkoxy can be a polyether such as —$OA^1$-$OA^2$ or —$OA^1$-$(OA^2)_a$-$OA^3$, where "a" is an integer of from 1 to 200 and $A^1$, $A^2$, and $A^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as ($A^1A^2$)C=C($A^3A^4$) are intended to include both the E and Z isomers. This can be presumed in structural formulae herein wherein an asymmetric alkene is present, or it can be explicitly indicated by the bond symbol C≡C. The alkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C═C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aromatic group" as used herein refers to a ring structure having cyclic clouds of delocalized π electrons above and below the plane of the molecule, where the π clouds contain (4n+2) π electrons. A further discussion of aromaticity is found in Morrison and Boyd, Organic Chemistry, (5th Ed., 1987), Chapter 13, entitled "Aromaticity," pages 477-497, incorporated herein by reference. The term "aromatic group" is inclusive of both aryl and heteroaryl groups.

The term "aryl" as used herein is a group that contains any carbon-based aromatic group including, but not limited to, benzene, naphthalene, phenyl, biphenyl, anthracene, and the like. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, —NH$_2$, carboxylic acid, ester, ether, halide, hydroxy, ketone, azide, nitro, silyl, sulfo-oxo, or thiol as described herein. The term "biaryl" is a specific type of aryl group and is included in the definition of "aryl." In addition, the aryl group can be a single ring structure or comprise multiple ring structures that are either fused ring structures or attached via one or more bridging groups such as a carbon-carbon bond. For example, biaryl to two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" is a short hand notation for a carbonyl group, i.e., C═O.

The terms "amine" or "amino" as used herein are represented by the formula —NA$^1$A$^2$, where A$^1$ and A$^2$ can be, independently, hydrogen or alkyl, cycloalkyl, alkenyl, cycloalkenyl, alkynyl, cycloalkynyl, aryl, or heteroaryl group as described herein. A specific example of amino is —NH$_2$.

The term "alkylamino" as used herein is represented by the formula —NH(-alkyl) and —N(-alkyl)$_2$, where alkyl is a described herein. Representative examples include, but are not limited to, methylamino group, ethylamino group, propylamino group, isopropylamino group, butylamino group, isobutylamino group, (sec-butyl)amino group, (tert-butyl) amino group, pentylamino group, isopentylamino group, (tert-pentyl)amino group, hexylamino group, dimethylamino group, diethylamino group, dipropylamino group, diisopropylamino group, dibutylamino group, diisobutylamino group, di(sec-butyl)amino group, di(tert-butyl) amino group, dipentylamino group, diisopentylamino group, di(tert-pentyl)amino group, dihexylamino group, N-ethyl-N-methylamino group, N-methyl-N-propylamino group, N-ethyl-N-propylamino group and the like.

The term "carboxylic acid" as used herein is represented by the formula —C(O)OH.

The term "ester" as used herein is represented by the formula —OC(O)A$^1$ or —C(O)OA$^1$, where A$^1$ can be alkyl, cycloalkyl, alkenyl, cycloalkenyl, alkynyl, cycloalkynyl, aryl, or heteroaryl group as described herein. The term "polyester" as used herein is represented by the formula -(A$^1$O(O)C-A$^2$-C(O)O)$_a$— or -(A$^1$O)C-A$^2$-OC(O))$_a$—, where A$^1$ and A$^2$ can be, independently, an alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by the formula A$^1$OA$^2$, where A$^1$ and A$^2$ can be, independently, an alkyl, cycloalkyl, alkenyl, cycloalkenyl, alkynyl, cycloalkynyl, aryl, or heteroaryl group described herein. The term "polyether" as used herein is represented by the formula -(A$^1$O-A$^2$O)$_a$—, where A$^1$ and A$^2$ can be, independently, an alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The terms "halo," "halogen" or "halide," as used herein can be used interchangeably and refer to F, Cl, Br, or I.

The terms "pseudohalide," "pseudohalogen" or "pseudohalo," as used herein can be used interchangeably and refer to functional groups that behave substantially similar to halides. Such functional groups include, by way of example, cyano, thiocyanato, azido, trifluoromethyl, trifluoromethoxy, perfluoroalkyl, and perfluoroalkoxy groups.

The term "heteroalkyl" as used herein refers to an alkyl group containing at least one heteroatom. Suitable heteroatoms include, but are not limited to, O, N, Si, P and S, wherein the nitrogen, phosphorous and sulfur atoms are optionally oxidized, and the nitrogen heteroatom is optionally quaternized. Heteroalkyls can be substituted as defined above for alkyl groups.

The term "heteroaryl" as used herein refers to an aromatic group that has at least one heteroatom incorporated within the ring of the aromatic group. Examples of heteroatoms include, but are not limited to, nitrogen, oxygen, sulfur, and phosphorus, where N-oxides, sulfur oxides, and dioxides are permissible heteroatom substitutions. The heteroaryl group can be substituted or unsubstituted. The heteroaryl group can be substituted with one or more groups including, but not limited to, alkyl, cycloalkyl, alkoxy, amino, ether, halide, hydroxy, nitro, silyl, sulfo-oxo, or thiol as described herein. Heteroaryl groups can be monocyclic, or alternatively fused ring systems. Heteroaryl groups include, but are not limited to, furyl, imidazolyl, pyrimidinyl, tetrazolyl, thienyl, pyridinyl, pyrrolyl, N-methylpyrrolyl, quinolinyl, isoquinolinyl, pyrazolyl, triazolyl, thiazolyl, oxazolyl, isoxazolyl, oxadiazolyl, thiadiazolyl, isothiazolyl, pyridazinyl, pyrazinyl, benzofuranyl, benzodioxolyl, benzothiophenyl, indolyl, indazolyl, benzimidazolyl, imidazopyridinyl, pyrazolopyridinyl, and pyrazolopyrimidinyl. Further not limiting examples of heteroaryl groups include, but are not limited to, pyridinyl, pyridazinyl, pyrimidinyl, pyrazinyl, thiophenyl, pyrazolyl, imidazolyl, benzo[d]oxazolyl, benzo[d]thiazolyl, quinolinyl, quinazolinyl, indazolyl, imidazo[1,2-b]pyridazinyl, imidazo[1,2-a]pyrazinyl, benzo[c][1,2,5]thiadiazolyl, benzo[c][1,2,5]oxadiazolyl, and pyrido[2,3-b]pyrazinyl.

The terms "heterocycle" or "heterocyclyl," as used herein can be used interchangeably and refer to single and multi-cyclic aromatic or non-aromatic ring systems in which at least one of the ring members is other than carbon. Thus, the term is inclusive of, but not limited to, "heterocycloalkyl," "heteroaryl," "bicyclic heterocycle," and "polycyclic heterocycle." Heterocycle includes pyridine, pyrimidine, furan, thiophene, pyrrole, isoxazole, isothiazole, pyrazole, oxazole, thiazole, imidazole, oxazole, including, 1,2,3-oxadiazole, 1,2,5-oxadiazole and 1,3,4-oxadiazole, thiadiazole, including, 1,2,3-thiadiazole, 1,2,5-thiadiazole, and 1,3,4-thiadiazole, triazole, including, 1,2,3-triazole, 1,3,4-triazole, tetrazole, including 1,2,3,4-tetrazole and 1,2,4,5-tetrazole, pyridazine, pyrazine, triazine, including 1,2,4-triazine and 1,3,5-triazine, tetrazine, including 1,2,4,5-tetrazine, pyrrolidine, piperidine, piperazine, morpholine, azetidine, tetrahydropyran, tetrahydrofuran, dioxane, and the like. The term heterocyclyl group can also be a C2 heterocyclyl, C2-C3 heterocyclyl, C2-C4 heterocyclyl, C2-C5 heterocyclyl, C2-C6 heterocyclyl, C2-C7 heterocyclyl, C2-C8 heterocyclyl, C2-C9 heterocyclyl, C2-C10 heterocyclyl, C2-C11 heterocyclyl, and the like up to and including a C2-C18 heterocyclyl. For example, a C2 heterocyclyl comprises a group which has two carbon atoms and at least one heteroatom, including, but not limited to, aziridinyl, diazetidinyl, dihydrodiazetyl, oxiranyl, thiiranyl, and the like. Alternatively, for example, a C5 heterocyclyl comprises a group which has five carbon atoms and at least one heteroatom, including, but not limited to, piperidinyl, tetrahydropyranyl, tetrahydrothiopyranyl, diazepanyl, pyridinyl, and the like. It is understood that a heterocyclyl group may be bound either through a heteroatom in the ring, where chemically possible, or one of carbons comprising the heterocyclyl ring.

The term "bicyclic heterocycle" or "bicyclic heterocyclyl" as used herein refers to a ring system in which at least one of the ring members is other than carbon. Bicyclic heterocyclyl encompasses ring systems wherein an aromatic ring is fused with another aromatic ring, or wherein an aromatic ring is fused with a non-aromatic ring. Bicyclic heterocyclyl encompasses ring systems wherein a benzene ring is fused to a 5- or a 6-membered ring containing 1, 2 or 3 ring heteroatoms or wherein a pyridine ring is fused to a 5- or a 6-membered ring containing 1, 2 or 3 ring heteroatoms. Bicyclic heterocyclic groups include, but are not limited to, indolyl, indazolyl, pyrazolo[1,5-a]pyridinyl, benzofuranyl, quinolinyl, quinoxalinyl, 1,3-benzodioxolyl, 2,3-dihydro-1,4-benzodioxinyl, 3,4-dihydro-2H-chromenyl, 1H-pyrazolo[4,3-c]pyridin-3-yl; 1H-pyrrolo[3,2-b]pyridin-3-yl; and 1H-pyrazolo[3,2-b]pyridin-3-yl.

The term "heterocycloalkyl" as used herein refers to an aliphatic, partially unsaturated or fully saturated, 3- to 14-membered ring system, including single rings of 3 to 8 atoms and bi- and tricyclic ring systems. The heterocycloalkyl ring-systems include one to four heteroatoms independently selected from oxygen, nitrogen, and sulfur, wherein a nitrogen and sulfur heteroatom optionally can be oxidized and a nitrogen heteroatom optionally can be substituted. Representative heterocycloalkyl groups include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The term "hydroxyl" or "hydroxy" as used herein is represented by the formula —OH.

The term "ketone" as used herein is represented by the formula $A^1C(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "azide" or "azido" as used herein is represented by the formula —$N_3$.

The term "nitro" as used herein is represented by the formula —$NO_2$.

The term "nitrile" or "cyano" as used herein is represented by the formula —CN.

The term "silyl" as used herein is represented by the formula —$SiA^1A^2A^3$, where $A^1$, $A^2$, and $A^3$ can be, independently, hydrogen or an alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas —$S(O)A^1$, —$S(O)_2A^1$, —$OS(O)_2A^1$, or —$OS(O)_2OA^1$, where $A^1$ can be hydrogen or an alkyl, cycloalkyl, alkenyl, cycloalkenyl, alkynyl, cycloalkynyl, aryl, or heteroaryl group as described herein. Throughout this specification "S(O)" is a short hand notation for S=O. The term "sulfonyl" is used herein to refer to the sulfo-oxo group represented by the formula —$S(O)_2A^1$, where $A^1$ can be hydrogen or an alkyl, cycloalkyl, alkenyl, cycloalkenyl, alkynyl, cycloalkynyl, aryl, or heteroaryl group as described herein. The term "sulfone" as used herein is represented by the formula $A^1S(O)_2A^2$, where $A^1$ and $A^2$ can be, independently, an alkyl, cycloalkyl, alkenyl, cycloalkenyl, alkynyl, cycloalkynyl, aryl, or heteroaryl group as described herein. The term "sulfoxide" as used herein is represented by the formula $A^1S(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "thiol" as used herein is represented by the formula —SH.

"$R^1$," "$R^2$," "$R^3$," . . . "$R^n$," where n is an integer, as used herein can, independently, possess one or more of the groups listed above. For example, if $R^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. In is also contemplated that, in certain aspects, unless expressly indicated to the contrary, individual substituents can be further optionally substituted (i.e., further substituted or unsubstituted).

The term "stable," as used herein, refers to compounds that are not substantially altered when subjected to conditions to allow for their production, detection, and, in certain aspects, their recovery, purification, and use for one or more of the purposes disclosed herein.

Suitable monovalent substituents on a substitutable carbon atom of an "optionally substituted" group are independently halogen; —$(CH_2)_{0-4}R°$; —$(CH_2)_{0-4}OR°$; —$O(CH_2)_{0-4}R°$, —$O—(CH_2)_{0-4}C(O)OR°$; —$(CH_2)_{0-4}CH(OR°)_2$; —$(CH_2)_{0-4}SR°$; —$(CH_2)_{0-4}Ph$, which may be substituted with $R°$; —$(CH_2)_{0-4}O(CH_2)_{0-1}Ph$ which may be substituted with $R°$; —CH=CHPh, which may be substituted with $R°$; —$(CH_2)_{0-4}O(CH_2)_{0-1}$-pyridyl which may be substituted with $R°$; —$NO_2$; —CN; —$N_3$; —$(CH_2)_{0-4}N(R°)_2$; —$(CH_2)_{0-4}N(R°)C(O)R°$; —$N(R°)C(S)R°$; —$(CH_2)_{0-4}N(R°)C(O)NR°_2$; —$N(R°)C(S)NR°_2$; —$(CH_2)_{0-4}N(R°)C(O)OR°$; —$N(R°)N(R°)C(O)R°$; —$N(R°)N(R°)C(O)NR°_2$; —$N(R°)N(R°)C(O)OR°$; —$(CH_2)_{0-4}C(O)R°$; —$C(S)R°$; —$(CH_2)_{0-4}C(O)OR°$; —$(CH_2)_{0-4}C(O)SR°$; —$(CH_2)_{0-4}C(O)OSiR°_3$; —$(CH_2)_{0-4}OC(O)R°$; —$OC(O)(CH_2)_{0-4}SR$—, $SC(S)SR°$; —$(CH_2)_{0-4}SC(O)R°$; —$(CH_2)_{0-4}C(O)NR°_2$; —$C(S)NR°_2$; —$C(S)SR°$; —$(CH_2)_{0-4}OC(O)NR°_2$; —$C(O)N(OR°)R°$; —$C(O)C(O)R°$; —$C(O)CH_2C(O)R°$; —$C(NOR°)R°$; —$(CH_2)_{0-4}SSR°$; —$(CH_2)_{0-4}S(O)_2R°$; —$(CH_2)_{0-4}S(O)_2OR°$; —$(CH_2)_{0-4}OS(O)_2R°$; —$S(O)_2NR°_2$; —$(CH_2)_{0-4}S(O)R°$; —$N(R°)S(O)_2NR°_2$; —$N(R°)S(O)_2R°$; —$N(OR°)R°$; —$C(NH)NR°_2$; —$P(O)_2R°$; —$P(O)R°_2$; —$OP(O)R°_2$; —$OP(O)(OR°)_2$; $SiR°_3$; —$(C_{1-4}$ straight or branched alkylene)$O—N(R°)_2$; or —$(C_{1-4}$ straight or branched)alkylene)$C(O)O—(R°)_2$, wherein each $R°$ may be substituted as defined below and is independently hydrogen, $C_{1-6}$ aliphatic, —$CH_2Ph$, —$O(CH_2)_{0-1}Ph$, —$CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R°$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R°$ (or the ring formed by taking two independent occurrences of $R°$ together with their intervening atoms), are independently halogen, —$(CH_2)_{0-2}R.$, -(haloR.), —$(CH_2)_{0-2}OH$, —$(CH_2)_{0-2}OR.$, —$(CH_2)_{0-2}CH(OR.)_2$; —$O(haloR.)$, —CN, —$N_3$, —$(CH_2)_{0-2}C(O)R.$, —$(CH_2)_{0-2}C(O)OH$, —$(CH_2)_{0-2}C(O)OR.$, —$(CH_2)_{0-2}SR.$, —$(CH_2)_{0-2}SH$, —$(CH_2)_{0-2}NH_2$, —$(CH_2)_{0-2}NHR.$, —$(CH_2)_{0-2}NR._2$, —$NO_2$, —$SiR._3$, —$OSiR._3$, —$C(O)SR.$, —$(C_{1-4}$ straight or branched alkylene)$C(O)OR.$, or —SSR. wherein each R. is unsubstituted or where preceded by "halo" is substituted only with one or more halogens, and is independently selected from $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of $R°$ include =O and =S.

Suitable divalent substituents on a saturated carbon atom of an "optionally substituted" group include the following: =O, =S, =$NNR*_2$, =$NNHC(O)R*$, =$NNHC(O)OR*$, =$NNHS(O)_2R*$, =$NR*$, =$NOR*$, —$O(C(R*_2))_{2-3}O$—, or —$S(C(R*_2))_{2-3}S$—, wherein each independent occurrence of $R*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —$O(CR*_2)_{2-3}O$—, wherein each independent occurrence of $R*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of $R*$ include halogen, —R., -(haloR.), —OH, —OR., —O(haloR.), —CN, —C(O)OH, —C(O)OR., —$NH_2$, —NHR., —$NR._2$, or —$NO_2$, wherein each R. is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —$R^†$, —$NR^†_2$, —$C(O)R^†$, —$C(O)OR^†$, —$C(O)C(O)R^†$, —$C(O)CH_2C(O)R^†$, —$S(O)_2R^†$, —$S(O)_2NR^†_2$, —$C(S)NR^†_2$, —$C(NH)NR^†_2$, or —$N(R^†)S(O)_2R^†$; wherein each $R^†$ is independently hydrogen, $C_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of $R^†$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R† are independently halogen, —R., -(haloR.), —OH, —OR., —O(haloR.), —CN, —C(O)OH, —C(O)OR., —NH₂, —NHR., —NR.₂, or —NO₂, wherein each R. is unsubstituted or where preceded by "halo" is substituted only with one or more halogens, and is independently C₁₋₄ aliphatic, —CH₂Ph, —O(CH₂)₀₋₁Ph, or a 5-6-membered saturated, partially unsaturated, or aryl ring having 0-4 heteroatoms independently selected from nitrogen, oxygen, or sulfur.

The term "leaving group" refers to an atom (or a group of atoms) with electron withdrawing ability that can be displaced as a stable species, taking with it the bonding electrons. Examples of suitable leaving groups include halides and sulfonate esters, including, but not limited to, triflate, mesylate, tosylate, and brosylate.

The terms "hydrolysable group" and "hydrolysable moiety" refer to a functional group capable of undergoing hydrolysis, e.g., under basic or acidic conditions. Examples of hydrolysable residues include, without limitation, acid halides, activated carboxylic acids, and various protecting groups known in the art (see, for example, "Protective Groups in Organic Synthesis," T. W. Greene, P. G. M. Wuts, Wiley-Interscience, 1999).

The term "organic residue" defines a carbon containing residue, i.e., a residue comprising at least one carbon atom, and includes but is not limited to the carbon-containing groups, residues, or radicals defined hereinabove. Organic residues can contain various heteroatoms, or be bonded to another molecule through a heteroatom, including oxygen, nitrogen, sulfur, phosphorus, or the like. Examples of organic residues include but are not limited alkyl or substituted alkyls, alkoxy or substituted alkoxy, mono or di-substituted amino, amide groups, etc. Organic residues can preferably comprise 1 to 18 carbon atoms, 1 to 15, carbon atoms, 1 to 12 carbon atoms, 1 to 8 carbon atoms, 1 to 6 carbon atoms, or 1 to 4 carbon atoms. In a further aspect, an organic residue can comprise 2 to 18 carbon atoms, 2 to 15, carbon atoms, 2 to 12 carbon atoms, 2 to 8 carbon atoms, 2 to 4 carbon atoms, or 2 to 4 carbon atoms.

A very close synonym of the term "residue" is the term "radical," which as used in the specification and concluding claims, refers to a fragment, group, or substructure of a molecule described herein, regardless of how the molecule is prepared. For example, a 2,4-thiazolidinedione radical in a particular compound has the structure:

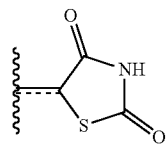

regardless of whether thiazolidinedione is used to prepare the compound. In some embodiments the radical (for example an alkyl) can be further modified (i.e., substituted alkyl) by having bonded thereto one or more "substituent radicals." The number of atoms in a given radical is not critical to the present invention unless it is indicated to the contrary elsewhere herein.

"Organic radicals," as the term is defined and used herein, contain one or more carbon atoms. An organic radical can have, for example, 1-26 carbon atoms, 1-18 carbon atoms, 1-12 carbon atoms, 1-8 carbon atoms, 1-6 carbon atoms, or 1-4 carbon atoms. In a further aspect, an organic radical can have 2-26 carbon atoms, 2-18 carbon atoms, 2-12 carbon atoms, 2-8 carbon atoms, 2-6 carbon atoms, or 2-4 carbon atoms. Organic radicals often have hydrogen bound to at least some of the carbon atoms of the organic radical. One example, of an organic radical that comprises no inorganic atoms is a 5,6,7,8-tetrahydro-2-naphthyl radical. In some embodiments, an organic radical can contain 1-10 inorganic heteroatoms bound thereto or therein, including halogens, oxygen, sulfur, nitrogen, phosphorus, and the like. Examples of organic radicals include but are not limited to an alkyl, substituted alkyl, cycloalkyl, substituted cycloalkyl, mono-substituted amino, di-substituted amino, acyloxy, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals and the like.

"Inorganic radicals," as the term is defined and used herein, contain no carbon atoms and therefore comprise only atoms other than carbon. Inorganic radicals comprise bonded combinations of atoms selected from hydrogen, nitrogen, oxygen, silicon, phosphorus, sulfur, selenium, and halogens such as fluorine, chlorine, bromine, and iodine, which can be present individually or bonded together in their chemically stable combinations. Inorganic radicals have 10 or fewer, or preferably one to six or one to four inorganic atoms as listed above bonded together. Examples of inorganic radicals include, but not limited to, amino, hydroxy, halogens, nitro, thiol, sulfate, phosphate, and like commonly known inorganic radicals. The inorganic radicals do not have bonded therein the metallic elements of the periodic table (such as the alkali metals, alkaline earth metals, transition metals, lanthanide metals, or actinide metals), although such metal ions can sometimes serve as a pharmaceutically acceptable cation for anionic inorganic radicals such as a sulfate, phosphate, or like anionic inorganic radical. Inorganic radicals do not comprise metalloids elements such as boron, aluminum, gallium, germanium, arsenic, tin, lead, or tellurium, or the noble gas elements, unless otherwise specifically indicated elsewhere herein.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or meaning that the compound is levorotatory. A compound prefixed with (+) or d is dextrorotatory. For a given chemical structure, these compounds, called stereoisomers, are identical except that they are non-superimposable mirror images of one another. A specific stereoisomer can also be referred to as an enantiomer, and a mixture of such isomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Ingold-Prelog system can be used to assign the (R) or (S) configuration to a chiral carbon.

Compounds described herein comprise atoms in both their natural isotopic abundance and in non-natural abundance. The disclosed compounds can be isotopically-labeled or isotopically-substituted compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, sulfur, fluorine and chlorine, such as $^2H$, $^3H$, $^{13}C$, $^{14}C$, $^{15}N$, $^{18}O$, $^{17}O$, $^{35}S$, $^{18}F$, and $^{36}Cl$, respectively. Compounds further comprise prodrugs thereof and pharmaceutically acceptable salts of said compounds or of said prodrugs which contain the aforementioned isotopes and/or other isotopes of other atoms are within the scope of this invention. Certain isotopically-labeled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labeled compounds of the present invention and prodrugs thereof can generally be prepared by carrying out the procedures below, by substituting a readily available isotopically labeled reagent for a non-isotopically labeled reagent.

It is known that chemical substances form solids which are present in different states of order which are termed polymorphic forms or modifications. The different modifications of a polymorphic substance can differ greatly in their physical properties. The compounds according to the invention can be present in different polymorphic forms, with it being possible for particular modifications to be metastable. Unless stated to the contrary, the invention includes all such possible polymorphic forms.

In some aspects, a structure of a compound can be represented by a formula:

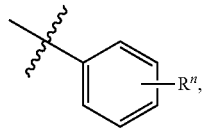

which is understood to be equivalent to a formula:

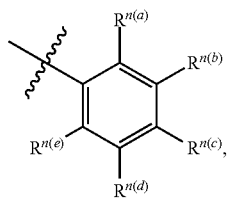

wherein n is typically an integer. That is, $R^n$ is understood to represent five independent substituents, $R^{n(a)}$, $R^{n(b)}$, $R^{n(c)}$, $R^{n(d)}$, and $R^{n(e)}$. By "independent substituents," it is meant that each R substituent can be independently defined. For example, if in one instance $R^{n(a)}$ is halogen, then $R^{n(b)}$ is not necessarily halogen in that instance.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

In various aspects, the disclosed compounds can possess at least one center of asymmetry, they can be present in the form of their racemates, in the form of the pure enantiomers and/or diastereomers or in the form of mixtures of these enantiomers and/or diastereomers. The stereoisomers can be present in the mixtures in any arbitrary proportions. In some aspects, provided this is possible, the disclosed compounds can be present in the form of the tautomers.

Thus, methods which are known per se can be used, for example, to separate the disclosed compounds which possess one or more chiral centers and occur as racemates into their optical isomers, i.e., enantiomers or diastereomers. The separation can be effected by means of column separation on chiral phases or by means of recrystallization from an optically active solvent or using an optically active acid or base or by means of derivatizing with an optically active reagent, such as an optically active alcohol, and subsequently cleaving off the residue.

Unless otherwise specified, temperatures referred to herein are based on atmospheric pressure (i.e. one atmosphere).

Figure 2:
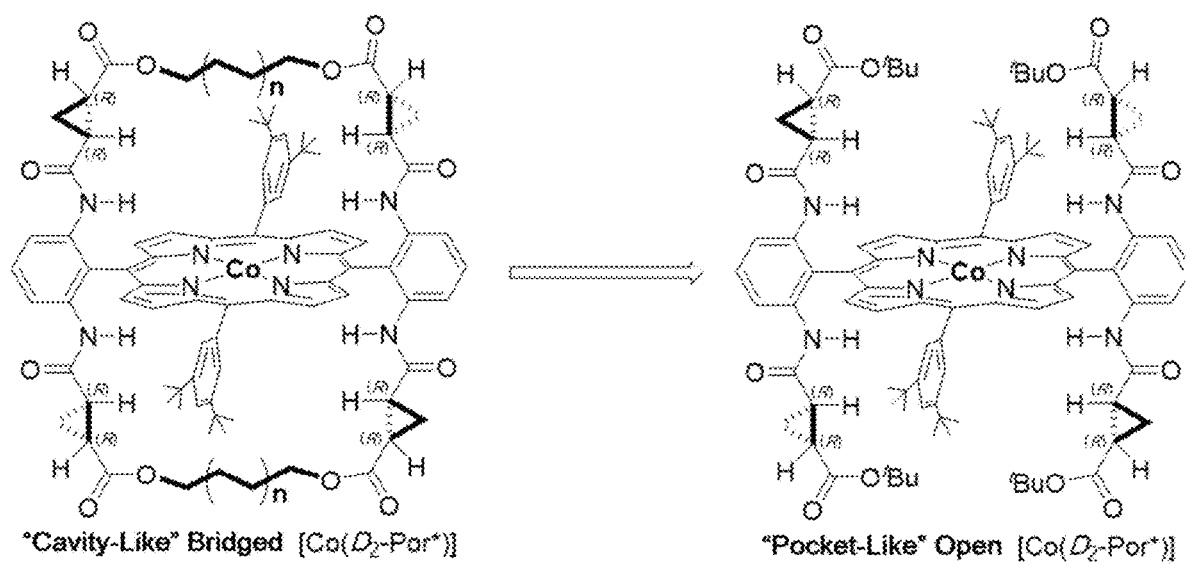
FIG. 2 shows creation of a cavity-like chiral environment via bridging according to one aspect of the present disclosure.

Control of Enantioselectivity and Diastereoselectivity Using Metalloradical Catalysis Control of enantioselectivity and diastereoselectivity remains a major challenge in radical chemistry. In one aspect, the emergence of metalloradical catalysis offers a conceptually new strategy for addressing this and other outstanding issues. Further in this aspect, through the employment of $D_2$-symmetric chiral amidoporphyrins as the supporting ligands, Co(II)-based metalloradical catalysis has enabled the development of new catalytic systems for asymmetric radical transformations with a unique profile of reactivity and selectivity. In one aspect, disclosed herein are novel $D_2$-symmetric chiral amidoporphyrins with alkyl bridges across two chiral amide units on both sides of the porphyrin plane (designated as "HuPhyrin"). In a further aspect, disclosed herein is a modular synthesis method of HuPhyrins, wherein the synthesis method permits variation of bridge length. In a still further aspect, the Co(II) complexes of HuPhyrin (herein "[Co(HuPhyrin)]") represent new-generation metalloradical catalysts where the metal-centered d-radical is situated inside a cavity-like ligand with a more rigid chiral environment and enhanced hydrogen-bonding capability (see FIG. 2). In a further aspect, bridged [Co(HuPhyrin)] used in cyclopropanation and aziridination reactions functions notably differently from open (i.e., unbridged) catalysts, exhibiting significant enhancements in reactivity and stereoselectivity. In a still further aspect, the length of the distal alkyl bridge can have a remarkable influence on the catalytic properties of the HuPhyrins disclosed herein.

Catalyst Compositions

In various aspects, the catalysts disclosed herein can have Formula I:

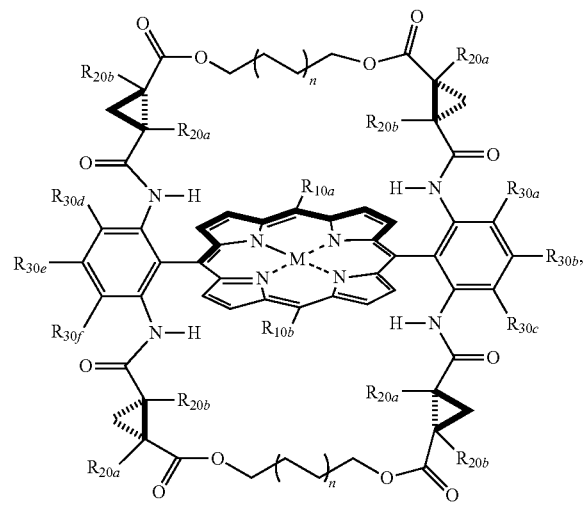

wherein each of $R_{10a}$ and $R_{10b}$ is independently an aryl group independently substituted with 1, 2, 3, 4, or 5 groups selected from halogen, hydroxy, amino, and C1-C10 alkyl; wherein each occurrence of $R_{20a}$ and $R_{20b}$ is independently substituted with hydrogen and C1-C3 alkyl; wherein each of $R^{30a}$, $R^{30b}$, $R^{30c}$, $R^{30d}$, $R^{30e}$, and $R^{30f}$ is independently selected from hydrogen, hydroxy, amino, and C1-C10 alkyl; and wherein n is selected from 0, 1, 2, 3, 4, 5, 6, 7, 8, 9, 10, 11, 12, 13, 14, 15, 16, 17, 18, 19, and 20. In a further aspect, the catalyst is prepared by methods as disclosed herein, e.g., the Examples, and as would be generally adapted by a skilled artisan.

In a further aspect, each of $R_{10a}$ and $R_{10b}$ is independently a monocyclic aryl group substituted with 1, 2, 3, 4, or 5 groups selected from halogen, hydroxy, amino, and C1-C10 alkyl. In a still further aspect, each of $R_{10a}$ and $R_{10b}$ is independently a phenyl group substituted with 1, 2, 3, 4, or 5 groups selected from halogen, hydroxy, amino, and C1-C10 alkyl. In a yet further aspect, each of $R_{10a}$ and $R_{10b}$ is independently a phenyl group independently substituted with 1, 2, or 3 groups selected from a C1-C10 alkyl. In an even further aspect, each of $R_{10a}$ and $R_{10b}$ is independently a phenyl group independently substituted with 1, 2, or 3 groups selected from a C1-C6 alkyl. In a still further aspect, each of $R_{10a}$ and $R_{10b}$ is independently a phenyl group substituted with 1, 2, or 3 t-butyl groups.

In a further aspect, each occurrence of $R_{20a}$ and $R_{20b}$ is the same and is selected from hydrogen and C1-C3 alkyl.

In a further aspect, each of $R^{30a}$, $R^{30b}$, $R^{30c}$, $R^{30d}$, $R^{30e}$, and $R^{30f}$ is independently selected from hydrogen and C1-C10 alkyl. In a still further aspect, each of $R^{30a}$, $R^{30b}$, $R^{30c}$, $R^{30d}$, $R^{30e}$, and $R^{30f}$ is independently selected from a C1-C10 alkyl. In yet further aspect, each of $R^{30a}$, $R^{30b}$, $R^{30c}$, $R^{30d}$, $R^{30e}$, and $R^{30f}$ is hydrogen.

In a further aspect, n is selected from 0, 1, 2, 3, 4, 5, 6, 7, 8, 9, 10, 11, 12, 13, 14, 15, 16, 17, 18, 19, and 20, or any set or group of the foregoing values. In a yet further aspect, n is selected from 0, 1, 2, 3, 4, 5, and 6. In a still further aspect, n is selected from 1, 2, 3, 4, 5, and 6. In a yet further aspect, n is selected from 0, 1, 2, 3, 4, and 5. In a still further aspect, n is selected from 1, 2, 3, 4, and 5. In a yet further aspect, n is selected from 0, 1, 2, 3, and 4. In a still further aspect, n is selected from 1, 2, 3, and 4.

In one aspect, the catalysts disclosed herein can have Formula II:

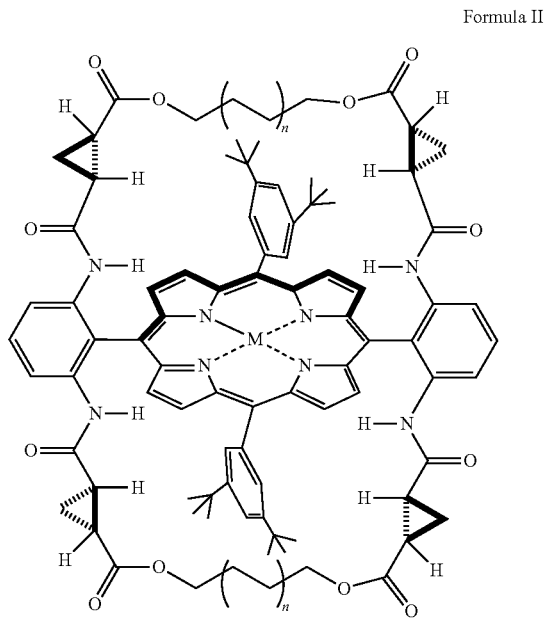

Formula II

In another aspect, the stereocenters in the catalyst can be synthesized with any desired configuration. In one aspect, the stereocenters all have the (R) configuration.

In another aspect, the central porphyrin moiety of the catalyst coordinates a metal atom. In a further aspect, the metal can be cobalt, zinc, aluminum, magnesium, nickel, copper, manganese, iron, germanium, tin, molybdenum, ruthenium, or a combination thereof. In some aspects, the metal is cobalt.

In yet another aspect, n in Formula I can be from 1 to 4, or can be 1, 2, 3, or 4. In one aspect, n is 1. In an alternative aspect, n is 2.

Methods of Using the Catalyst Compositions

In various aspects, disclosed herein is a method for the stereoselective synthesis of chiral cyclopropane derivatives, wherein the method includes the steps of contacting a diazo substrate and a vinyl-containing substrate with the catalysts disclosed herein. In one aspect, the method is carried out in a solvent. In a further aspect, the solvent can be toluene, chlorobenzene, another solvent, or a combination thereof. In a still further aspect, the method is conducted at room temperature for about an hour. In a yet further aspect, the method can be conducted under an inert atmosphere including, but not limited to, nitrogen or argon gas, or a combination thereof. In a further aspect, the diazo substrate can be ethyl diazoacetate. In a still further aspect, the vinyl-containing substrate can be styrene.

In a further aspect, the chiral cyclopropane derivative can be represented by Formula III:

Formula III wherein $R_{100}$ is C1-C10 substituted alkyl, substituted aryl, substituted heteroaryl, substituted cycloalkyl, and substituted heteroalkyl; wherein $R_{200}$ is —(C=O)$R_{40}$; wherein $R_{40}$ is selected from substituted alkyl, substituted aryl, substituted heteroaryl, substituted cycloalkyl, and substituted heteroalkyl, —NR$_{41}$R$_{42}$, —OR$_{41}$, —SR$_{41}$; and herein each of $R_{41}$ and $R_{42}$ is independently selected from hydrogen, substituted alkyl, substituted aryl, substituted heteroaryl, substituted cycloalkyl, and substituted heteroalkyl.

In another aspect, the compound of Formula III can have the following structure:

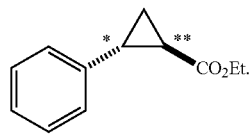 [SMILES: CCOC(=O)[C@@H]1C[C@H]1c1ccccc1]

In one aspect, * and ** represent stereocenters. In one aspect, the ratio of (R) to (S) enantiomer at the carbon indicated by * is from about 5:95 to about 95:5, or is about 5:95, 10:90, 15:85, 20:80, 25:75, 30:70, 35:65, 40:60, 45:55, 50:50, 55:45, 60:40, 65:35, 70:30, 75:25, 80:20, 85:15, 90:10, or about 95:5, or a combination of any of the foregoing values, or a range encompassing any of the foregoing values. In another aspect, the ratio of (R) to (S) enantiomer at the carbon indicated by ** is from about 5:95 to about 95:5, or is about 5:95, 10:90, 15:85, 20:80, 25:75, 30:70, 35:65, 40:60, 45:55, 50:50, 55:45, 60:40, 65:35, 70:30, 75:25, 80:20, 85:15, 90:10, or about 95:5, or a combination of any of the foregoing values, or a range encompassing any of the foregoing values.

In various aspects, the chiral cyclopropane derivative can include a mixture of diastereomers. In one aspect, the mixture of diastereomers includes at least 80% of a compound having (R) configuration at the carbons indicated by * and **, or at least 85%, 90%, or 95% of a compound having (R) configuration at the carbons indicated by * and **, or a combination of any of the foregoing values, or a range encompassing any of the foregoing values.

In various aspects, disclosed herein is a method for the stereoselective synthesis of chiral aziridine derivatives, wherein the method includes the steps of contacting an azido-containing substrate and a vinyl-containing substrate with the catalysts disclosed herein. In one aspect, the method is carried out in a solvent. In a further aspect, the solvent can be toluene, chlorobenzene, another solvent, or a combination thereof. In a further aspect, the method is conducted at 0° C. for about 24 hours. In another aspect, the method can be conducted under an inert atmosphere including, but not limited to, nitrogen or argon gas, or a combination thereof. In a still further aspect, the diazo substrate can be trichloroethoxysulfonyl azide. In yet further aspect, the vinyl-containing substrate can be styrene.

In a further aspect, the chiral aziridine derivative can be represented by Formula IV:

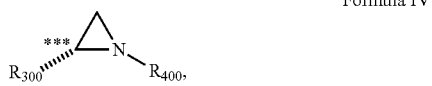

Formula IV wherein $R_{300}$ is C1-C10 substituted alkyl, substituted aryl, substituted heteroaryl, substituted cycloalkyl, and substituted heteroalkyl; wherein $R_{400}$ is —(C=O)$R_{40}$; wherein $R_{40}$ is selected from substituted alkyl, substituted aryl, substituted heteroaryl, substituted cycloalkyl, and substituted heteroalkyl, —$NR_{41}R_{42}$, —$OR_{41}$, —$SR_{41}$; and herein each of $R_{41}$ and $R_{42}$ is independently selected from hydrogen, substituted alkyl, substituted aryl, substituted heteroaryl, substituted cycloalkyl, and substituted heteroalkyl.

In another aspect, the compound of Formula IV can have the following structure:

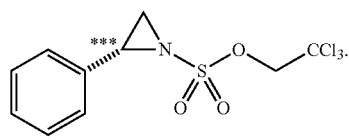

In one aspect, * represents a stereocenter. In one aspect, the ratio of (R) to (S) enantiomer at the carbon indicated by * is from about 5:95 to about 95:5, or is about 5:95, 10:90, 15:85, 20:80, 25:75, 30:70, 35:65, 40:60, 45:55, 50:50, 55:45, 60:40, 65:35, 70:30, 75:25, 80:20, 85:15, 90:10, or about 95:5, or a combination of any of the foregoing values, or a range encompassing any of the foregoing values.

In one aspect, disclosed herein are chiral cyclopropanes and compositions including chiral cyclopropanes produced by the disclosed methods, as well as chiral aziridines and compositions including chiral aziridines produced by the disclosed methods.

In various aspects, the disclosed method of preparing a chiral cyclopropane derivative can be carried out as shown in the following reaction:

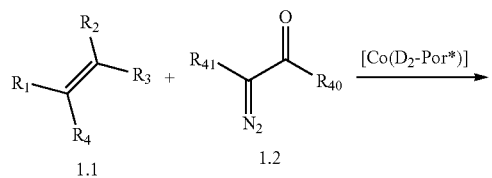

-continued

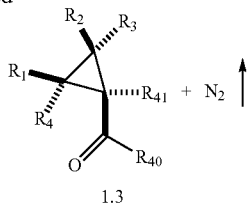

In the foregoing reaction, the following definitions apply to the substituent groups: each of $R_1$, $R_2$, $R_3$, and $R_4$ is independently selected from C1-C10 substituted alkyl, substituted aryl, substituted heteroaryl, substituted cycloalkyl, and substituted heteroalkyl; $R_{40}$ is selected from substituted alkyl, substituted aryl, substituted heteroaryl, substituted cycloalkyl, substituted heteroalkyl, —$NR_{51}R_{52}$, —$OR_{51}$, —$SR_{51}$; each of $R_{51}$ and $R_{52}$ is independently selected from hydrogen, substituted alkyl, substituted aryl, substituted heteroaryl, substituted cycloalkyl, and substituted heteroalkyl; and $R_{41}$ is selected from substituted alkyl, substituted aryl, substituted heteroaryl, substituted cycloalkyl, and substituted heteroalkyl.

In a further aspect, with regard to the foregoing reaction, the molar or equivalent ratio of compound 1.1 to compound 1.2 can be a suitable ratio, e.g., a ratio of from about 0.5 to about 10, about 0.5 to about 9, about 0.5 to about 8, about 0.5 to about 8, about 0.5 to about 7, about 0.5 to about 6, about 0.5 to about 5, about 0.5 to about 4, about 0.5 to about 3, about 0.5 to about 2.9, about 0.5 to about 2.8, about 0.5 to about 2.7, about 0.5 to about 2.6, about 0.5 to about 2.5, about 0.5 to about 2.4, about 0.5 to about 2.3, about 0.5 to about 2.2, about 0.5 to about 2.1, about 0.5 to about 2.0, about 0.5 to about 1.9, about 0.5 to about 1.8, about 0.5 to about 1.7, about 0.5 to about 1.6, about 0.5 to about 1.5, about 0.5 to about 1.4, about 0.5 to about 1.3, about 0.5 to about 1.2, about 0.5 to about 1.1, about 0.5 to about 1.0, about 0.6 to about 10, about 0.6 to about 9, about 0.6 to about 8, about 0.6 to about 8, about 0.6 to about 7, about 0.6 to about 6, about 0.6 to about 5, about 0.6 to about 4, about 0.6 to about 3, about 0.6 to about 2.9, about 0.6 to about 2.8, about 0.6 to about 2.7, about 0.6 to about 2.6, about 0.6 to about 2.5, about 0.6 to about 2.4, about 0.6 to about 2.3, about 0.6 to about 2.2, about 0.6 to about 2.1, about 0.6 to about 2.0, about 0.6 to about 1.9, about 0.6 to about 1.8, about 0.6 to about 1.7, about 0.6 to about 1.6, about 0.6 to about 1.5, about 0.6 to about 1.4, about 0.6 to about 1.3, about 0.6 to about 1.2, about 0.6 to about 1.1, about 0.6 to about 1.0, about 0.7 to about 10, about 0.7 to about 9, about 0.7 to about 8, about 0.7 to about 8, about 0.7 to about 7, about 0.7 to about 6, about 0.7 to about 5, about 0.7 to about 4, about 0.7 to about 3, about 0.7 to about 2.9, about 0.7 to about 2.8, about 0.7 to about 2.7, about 0.7 to about 2.6, about 0.7 to about 2.5, about 0.7 to about 2.4, about 0.7 to about 2.3, about 0.7 to about 2.2, about 0.7 to about 2.1, about 0.7 to about 2.0, about 0.7 to about 1.9, about 0.7 to about 1.8, about 0.7 to about 1.7, about 0.7 to about 1.6, about 0.7 to about 1.5, about 0.7 to about 1.4, about 0.7 to about 1.3, about 0.7 to about 1.2, about 0.7 to about 1.1, about 0.7 to about 1.0, about 0.8 to about 10, about 0.8 to about 9, about 0.8 to about 8, about 0.8 to about 8, about 0.8 to about 7, about 0.8 to about 6, about 0.8 to about 5, about 0.8 to about 4, about 0.8 to about 3, about 0.8 to about 2.9, about 0.8 to about 2.8, about 0.8 to about 2.7, about 0.8 to about 2.6, about 0.8 to about 2.5, about 0.8 to about 2.4, about 0.8 to about 2.3, about 0.8 to about 2.2, about 0.8 to about 2.1, about 0.8 to about 2.0, about 0.8 to about 1.9, about 0.8 to about 1.8, about 0.8 to about 1.7, about 0.8 to about 1.6, about 0.8 to about 1.5, about 0.8 to about 1.4, about 0.8 to about 1.3, about 0.8 to about 1.2, about 0.8 to about 1.1, about 0.8 to about 1.0, about 0.9 to about 10, about 0.9 to about 9, about 0.9 to about 8, about 0.9 to about 8, about 0.9 to about 7, about 0.9 to about 6, about 0.9 to about 5, about 0.9 to about 4, about 0.9 to about 3, about 0.9 to about 2.9, about 0.9 to about 2.8, about 0.9 to about 2.7, about 0.9 to about 2.6, about 0.9 to about 2.5, about 0.9 to about 2.4, about 0.9 to about 2.3, about 0.9 to about 2.2, about 0.9 to about 2.1, about 0.9 to about 2.0, about 0.9 to about 1.9, about 0.9 to about 1.8, about 0.9 to about 1.7, about 0.9 to about 1.6, about 0.9 to about 1.5, about 0.9 to about 1.4, about 0.9 to about 1.3, about 0.9 to about 1.2, about 0.9 to about 1.1, about 0.9 to about 1.0, about 1.0 to about 10, about 1.0 to about 9, about 1.0 to about 8, about 1.0 to about 8, about 1.0 to about 7, about 1.0 to about 6, about 1.0 to about 5, about 1.0 to about 4, about 1.0 to about 3, about 1.0 to about 2.9, about 1.0 to about 2.8, about 1.0 to about 2.7, about 1.0 to about 2.6, about 1.0 to about 2.5, about 1.0 to about 2.4, about 1.0 to about 2.3, about 1.0 to about 2.2, about 1.0 to about 2.1, about 1.0 to about 2.0, about 1.0 to about 1.9, about 1.0 to about 1.8, about 1.0 to about 1.7, about 1.0 to about 1.6, about 1.0 to about 1.5, about 1.0 to about 1.4, about 1.0 to about 1.3, about 1.0 to about 1.2, about 1.0 to about 1.1, about 1.0 to about 1.0; or any subrange within the foregoing ranges; or any set of values within the foregoing ranges.

In a further aspect, with regard to the foregoing reaction, the mol % of catalyst in the reaction can be a suitable mol %, e.g., a mol % of about 0.1 mol %, about 0.2 mol %, about 0.3 mol %, about 0.4 mol %, about 0.5 mol %, about 0.6 mol %, about 0.7 mol %, about 0.8 mol %, about 0.9 mol %, about 1.0 mol %, about 1.1 mol %, about 1.2 mol %, about 1.3 mol %, about 1.4 mol %, about 1.5 mol %, about 1.6 mol %, about 1.7 mol %, about 1.8 mol %, about 1.9 mol %, about 2.0 mol %, about 2.0 mol %, about 2.1 mol %, about 2.2 mol %, about 2.3 mol %, about 2.4 mol %, about 2.5 mol %, about 2.6 mol %, about 2.7 mol %, about 2.8 mol %, about 2.9 mol %, about 3.0 mol %, about 3.1 mol %, about 3.2 mol %, about 3.3 mol %, about 3.4 mol %, about 3.5 mol %, about 3.6 mol %, about 3.7 mol %, about 3.8 mol %, about 3.9 mol %, about 4.0 mol %, about 4.1 mol %, about 4.2 mol %, about 4.3 mol %, about 4.4 mol %, about 4.5 mol %, about 4.6 mol %, about 4.7 mol %, about 4.8 mol %, about 4.9 mol %, about 5.0 mol %, about 5.1 mol %, about 5.2 mol %, about 5.3 mol %, about 5.4 mol %, about 5.5 mol %, about 5.6 mol %, about 5.7 mol %, about 5.8 mol %, about 5.9 mol %, %, about 6 mol %, about 7 mol %, about 8 mol %, about 9 mol %, about 10 mol %; or any range utilizing any two of the foregoing ranges; or any set of values from the foregoing values. In a still further aspect, the mol % of catalyst in the reaction can be from about 0.5 mol % to about 1.5 mol %. In a yet further aspect, the mol % of catalyst in the reaction can be from about 0.7 mol % to about 1.3 mol %. In an even further aspect, the mol % of catalyst in the reaction can be from about 0.9 mol % to about 1.1 mol %. In a still further aspect, the mol % of catalyst in the reaction can be from about 1.0 mol % to about 1.2 mol %.

In a further aspect, with regard to the foregoing reaction, the reaction can be carried out at a suitable reaction temperature, e.g., a temperature of about 0° C., about 1° C., about 2° C., about 3° C., about 4° C., about 5° C., about 6° C., about 7° C., about 8° C., about 9° C., about 11° C., about 12° C., about 13° C., about 14° C., about 15° C., about 16° C., about 17° C., about 18° C., about 19° C., about 21° C., about 22° C., about 23° C., about 24° C., about 25° C., about 26° C., about 27° C., about 28° C., about 29° C., about 31° C., about 32° C., about 33° C., about 34° C., about 35° C., about 36° C., about 37° C., about 38° C., about 39° C., about 41° C., about 42° C., about 43° C., about 44° C., about 45° C., about 46° C., about 47° C., about 48° C., about 49° C., about 50° C.; or any range utilizing any two of the foregoing ranges; or any set of values from the foregoing values. In a still further aspect, the reaction can be carried out at a reaction temperature of from about 15° C. to about 30° C. In a yet further aspect, the reaction can be carried out at a reaction temperature of from about 20° C. to about 30° C. In an even further aspect, the reaction can be carried out at a reaction temperature of from about 22° C. to about 28° C.

In various aspects, the disclosed method of preparing a chiral aziridine derivative can be carried out as shown in the following reaction:

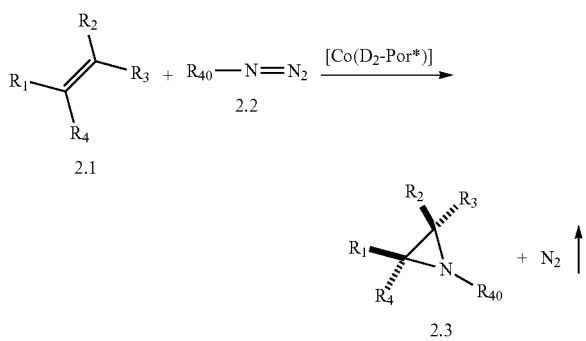

In the foregoing reaction, the following definitions apply to the substituent groups: each of $R_1$, $R_2$, $R_3$, and $R_4$ is independently selected from C1-C10 substituted alkyl, substituted aryl, substituted heteroaryl, substituted cycloalkyl, and substituted heteroalkyl; $R_{40}$ is selected from substituted alkyl, substituted aryl, substituted heteroaryl, substituted cycloalkyl, substituted heteroalkyl; and $R_{60}$—SO2-; $R_{60}$ is selected from $R_{61}$, —N—$R_{61}$, and —O—$R_{61}$; and $R_{61}$ is selected from C1-C10 substituted alkyl, substituted aryl, substituted heteroaryl, substituted cycloalkyl, and substituted heteroalkyl.

In a further aspect, with regard to the foregoing reaction, the molar or equivalent ratio of compound 2.1 to compound 2.2 can be a suitable ratio, e.g., a ratio of from about 0.5 to about 10, about 0.5 to about 9, about 0.5 to about 8, about 0.5 to about 8, about 0.5 to about 7, about 0.5 to about 6, about 0.5 to about 5, about 0.5 to about 4, about 0.5 to about 3, about 0.5 to about 2.9, about 0.5 to about 2.8, about 0.5 to about 2.7, about 0.5 to about 2.6, about 0.5 to about 2.5, about 0.5 to about 2.4, about 0.5 to about 2.3, about 0.5 to about 2.2, about 0.5 to about 2.1, about 0.5 to about 2.0, about 0.5 to about 1.9, about 0.5 to about 1.8, about 0.5 to about 1.7, about 0.5 to about 1.6, about 0.5 to about 1.5, about 0.5 to about 1.4, about 0.5 to about 1.3, about 0.5 to about 1.2, about 0.5 to about 1.1, about 0.5 to about 1.0, about 0.6 to about 10, about 0.6 to about 9, about 0.6 to about 8, about 0.6 to about 8, about 0.6 to about 7, about 0.6 to about 6, about 0.6 to about 5, about 0.6 to about 4, about 0.6 to about 3, about 0.6 to about 2.9, about 0.6 to about 2.8, about 0.6 to about 2.7, about 0.6 to about 2.6, about 0.6 to about 2.5, about 0.6 to about 2.4, about 0.6 to about 2.3, about 0.6 to about 2.2, about 0.6 to about 2.1, about 0.6 to about 2.0, about 0.6 to about 1.9, about 0.6 to about 1.8, about 0.6 to about 1.7, about 0.6 to about 1.6, about 0.6 to about 1.5, about 0.6 to about 1.4, about 0.6 to about 1.3, about 0.6 to about 1.2, about 0.6 to about 1.1, about 0.6 to about 1.0, about 0.7 to about 10, about 0.7 to about 9, about 0.7 to about 8, about 0.7 to about 8, about 0.7 to about 7, about 0.7 to about 6, about 0.7 to about 5, about 0.7 to about 4, about 0.7 to about 3, about 0.7 to about 2.9, about 0.7 to about 2.8, about 0.7 to about 2.7, about 0.7 to about 2.6, about 0.7 to about 2.5, about 0.7 to about 2.4, about 0.7 to about 2.3, about 0.7 to about 2.2, about 0.7 to about 2.1, about 0.7 to about 2.0, about 0.7 to about 1.9, about 0.7 to about 1.8, about 0.7 to about 1.7, about 0.7 to about 1.6, about 0.7 to about 1.5, about 0.7 to about 1.4, about 0.7 to about 1.3, about 0.7 to about 1.2, about 0.7 to about 1.1, about 0.7 to about 1.0, about 0.8 to about 10, about 0.8 to about 9, about 0.8 to about 8, about 0.8 to about 8, about 0.8 to about 7, about 0.8 to about 6, about 0.8 to about 5, about 0.8 to about 4, about 0.8 to about 3, about 0.8 to about 2.9, about 0.8 to about 2.8, about 0.8 to about 2.7, about 0.8 to about 2.6, about 0.8 to about 2.5, about 0.8 to about 2.4, about 0.8 to about 2.3, about 0.8 to about 2.2, about 0.8 to about 2.1, about 0.8 to about 2.0, about 0.8 to about 1.9, about 0.8 to about 1.8, about 0.8 to about 1.7, about 0.8 to about 1.6, about 0.8 to about 1.5, about 0.8 to about 1.4, about 0.8 to about 1.3, about 0.8 to about 1.2, about 0.8 to about 1.1, about 0.8 to about 1.0, about 0.9 to about 10, about 0.9 to about 9, about 0.9 to about 8, about 0.9 to about 8, about 0.9 to about 7, about 0.9 to about 6, about 0.9 to about 5, about 0.9 to about 4, about 0.9 to about 3, about 0.9 to about 2.9, about 0.9 to about 2.8, about 0.9 to about 2.7, about 0.9 to about 2.6, about 0.9 to about 2.5, about 0.9 to about 2.4, about 0.9 to about 2.3, about 0.9 to about 2.2, about 0.9 to about 2.1, about 0.9 to about 2.0, about 0.9 to about 1.9, about 0.9 to about 1.8, about 0.9 to about 1.7, about 0.9 to about 1.6, about 0.9 to about 1.5, about 0.9 to about 1.4, about 0.9 to about 1.3, about 0.9 to about 1.2, about 0.9 to about 1.1, about 0.9 to about 1.0, about 1.0 to about 10, about 1.0 to about 9, about 1.0 to about 8, about 1.0 to about 8, about 1.0 to about 7, about 1.0 to about 6, about 1.0 to about 5, about 1.0 to about 4, about 1.0 to about 3, about 1.0 to about 2.9, about 1.0 to about 2.8, about 1.0 to about 2.7, about 1.0 to about 2.6, about 1.0 to about 2.5, about 1.0 to about 2.4, about 1.0 to about 2.3, about 1.0 to about 2.2, about 1.0 to about 2.1, about 1.0 to about 2.0, about 1.0 to about 1.9, about 1.0 to about 1.8, about 1.0 to about 1.7, about 1.0 to about 1.6, about 1.0 to about 1.5, about 1.0 to about 1.4, about 1.0 to about 1.3, about 1.0 to about 1.2, about 1.0 to about 1.1, about 1.0 to about 1.0; or any subrange within the foregoing ranges; or any set of values within the foregoing ranges.

In a further aspect, with regard to the foregoing reaction, the mol % of catalyst in the reaction can be a suitable mol %, e.g., a mol % of about 0.1 mol %, about 0.2 mol %, about 0.3 mol %, about 0.4 mol %, about 0.5 mol %, about 0.6 mol %, about 0.7 mol %, about 0.8 mol %, about 0.9 mol %, about 1.0 mol %, about 1.1 mol %, about 1.2 mol %, about 1.3 mol %, about 1.4 mol %, about 1.5 mol %, about 1.6 mol %, about 1.7 mol %, about 1.8 mol %, about 1.9 mol %, about 2.0 mol %, about 2.0 mol %, about 2.1 mol %, about 2.2 mol %, about 2.3 mol %, about 2.4 mol %, about 2.5 mol %, about 2.6 mol %, about 2.7 mol %, about 2.8 mol %, about 2.9 mol %, about 3.0 mol %, about 3.1 mol %, about 3.2 mol %, about 3.3 mol %, about 3.4 mol %, about 3.5 mol %, about 3.6 mol %, about 3.7 mol %, about 3.8 mol %, about 3.9 mol %, about 4.0 mol %, about 4.1 mol %, about 4.2 mol %, about 4.3 mol %, about 4.4 mol %, about 4.5 mol %, about 4.6 mol %, about 4.7 mol %, about 4.8 mol %, about 4.9 mol %, about 5.0 mol %, about 5.1 mol %, about 5.2 mol %, about 5.3 mol %, about 5.4 mol %, about 5.5 mol %, about 5.6 mol %, about 5.7 mol %, about 5.8 mol %, about 5.9 mol %, %, about 6 mol %, about 7 mol %, about 8 mol %, about 9 mol %, about 10 mol %; or any range utilizing any two of the foregoing ranges; or any set of values from the foregoing values. In a still further aspect, the mol % of catalyst in the reaction can be from about 0.5 mol % to about 1.5 mol %. In a yet further aspect, the mol % of catalyst in the reaction can be from about 0.7 mol % to about 1.3 mol %. In an even further aspect, the mol % of catalyst in the reaction can be from about 0.9 mol % to about 1.1 mol %. In a still further aspect, the mol % of catalyst in the reaction can be from about 1.0 mol % to about 1.2 mol %.

In a further aspect, with regard to the foregoing reaction, the reaction can be carried out at a suitable reaction temperature, e.g., a temperature of about 0° C., about 1° C., about 2° C., about 3° C., about 4° C., about 5° C., about 6° C., about 7° C., about 8° C., about 9° C., about 11° C., about 12° C., about 13° C., about 14° C., about 15° C., about 16° C., about 17° C., about 18° C., about 19° C., about 21° C., about 22° C., about 23° C., about 24° C., about 25° C., about 26° C., about 27° C., about 28° C., about 29° C., about 31° C., about 32° C., about 33° C., about 34° C., about 35° C., about 36° C., about 37° C., about 38° C., about 39° C., about 41° C., about 42° C., about 43° C., about 44° C., about 45° C., about 46° C., about 47° C., about 48° C., about 49° C., about 50° C.; or any range utilizing any two of the foregoing ranges; or any set of values from the foregoing values. In a still further aspect, the reaction can be carried out at a reaction temperature of from about 0° C. to about 10° C. In a yet further aspect, the reaction can be carried out at a reaction temperature of from about 0° C. to about 5° C. In an even further aspect, the reaction can be carried out at a reaction temperature of from about 1° C. to about 7° C.

REFERENCES

References are cited herein throughout using the format of reference number(s) enclosed by parentheses corresponding to one or more of the following numbered references. For example, citation of references numbers 1 and 2 immediately herein below would be indicated in the disclosure as (1, 2).

1. Boitrel, B et al, J. Chem. Soc., Chem. Commun. 1985, 1820.
2. Boitrel, B et al, Eur. J. Inorg. Chem. 2002, 1666.
3. Bruker (2001b). SAINT-V6.28A. Data Reduction Software.
4. Bruker (2008). APEX2 (Version 2008.1-0). Bruker AXS Inc., Madison, Wis., USA.
5. Carminati, D M et al, Chem. Eur. J. 2016, 22, 13599.
6. Chen, Y et al, J. Am. Chem. Soc. 2004, 126, 14718.
7. Chen, Y et al, J. Am. Chem. Soc. 2007, 129, 12074.
8. Chirila, A et al, ChemCatChem 2017, 9, 1413.
9. Curran, D P et al, Stereochemistry of Radical Reactions: Concepts, Guidelines, and Synthetic Applications; Wiley-VCH: Weinheim, Germany, 2008.
10. Degennaro, L et al, Chem. Rev. 2014, 114, 7881.
11. Denes, F. et al, Chem. Rev. 2014, 114, 2587.
12. Doyle, M P et al, Chem. Rev. 1998, 98, 911.
13. Dzik, W I et al, J. Am. Chem. Soc. 2010, 132, 10891.
14. Even, P et al, Coord. Chem. Rev. 2006, 250, 519.
15. Fantauzzi, S et al, Organometallics 2008, 27, 6143.
16. Farrugia L. J. Appl. Cryst. (1999). 32, 837±838
17. Funken, N et al, Angew. Chem. Int. Ed. 2016, 55, 12030; Angew. Chem. 2016, 128, 12209.

18. Gallo, E et al, Organometallics 2014, 33, 608.

19. Gansauer, A et al, J. Am. Chem. Soc. 2007, 129, 3484.

20. Gansauer, A et al, J. Am. Chem. Soc. 2010, 132, 11858.

21. Hashimoto, T et al, Nat. Chem. 2014, 6, 702.

22. Hildebrandt, S et al, Angew. Chem. Int. Ed. 2016, 55, 9719; Angew. Chem. 2016, 128, 9871.

23. Jiang, H et al, J. Am. Chem. Soc. 2017, 139, 9164.

24. Jin, L-M et al, Angew. Chem. Int. Ed. 2013, 52, 5309; Angew. Chem. 2013, 125, 5417.

25. Karns, AS et al, Chem. Eur. J. 2018, 24, 5253.

26. Kern, N et al., Nat. Chem. 2017, 9, 1198.

27. Lebel, H et al, Chem. Rev. 2003, 103, 977.

28. Lu, H et al, J. Am. Chem. Soc. 2011, 133, 8518.

29. Lu, H J et al, Angew. Chem. Int. Ed. 2010, 49, 10192; Angew. Chem. 2010, 122, 10390.

30. Lyaskovskyy, V et al, J. Am. Chem. Soc. 2011, 133, 12264

31. Meyer, D et al, Angew. Chem. Int. Ed. 2017, 56, 10858.

32. Miyabe, H et al, Chem. Eur. J. 2017, 23, 6225.

33. Morrill, C et al, Angew. Chem. Int. Ed. 2018, 57, 3692; Angew. Chem. 2018, 130, 3754.

34. Muller, P et al., Chem. Rev. 2003, 103, 2905.

35. Pellessier, H et al, Chem. Rev. 2014, 114, 2775.

36. Plesniak, M P et al, Nat. Rev. Chem. 2017, 1, 0077.

37. Raynal, M et al, Chem. Soc. Rev. 2014, 43, 1734.

38. Reddy, A. R. et al, Angew. Chem. Int. Ed. 2016, 55, 1810; Angew. Chem. 2016, 128, 1842.

39. Rose, E et al, Coord. Chem. Rev. 1998, 178, 1407.

40. Roy, S et al, Angew. Chem. Int. Ed. 2018, 57, 2238; Angew. Chem. 2018, 130, 2260.

41. Sheldrick, G. M. (1996). SADABS. Program for Empirical Absorption Correction. University of Gottingen, Germany.

42. Sheldrick, G. M. (2008). Acta Cryst. A64, 112-122.

43. Sheldrick, G. M. (1990) Acta Cryst. A46, 467-473

44. Sheldrick, G. M. (1997) SHELXL-97. Program for the Refinement of Crystal

45. Sibi, M P et al, Chem. Rev. 2003, 103, 3263; e) C. Ollivier, P. Renaud, Chem. Rev. 2001, 101, 3415.

46. Studer, A et al, Angew. Chem. Int. Ed. 2016, 55, 58; Angew. Chem. 2016, 128, 58.

47. Subbarayan, V et al, Chem. Commun. 2009, 4266.

48. Villanueva, O et al, Chem. Sci. 2015, 6, 6672.

49. Wang, Y et al, J. Am. Chem. Soc. 2017, 139, 1049.

50. Wang, Y et al, J. Am. Chem. Soc. 2018. 140, 4792.

51. Xu, X et al, J. Am. Chem. Soc. 2011, 133, 15292.

52. Zhang, W et al, Science 2016, 353, 1014.

53. Zhang, Y-Q et al, Angew. Chem. Int. Ed. 2017, 56, 12654; Angew. Chem. 2017, 129, 12828.

54. Zhu, S et al, J. Am. Chem. Soc. 2008, 130, 5042.

ASPECTS

Aspect 1. A catalyst for the synthesis of chiral cyclopropane derivatives and chiral aziridine derivatives, the catalyst comprising Formula I:

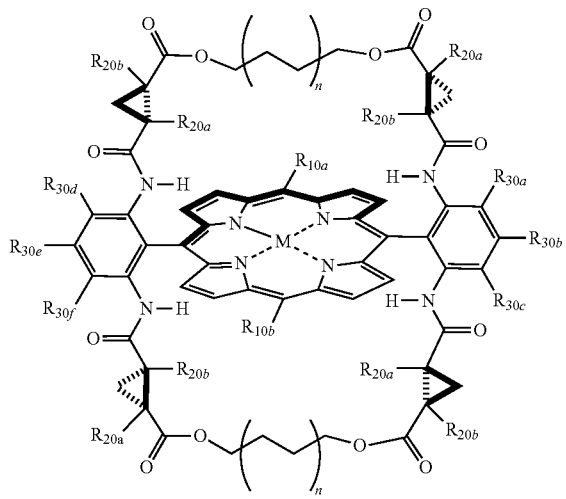

Formula I wherein each of $R_{10a}$ and $R_{10b}$ is independently an aryl group independently substituted with 1, 2, 3, 4, or 5 groups selected from halogen, hydroxy, amino, and C1-C10 alkyl; wherein each occurrence of $R_{20a}$ and $R_{20b}$ is independently substituted with hydrogen and C1-C3 alkyl; wherein each of $R_{30a}$, $R_{30b}$, $R_{30c}$, $R_{30d}$, $R_{30e}$, and $R_{30f}$ is independently selected from hydrogen, hydroxy, amino, and C1-C10 alkyl; and wherein n is selected from 0, 1, 2, 3, 4, 5, 6, 7, 8, 9, 10, 11, 12, 13, 14, 15, 16, 17, 18, 19, and 20.

Aspect 2. The catalyst of aspect 1, wherein stereocenters in the catalyst have the (R) configuration.

Aspect 3. The catalyst of aspect 1 or 2, wherein M comprises cobalt, zinc, aluminum, magnesium, nickel, copper, manganese, iron, germanium, tin, molybdenum, ruthenium, or a combination thereof.

Aspect 4. The catalyst of any of aspects 1-3, wherein M comprises cobalt.

Aspect 5. The catalyst of any of aspects 1-4, wherein n is from 1 to 4.

Aspect 6. The catalyst of any of aspects 1-4, wherein n is 1.

Aspect 7. The catalyst of any of aspects 1-4, wherein n is 2.

Aspect 8. A method for the stereoselective synthesis of a chiral cyclopropane derivative, the method comprising contacting a diazo substrate and a vinyl-containing substrate with the catalyst of any of aspects 1-7 in a solvent.

Aspect 9. The method of aspect 8, wherein the solvent comprises toluene, chlorobenzene, or a combination thereof.

Aspect 10. The method of aspect 8 or 9, wherein the method is conducted at room temperature.

Aspect 11. The method of any of aspects 8-10, wherein the method is conducted under an inert atmosphere.

Aspect 12. The method of aspect 11, wherein the inert atmosphere comprises nitrogen gas.

Aspect 13. The method of any of aspects 8-12, wherein the diazo substrate comprises ethyl diazoacetate.

Aspect 14. The method of any of aspects 8-13, wherein the vinyl-containing substrate comprises styrene.

Aspect 15. The method of any of aspects 8-14, wherein the chiral cyclopropane derivative comprises a structure of Formula III:

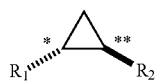

Formula III

Aspect 16. The method of aspect 15, wherein the structure of Formula II comprises:

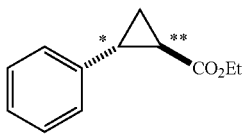 [SMILES: CCOC(=O)[C@@H]1C[C@H]1c1ccccc1]

Aspect 17. The method of aspect 15 or 16, wherein the ratio of (R) enantiomer at * to (S) enantiomer at * is from about 5:95 to about 95:5.

Aspect 18. The method of aspect 15 or 16, wherein the ratio of (R) enantiomer at * to (S) enantiomer at * is from about 15:85 to about 85:15.

Aspect 19. The method of aspect 15 or 16, wherein the ratio of (R) enantiomer at * to (S) enantiomer at * is from about 35:65 to about 65:35.

Aspect 20. The method of aspect 15 or 16, wherein the ratio of (R) enantiomer at  to (S) enantiomer at  is from about 5:95 to about 95:5.

Aspect 21. The method of aspect 15 or 16, wherein the ratio of (R) enantiomer at  to (S) enantiomer at  is from about 15:85 to about 85:15.

Aspect 22. The method of aspect 15 or 16, wherein the ratio of (R) enantiomer at  to (S) enantiomer at  is from about 35:65 to about 65:35.

Aspect 23. The method of aspect 15 or 16, wherein the chiral cyclopropane derivative comprises a mixture of diastereomers and wherein the mixture of diastereomers comprises at least 80% of a compound having (R) configuration at * and **.

Aspect 24. The method of aspect 15 or 16, wherein the chiral cyclopropane derivative comprises a mixture of diastereomers and wherein the mixture of diastereomers comprises at least 85% of a compound having (R) configuration at * and **.

Aspect 25. The method of aspect 15 or 16, wherein the chiral cyclopropane derivative comprises a mixture of diastereomers and wherein the mixture of diastereomers comprises at least 90% of a compound having (R) configuration at * and **.

Aspect 26. A method for the stereoselective synthesis of a chiral aziridine derivative, the method comprising contacting an azido-containing substrate and a vinyl-containing substrate with the catalyst of any of aspects 1-7 in a solvent.

Aspect 27. The method of aspect 26, wherein the solvent comprises toluene, chlorobenzene, or a combination thereof.

Aspect 28. The method of aspect 26 or 27, wherein the method is conducted at 0° C.

Aspect 29. The method of any of aspects 26-28, wherein the method is conducted under an inert atmosphere.

Aspect 30. The method of aspect 29, wherein the inert atmosphere comprises nitrogen gas.

Aspect 31. The method of any of aspects 26-30, wherein the azido-containing substrate comprises trichloroethoxysulfonyl azide.

Aspect 32. The method of any of aspects 26-31, wherein the vinyl-containing substrate comprises styrene.

Aspect 33. The method of any of aspects 26-32, wherein the chiral aziridine derivative comprises a structure of Formula III:

Formula IV wherein $R_{300}$ is C1-C10 substituted alkyl, substituted aryl, substituted heteroaryl, substituted cycloalkyl, and substituted heteroalkyl; wherein $R_{400}$ is $-(C=O)R_{40}$; wherein $R_{40}$ is selected from substituted alkyl, substituted aryl, substituted heteroaryl, substituted cycloalkyl, and substituted heteroalkyl, $-NR_{41}R_{42}$, $-OR_{41}$, $-SR_{41}$; and herein each of $R_{41}$ and $R_{42}$ is independently selected from hydrogen, substituted alkyl, substituted aryl, substituted heteroaryl, substituted cycloalkyl, and substituted heteroalkyl.

Aspect 34. The method of aspect 33, wherein the structure of Formula IV comprises:

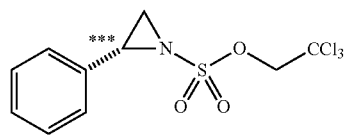

Aspect 35. The method of aspect 33 or 34, wherein the ratio of (R) enantiomer at * to (S) enantiomer at * is from about 5:95 to about 95:5.

Aspect 36. The method of aspect 33 or 34, wherein the ratio of (R) enantiomer at * to (S) enantiomer at * is from about 15:85 to about 85:15.

Aspect 37. The method of aspect 33 or 34, wherein the ratio of (R) enantiomer at * to (S) enantiomer at * is from about 35:65 to about 65:35.

Aspect 38. A composition comprising a chiral cyclopropane derivative produced by the method of any of aspects 8 to 25.

Aspect 39. A composition comprising a chiral aziridine derivative produced by the method of any of aspects 26 to 37.

Now having described the aspects of the present disclosure, in general, the following Examples describe some additional aspects of the present disclosure. While aspects of the present disclosure are described in connection with the following examples and the corresponding text and figures, there is no intent to limit aspects of the present disclosure to this description. On the contrary, the intent is to cover all alternatives, modifications, and equivalents included within the spirit and scope of the present disclosure.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the disclosure and are not intended to limit the scope of what the inventors regard as their disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Example 1: General Synthesis and Characterization Conditions

All catalytic reactions were performed under nitrogen in oven-dried glassware following standard Schlenk techniques. Tetrahydrofuran (THF) and toluene were distilled under nitrogen with sodium benzophenone ketyl. Anhydrous cobalt(II) chloride, palladium(II) acetate, and 9-dimethyl-4, 5-bis(diphenylphosphino) xanthenes (Xantphos) were purchased from Strem Chemical Co. Cesium carbonate was obtained from Chemetall Chemical Products, Inc. Thin layer chromatography was performed on SorBent Tech. TLC plates (silica gel 60 F254). Flash column chromatography was performed with SorBent Tech. silica gel (60 Å, 230-400 mesh, 32-63 μm). $^1$H NMR and $^{13}$C NMR were recorded on a Varian Inova400 (400 MHz) or Bruker500 (500 MHz) and referenced with respect to internal TMS standard. HPLC measurements were carried out on a Shimadzu HPLC system with Chiralcel OD-H, and OJ-H columns. HRMS data was obtained on an Agilent 1100 LC/MS ESI/TOF mass spectrometer with electrospray ionization. Note on Safety: sulfonyl azides used in this work were stable under the conditions used, but it should be noted that azide compounds may be explosive and should be handled with great care.

Example 2: Representative Procedure for 3,5-Di$^t$Bu-($^t$Bu)TaoPhyrin Synthesis

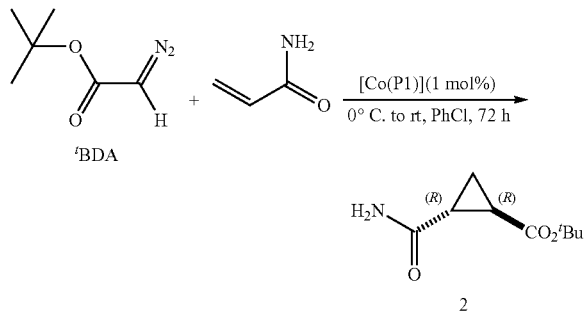

(1R,2R)-tert-butyl 2-carbamoylcyclopropanecarboxylate (2) was synthesized according to a previously published procedure. (S)-[Co(3,5-di$^t$Bu-ChenPhyrin)]([Co(P1)]) (200 mg, 0.15 mmol, 0.01 equiv), acryl amide (5.3 g, 75 mmol, 5 equiv) and DMAP (915 mg, 7.5 mmol, 0.5 equiv) were placed in an oven dried, resealable Schlenk tube. The tube was capped with a Teflon screw cap, evacuated, and back-filled with nitrogen. The screw cap was replaced with a rubber septum. Chlorobenzene (50 mL) was added via syringe. After the solution was cooled to 0° C., tBDA (2.2 mL, 15 mmol, 1 equiv) was added dropwise followed by the addition of 10 mL of chlorobenzene. The tube was purged with nitrogen for 1 min and sealed with a Teflon screw cap. The reaction mixture was warmed up to r.t. and stirred for three days. After the reaction finished, the resulting mixture was purified by flash silica gel chromatography (eluent: Hexanes/EtOAc 3:1) to give the title compound (1.80 g, 65%) in 98% ee. The following recrystallization gave >99% ee; TLC R$_f$=0.25 (Hexanes/EtOAc 3:1). Known compound. $^1$H NMR (400 MHz, CDCl$_3$ ppm 5.84 (s, 1H), 5.76 (s, 1H), 2.07 (ddd, J=9.5, 5.8, 3.8 Hz, 1H), 1.93 (ddd, J=9.4, 5.7, 3.8 Hz, 1H), 1.44 (s, 9H), 1.38 (ddd, J=9.3, 5.7, 3.7 Hz, 1H), 1.28 (ddd, J=9.4, 5.8, 3.7 Hz, 1H); GC (DCB, 5° C./min): Major t=12.95 min., Minor t=11.77 min. (Note: To build up enough materials, multiple runs were conducted.)

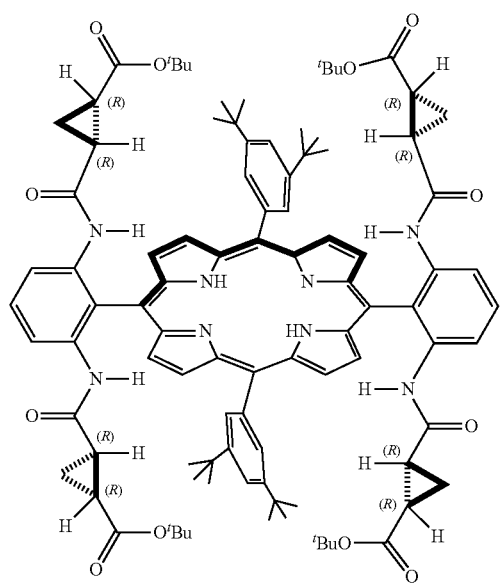

Figure 11A:
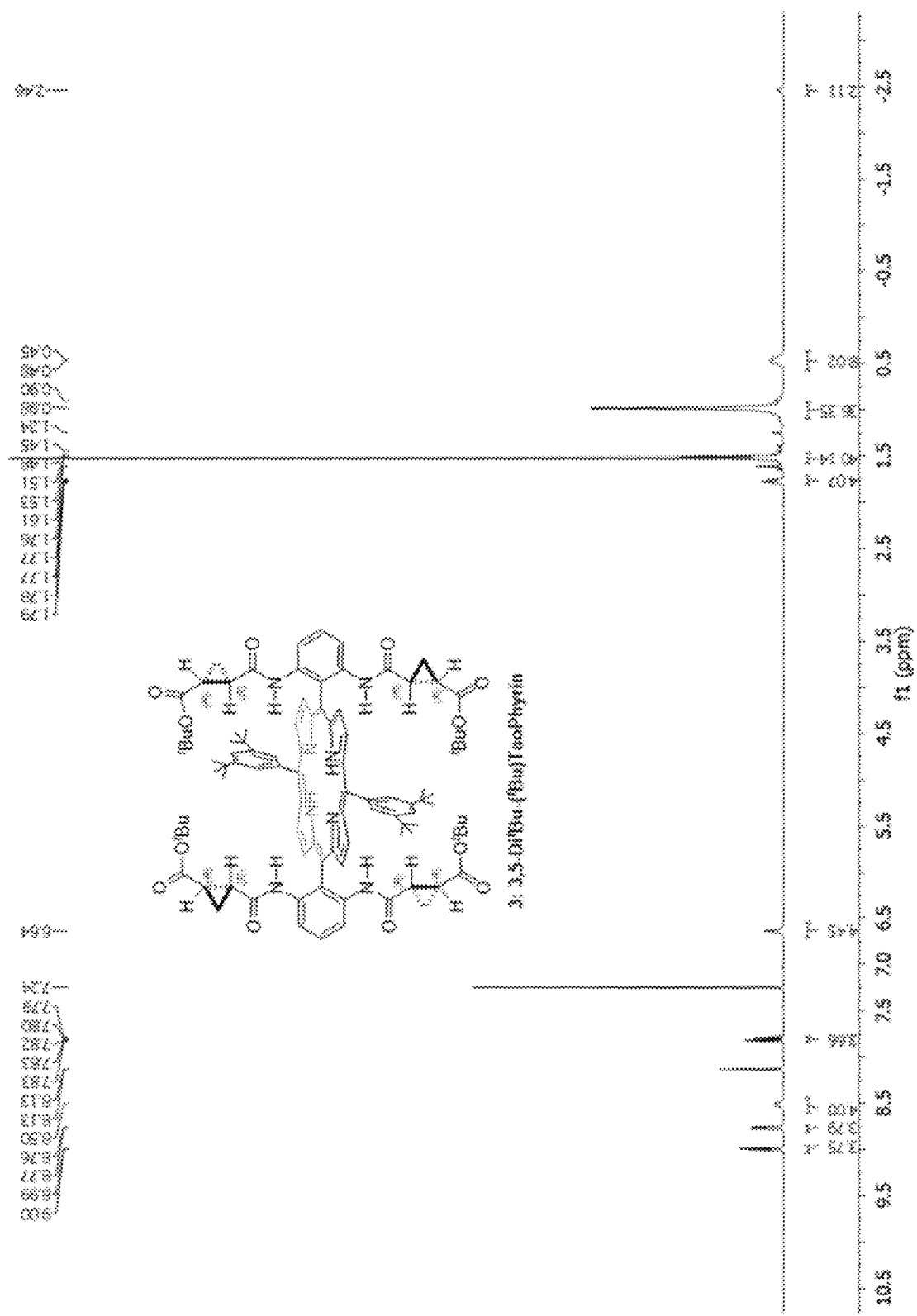
FIGS. 11A and 11B show, respectively, $^1$H and $^{13}$C NMR spectra for 3,5-di$^t$bu-($^t$bu)TaoPhyrin (compound 3).
Figure 11B:
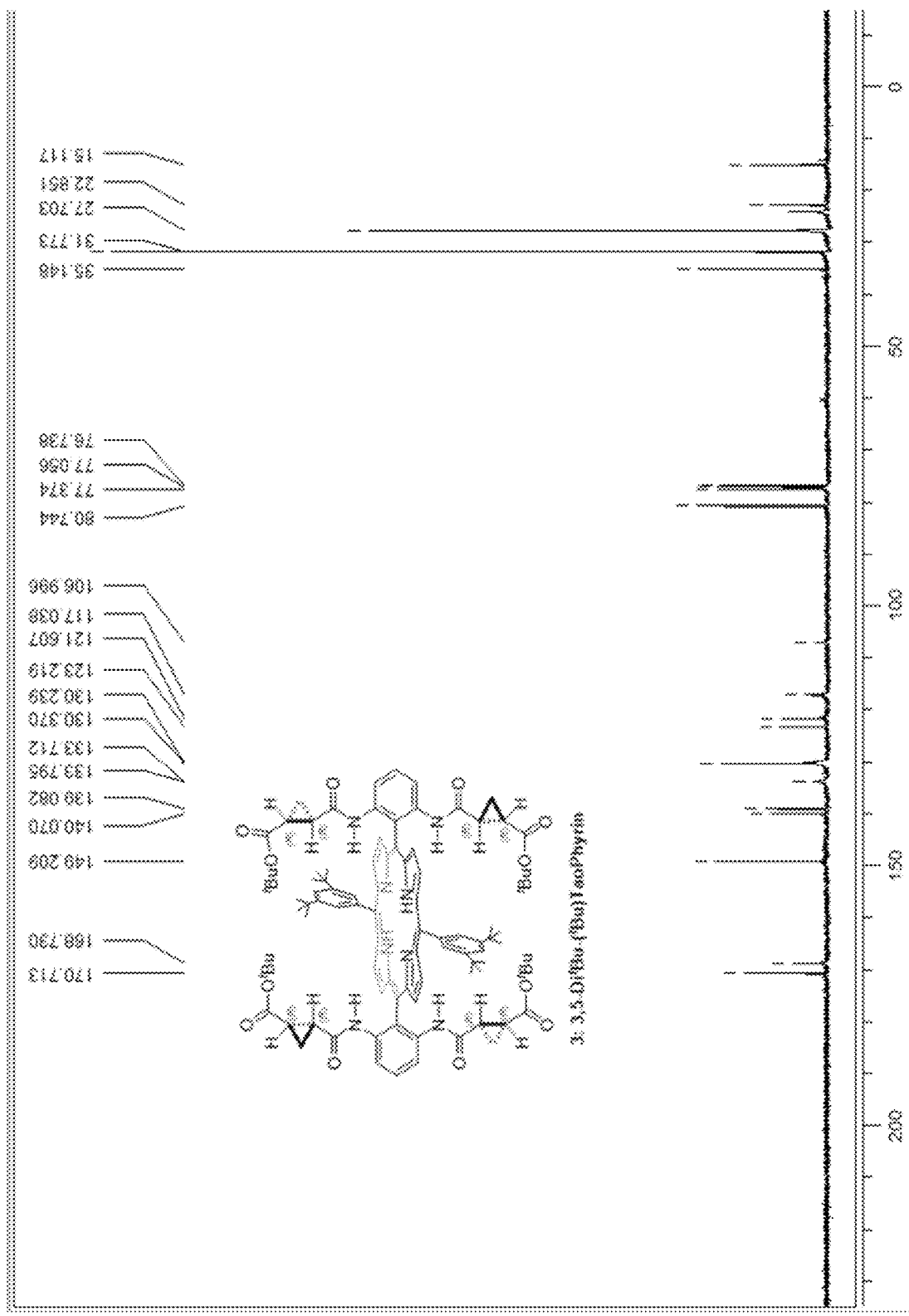

3,5-Di$^t$Bu-($^t$Bu)TaoPhyrin (3) was synthesized according to a previously reported procedure. 3,5-DitBu-Bromosynthon (686 mg, 0.59 mmol, 1 equiv), the above prepared chiral amide 2 (1.76 g, 9.5 mmol, 16 equiv), Pd(OAc)$_2$ (53 mg, 0.236 mmol, 0.4 equiv), Xantphos (274 mg, 0.47 mmol, 0.8 equiv) and Cs$_2$CO$_3$ (3.1 g, 9.5 mmol, 16 equiv) were placed in an oven dried, resealable Schlenk tube. The tube was capped with a Teflon screw cap, evacuated, and back-filled with nitrogen. The screw cap was replaced with a rubber septum. Dioxane (60 mL) was added via syringe and the tube was purged with nitrogen for 1 min and sealed with a Teflon screw cap. The reaction mixture was stirred at 100° C. for three days prior to being cooled to r.t. The reaction mixture was filtered through a short pad of Celite. The solvent was removed and the residue was purified by flash silica gel chromatography (eluent: Hexanes/EtOAc 3:1) to give the title compound (820 mg, 88%); TLC Rf=0.35 (Hexanes/EtOAc 4:1). $^1$H NMR (500 MHz, CDCl$_3$) δ ppm 8.99 (d, J=4.7 Hz, 4H), 8.76 (d, J=4.7 Hz, 4H), 8.50 (s, 4H), 8.13 (d, J=1.6 Hz, 4H), 7.89-7.75 (m, 4H), 6.64 (s, 4H), 1.82-1.74 (m, 4H), 1.53 (s, 36H), 1.51-1.47 (m, 4H), 0.98 (s, 36H), 0.49-0.42 (m, 8H), −2.46 (s, 2H). $^{13}$C NMR (100 MHz, CDCl$_3$) δ ppm 170.7, 168.7, 149.2, 140.1, 139.1, 133.8, 133.7, 133.6, 130.4, 130.2, 123.2, 121.6, 117.0, 107.0, 80.7, 35.1, 31.8, 27.7, 24.1, 22.8, 15.1; HRMS (ESI) ([M+Na]$^+$) Calcd. for 1593.8448, Found 1593.8510. UV-vis (CHCl$_3$), λ$_{max}$ nm (log ε): 421 (5.27), 517 (4.77), 552 (4.37), 592 (4.27), 648 (4.18). (See also FIGS. 11A-11B.)

Example 3: General Procedure A (Transesterification)

TFA (100.0 equiv) was added to a solution of 3,5-Di$^t$Bu-$^t$BuOTaoPhyrin 3 (1.0 equiv) in DCM (0.5 M) and the reaction mixture was stirred overnight prior to the evaporation of all the volatiles. The residue was dissolved in DMF (0.1 M), followed by the addition of powdered K$_2$CO$_3$ (100.0 equiv) and then followed by the addition of alkylating reagents (16.0 equiv). The reaction mixture was heated at 100° C. for 12 h. After cooling to rt, the reaction mixture was diluted with EtOAc and water. The organic layer was separated and washed with brine five times. The organic solvent was removed under vacuum and the resulting oil was then purified by flash column chromatography (eluent: Hexanes/EtOAc 3:1) to afford the pure title compound.

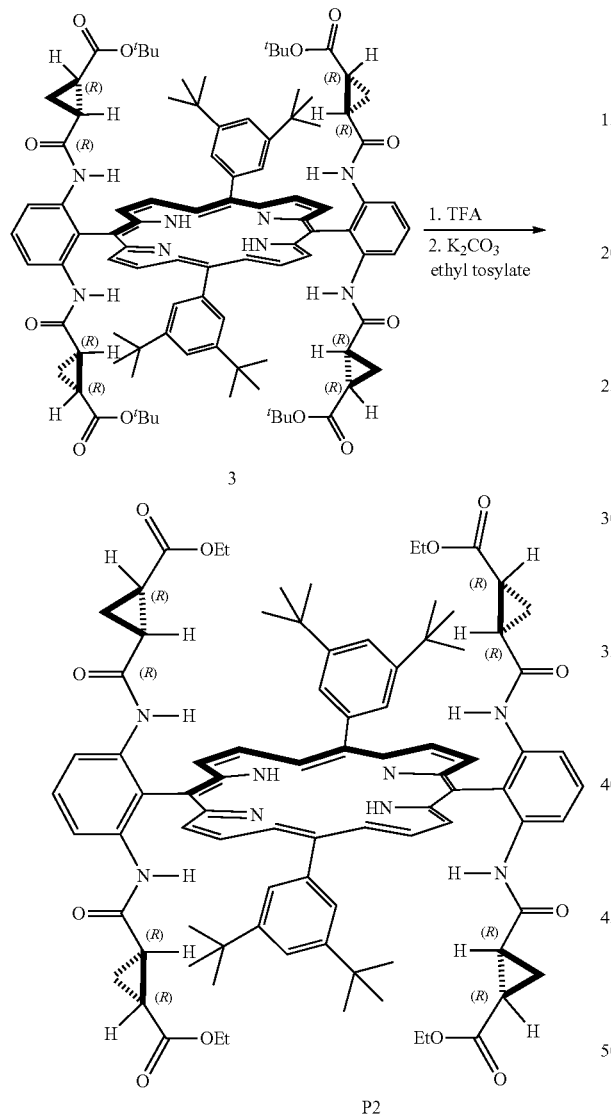

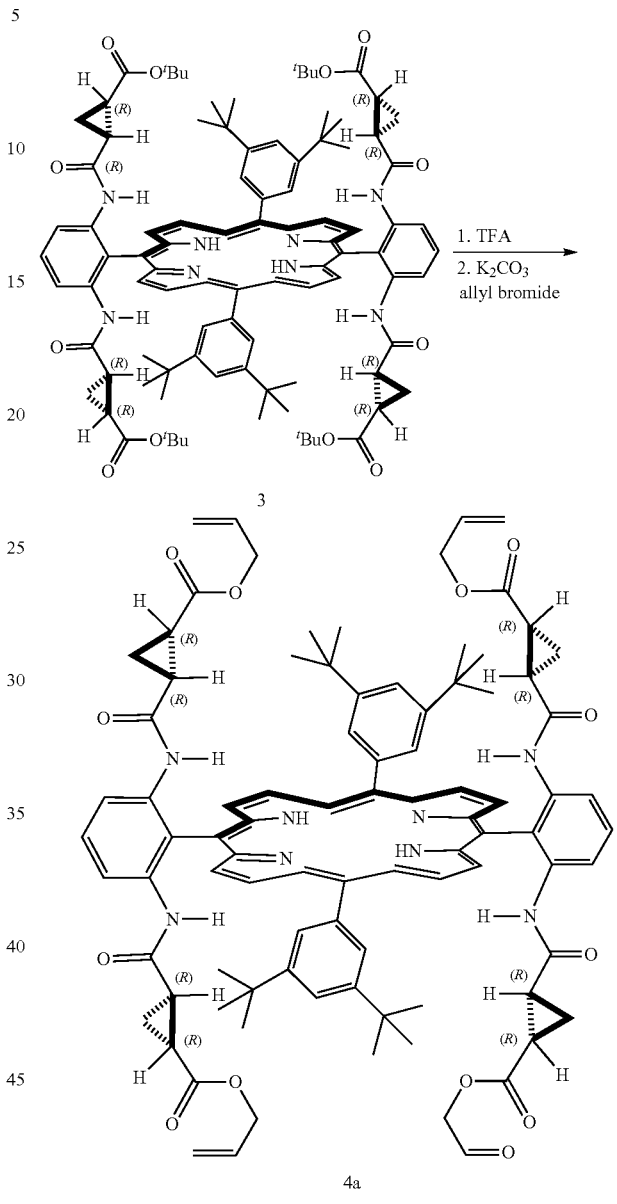

Figure 12A:
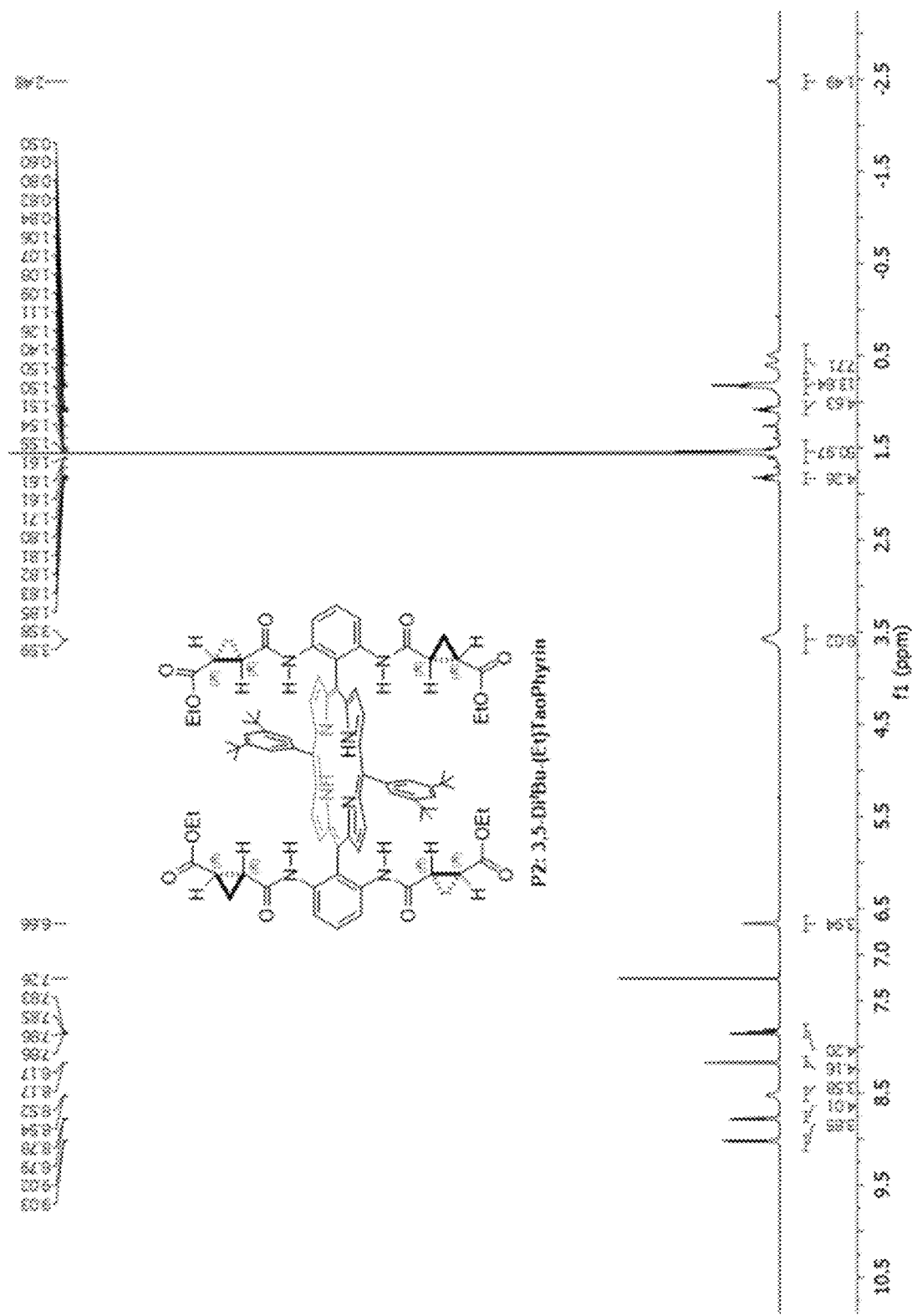
FIGS. 12A and 12B show, respectively, $^1$H and $^{13}$C NMR spectra for 3,5-di$^t$bu-(Et)TaoPhyrin (P2).
Figure 12B:
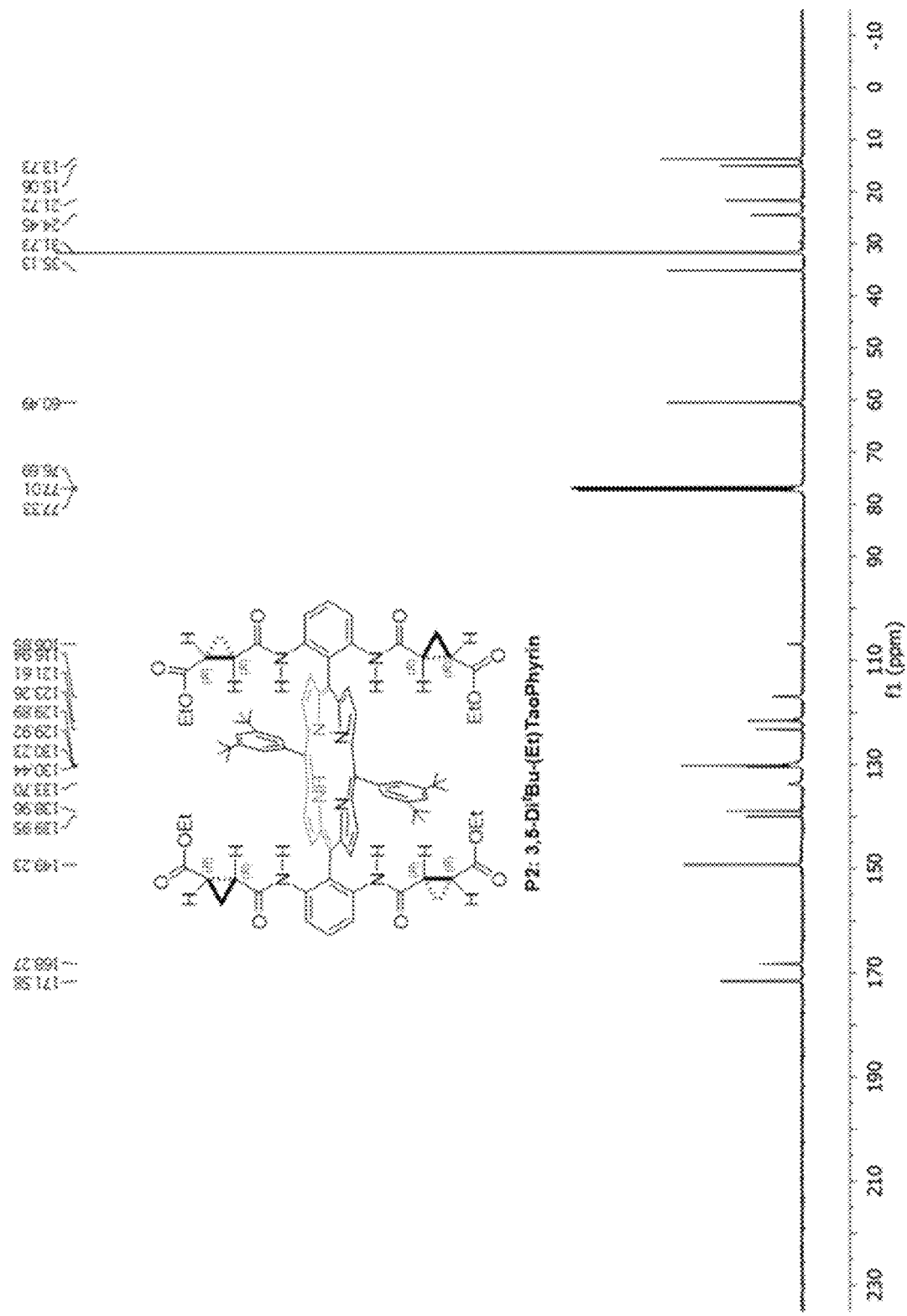

3,5-Di$^t$Bu-(Et)TaoPhyrin (P2) was synthesized following General Procedure A using ethyl 4-methylbenzenesulfonate as the alkylating reagent. (60 mg, 82% yield); TLC $R_f$=0.35 (Hexanes/EtOAc 4:1). $^1$H NMR (400 MHz, CDCl$_3$) δ ppm 9.02 (d, J=4.8 Hz, 4H), 8.78 (d, J=4.8 Hz, 4H), 8.53 (d, J=7.1 Hz, 4H), 8.17 (d, J=1.6 Hz, 4H), 7.86-7.83 (m, 4H), 6.66 (s, 4H), 3.58 (d, J=7.3 Hz, 8H), 1.87-1.78 (m, 4H), 1.55 (s, 36H), 1.13-1.03 (m, 4H), 0.82 (t, J=7.0 Hz, 12H), 0.59-0.56 (m, 4H), 0.52-0.48 (m, 4H), −2.48 (s, 2H); $^{13}$C NMR (100 MHz, CDCl$_3$) δ ppm 171.6, 168.3, 149.2, 139.9, 138.9, 133.7, 133.7, 130.4, 130.2, 129.9, 129.9, 123.3, 121.6, 121.2, 116.9, 106.8, 60.5, 35.1, 31.7, 24.4, 21.7, 15.1, 13.7; HRMS (ESI) ([M+Na]$^+$) Calcd. for: 1481.7202, Found 1481.7228. UV-vis (CHCl$_3$), λ$_{max}$ nm (log ε): 421 (5.20), 515 (4.19), 548 (3.58), 588 (3.65), 644 (3.40). (See also FIGS. 12A-12B.)

Figure 13A:
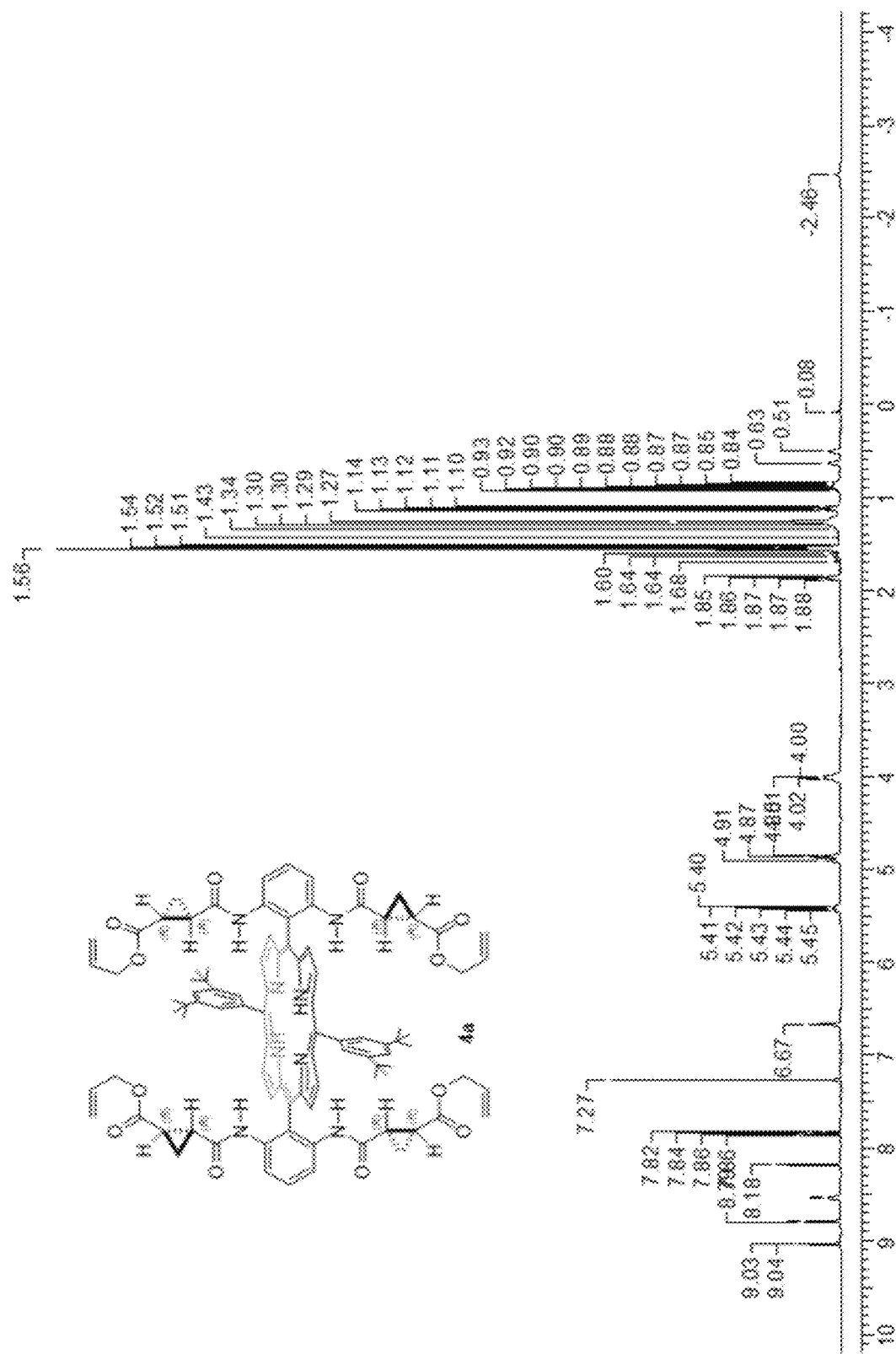
Figure 13B:
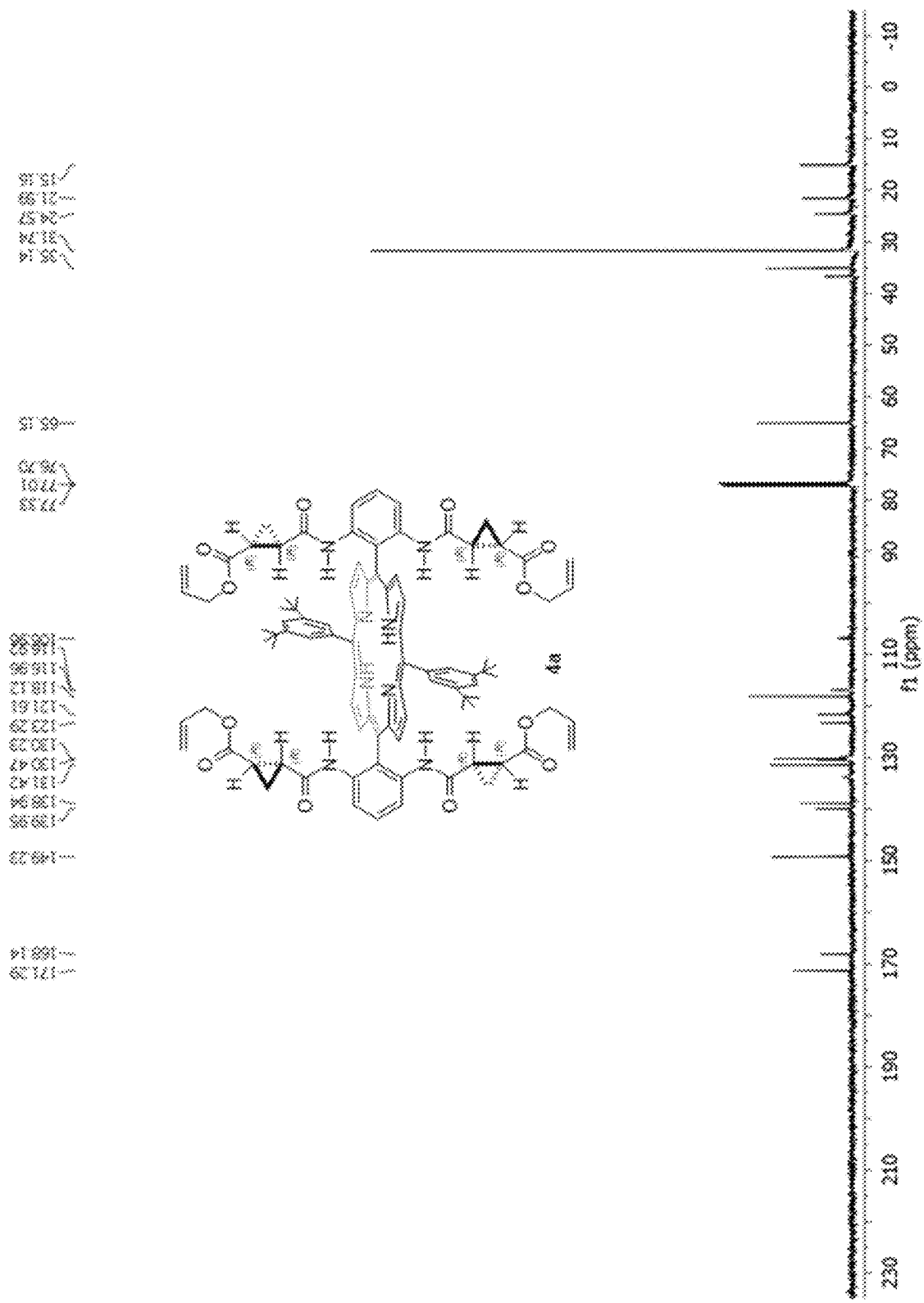

Ester porphyrin 4a was synthesized following General Procedure A using allyl bromide as the alkylating reagent. (241 mg, 80% yield); TLC $R_f$=0.35 (Hexanes/EtOAc 4:1). $^1$H NMR (500 MHz, CDCl$_3$) δ ppm 9.09 (d, J=4.6 Hz, 4H), 8.84 (d, J=4.6 Hz, 4H), 8.59 (d, J=8.1 Hz, 4H), 8.23 (d, J=1.7 Hz, 4H), 7.97-7.85 (m, 4H), 6.74 (br. s., 4H), 5.53-5.37 (m, 4H), 5.01-4.82 (m, 8H), 4.03 (dd, J=4.6, 15.0 Hz, 8H), 1.93-1.85 (m, 4H), 1.56 (s, 36H), 1.18-1.11 (m, 4H), 0.65 (br. s., 4H), 0.56 (br. s., 4H), −2.42 (s, 2H); $^{13}$C NMR (100 MHz, CDCl$_3$) δ ppm 171.3, 168.1, 149.2, 139.9, 138.9, 133.7, 133.7, 133.6, 131.4, 130.5, 130.2, 123.3, 121.6, 118.1, 116.9, 116.9, 106.9, 65.1, 35.1, 31.7, 24.5, 21.6, 15.2. HRMS (ESI) ([M+Na]$^+$) Calcd. for: 1529.7202, Found 1529.7243. UV-vis (CHCl$_3$), λ$_{max}$ nm (log ε): 420 (5.65), 515 (4.31), 548 (3.76), 590 (3.81), 646 (3.41). (See also FIGS. 13A-13B.)

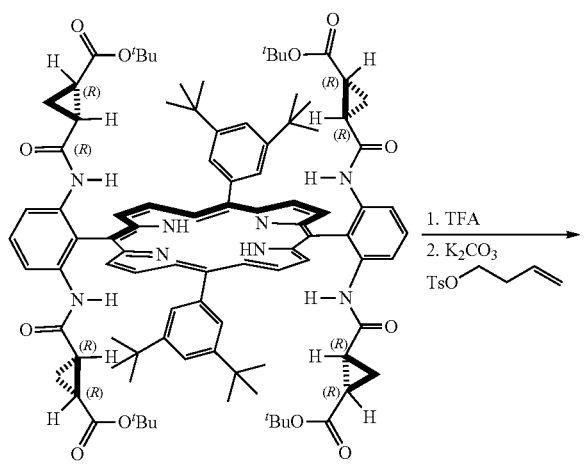

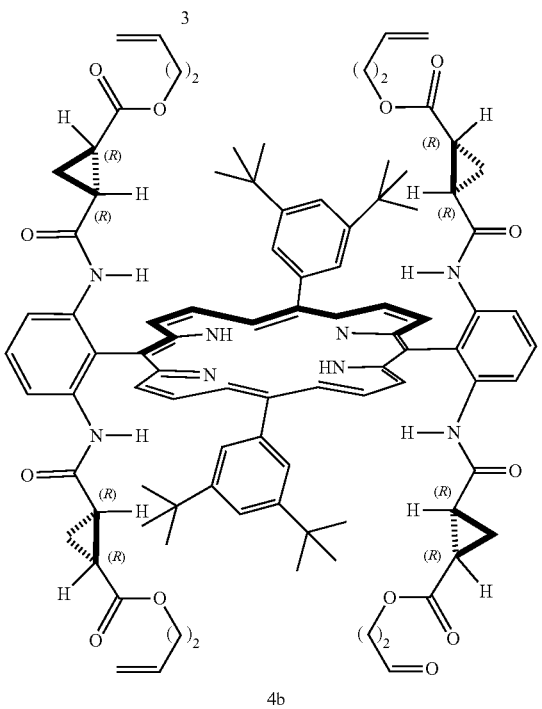

4b

Figure 14A:
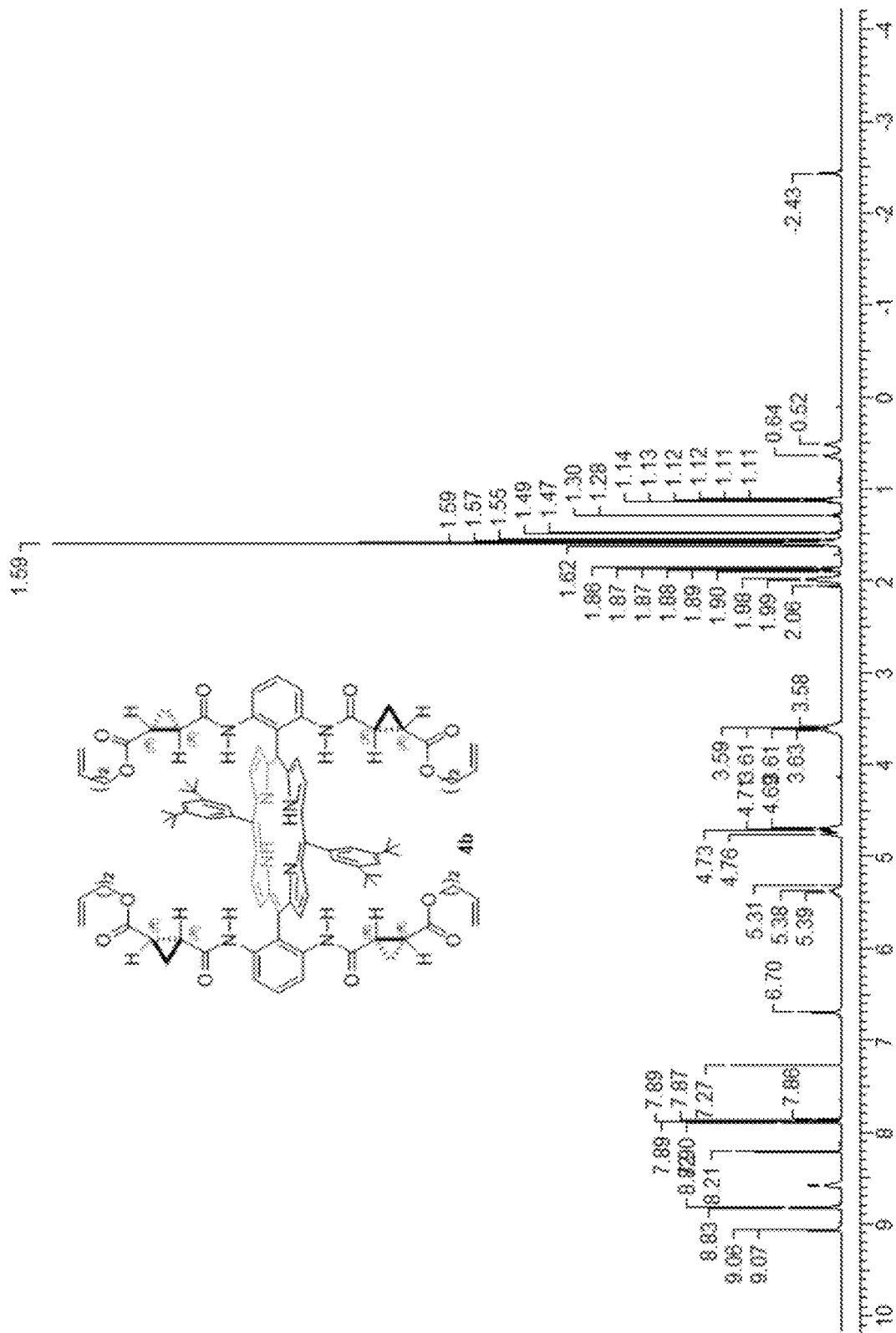
FIGS. 14A and 14B show, respectively, $^1$H and $^{13}$C NMR spectra for compound 4b.
Figure 14B:
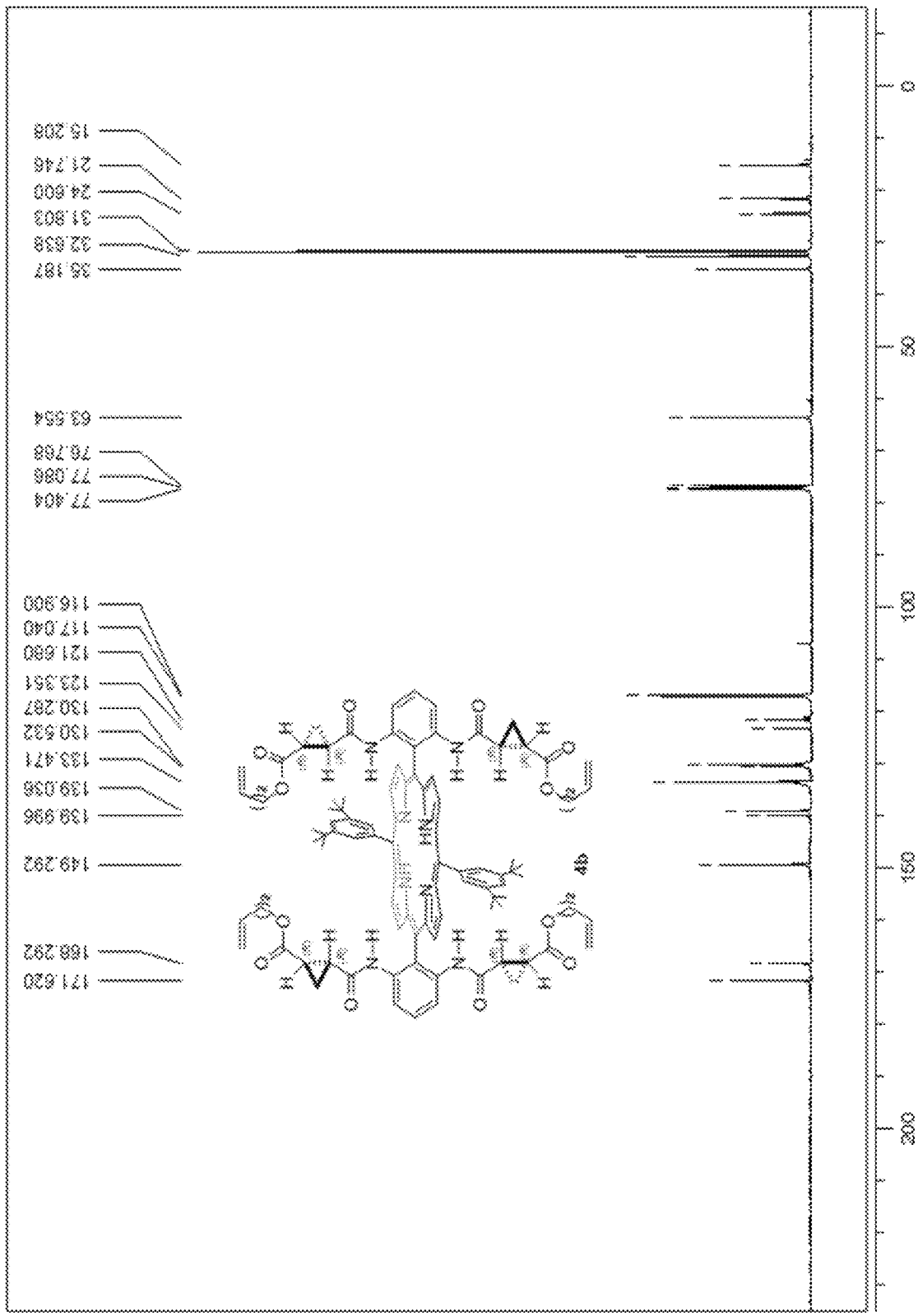

Ester porphyrin 4b was synthesized following General Procedure A using but-3-en-1-yl 4-methylbenzenesulfonate as the alkylating reagent. (280 mg, 89% yield); TLC $R_f$=0.35 (Hexanes/EtOAc 4:1). $^1$H NMR (500 MHz, CDCl$_3$) δ ppm 9.07 (d, J=4.6 Hz, 4H), 8.83 (d, J=5.2 Hz, 4H), 8.63-8.55 (m, 4H), 8.21 (d, J=1.7 Hz, 4H), 7.90 (t, J=2.0 Hz, 2H), 7.87 (t, J=8.7 Hz, 2H), 6.70 (s, 4H), 5.44-5.33 (m, 4H), 4.80-4.66 (m, 8H), 3.83-3.47 (m, 8H), 2.18-1.95 (m, 8H), 1.88 (ddd, J=3.8, 5.3, 8.8 Hz, 4H), 1.59 (s, 36H), 1.12 (ddd, J=4.0, 5.5, 9.0 Hz, 4H), 0.69-0.60 (m, 4H), 0.56-0.47 (m, 4H), −2.43 (s, 2H); $^{13}$C NMR (100 MHz, CDCl$_3$) δ ppm 171.6, 168.3, 149.3, 140.0, 139.0, 133.5, 130.5, 130.3, 123.4, 121.7, 117.0, 116.9, 63.5, 35.2, 32.6, 31.8, 24.6, 21.7, 15.2; HRMS (ESI) ([M+Na]$^+$) Calcd. for: 1585.7828, Found 1585.7854. UV-vis (CHCl$_3$), $\lambda_{max}$ nm (log ε): 421 (5.66), 516 (4.30), 551 (3.81), 592 (3.80), 647 (3.47). (See also FIGS. 14A-14B.)

Example 4: General Procedure B (Ring-Closing Reactions)

Grubbs 2nd generation catalyst (0.1 equiv) was added to a solution of above ester porphyrin (1.0 equiv) in DCM (0.001 M) and the reaction mixture was stirred 12 h at 40° C. The reaction mixture was directly poured onto a pad of silica gel (Hexanes/EtOAc 1:1) to afford the mixture of trans-cis isomers, which was in turn dissolved in EtOAc-toluene (V/V 2/1, 0.02 M) in the presence of 10% Pd/C (1 mg per mg of porphyrin). Hydrogen gas was bubbled through the reaction mixture for about 10 to 20 min until the reaction is completed based on the crude $^1$H NMR. The reaction mixture was filtered, the solvent was removed under vacuum, and the resulting oil was then purified by flash column chromatography (Hexanes/EtOAc 1:1) to afford pure product.

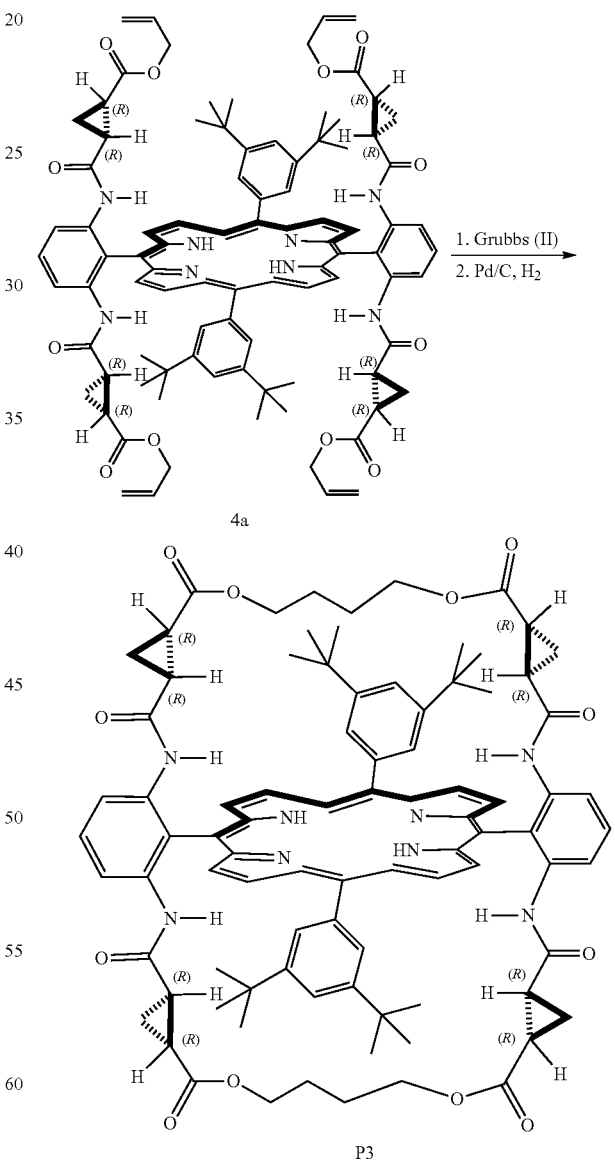

Figure 15A:
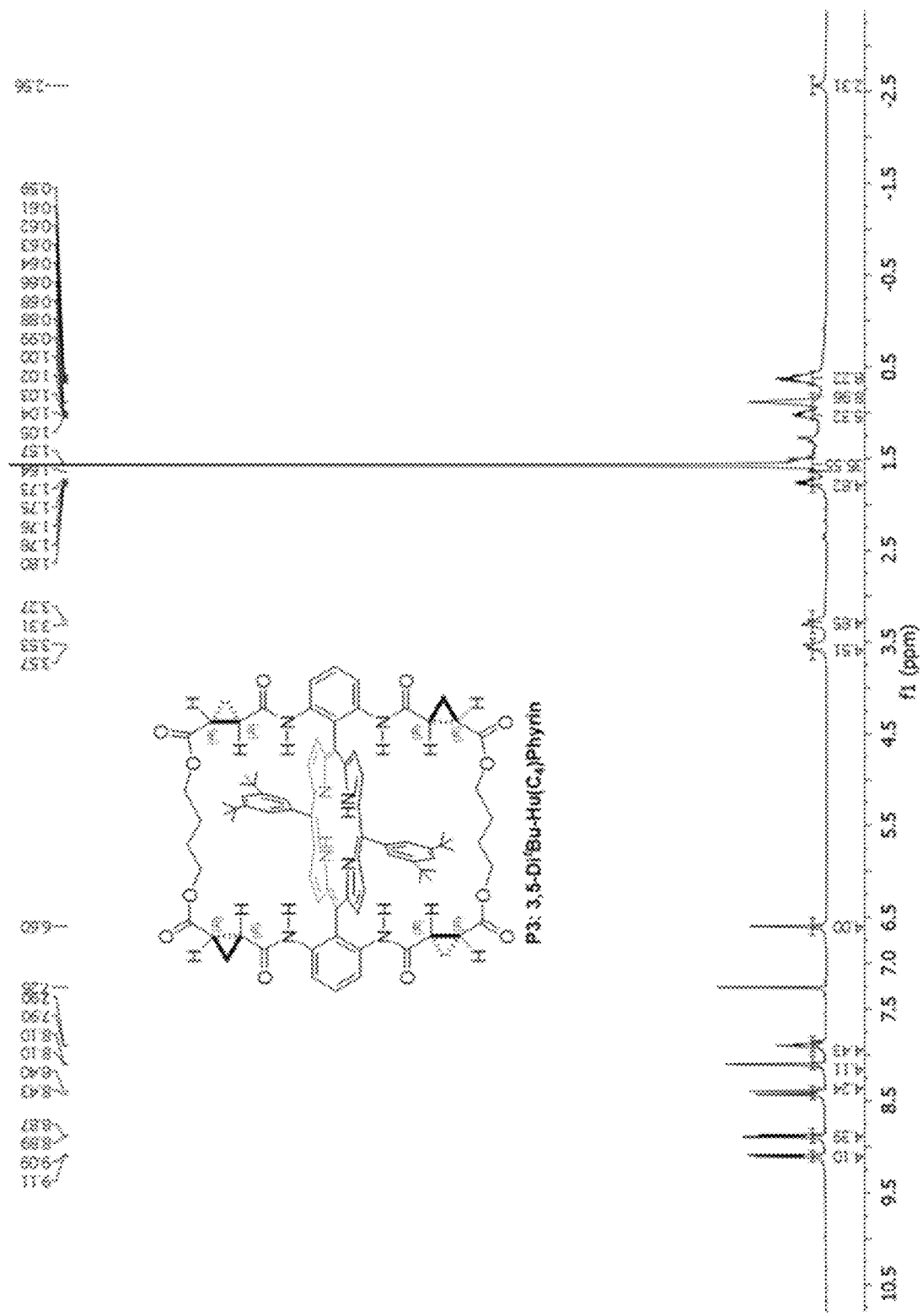
FIGS. 15A and 15B show, respectively, $^1$H and $^{13}$C NMR spectra for P3.
Figure 15B:
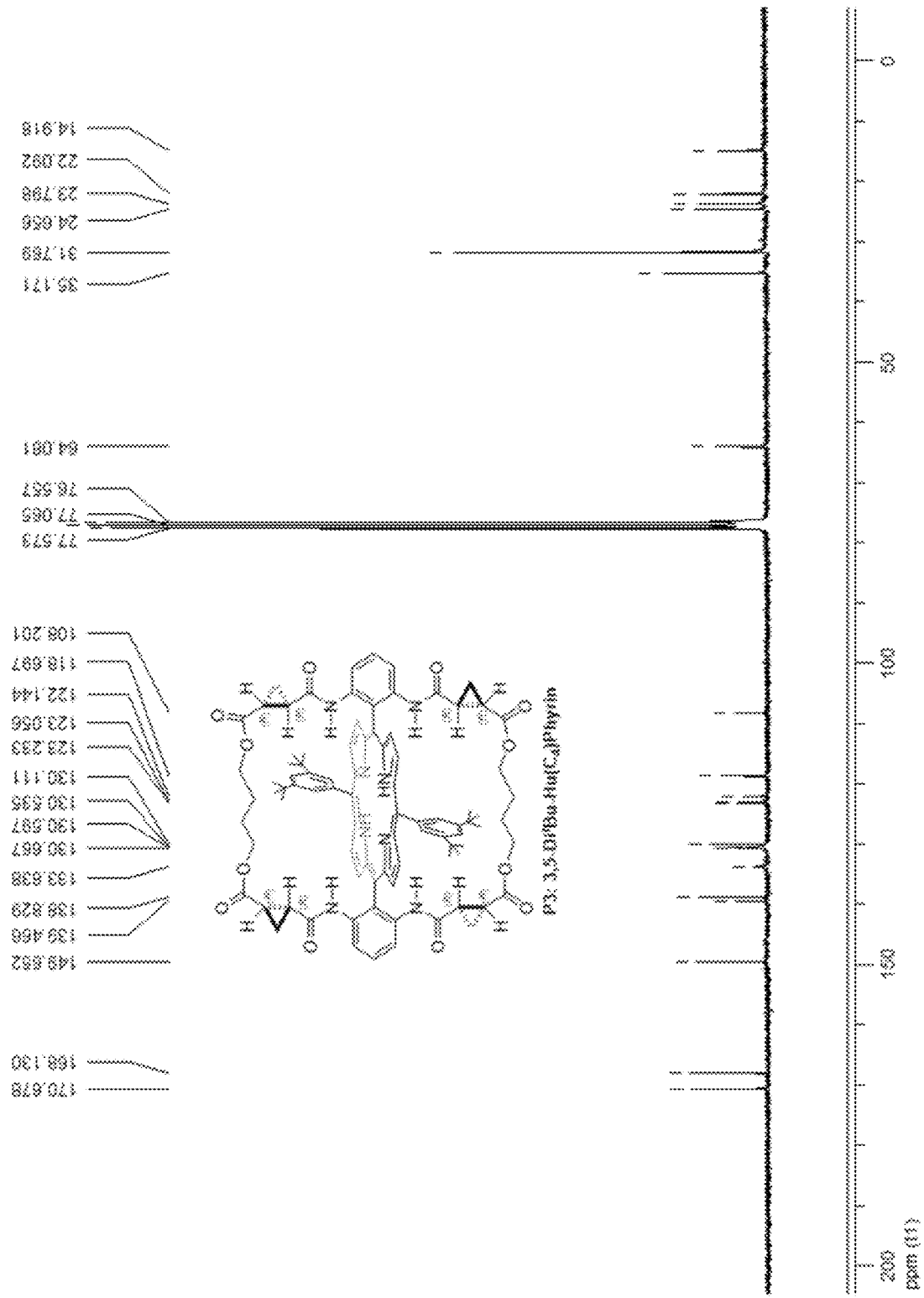

3,5-Di$^t$Bu-Hu(C$_4$)Phyrin (P3) was synthesized following General Procedure B (176 mg, 76% yield.) TLC $R_f$=0.35 (Hexanes/EtOAc 2:1). $^1$H NMR (400 MHz, CDCl$_3$) δ ppm 9.07 (d, J=4.8 Hz, 4H), 8.86 (d, J=4.8 Hz, 4H), 8.39 (d, J=8.4 Hz, 4H), 8.08 (d, J=1.8 Hz, 4H), 7.92-7.79 (m, 4H), 6.58 (s, 4H), 3.69-3.45 (m, 4H), 3.44-3.17 (m, 4H), 1.86-1.67 (m, 4H), 1.56 (s, 36H), 1.05-0.95 (m, 4H), 0.92-0.85 (m, 8H), 0.68-0.55 (m, 8H), −2.56 (s, 2H); $^{13}$C NMR (100 MHz, CDCl$_3$) δ ppm 170.7, 168.1, 149.6, 139.4, 138.8, 133.8, 130.7, 130.6, 130.5, 130.1, 123.2, 123.0, 122.1, 118.7, 108.2, 64.1, 35.2, 31.8, 24.6, 23.8, 22.1, 14.9; HRMS (ESI) m/z calcd for [M+Na]$^+$ 1477.6889, obsd; 1477.6867; UV-vis (CHCl$_3$), $\lambda_{max}$ nm (log ε): 421 (5.23), 519 (4.73), 551 (4.34), 593 (4.31), 647 (4.12). (See also FIGS. 15A-15B.)

Figure 16A:
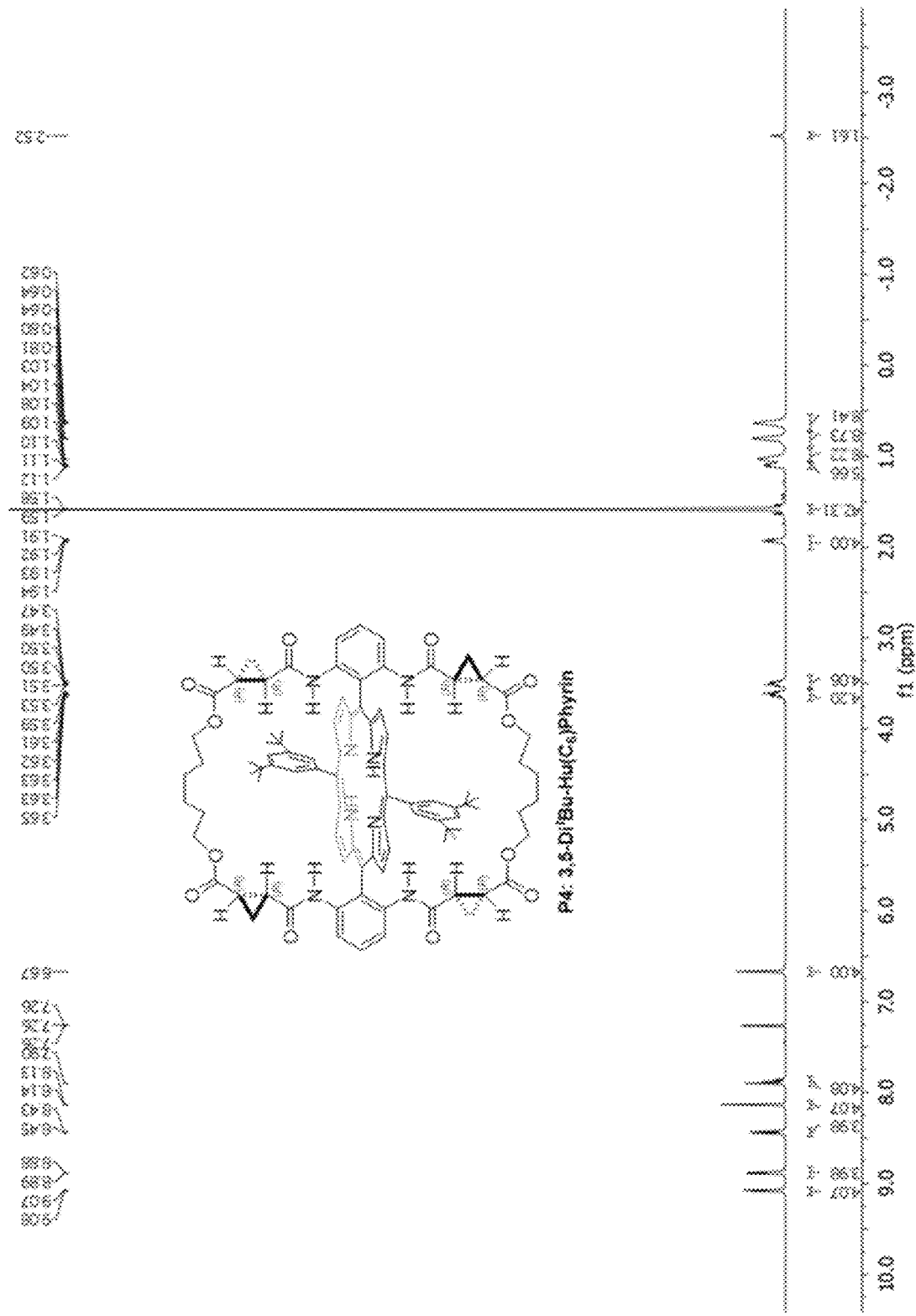
FIGS. 16A and 16B show, respectively, $^1$H and $^{13}$C NMR spectra for P4.
Figure 16B:
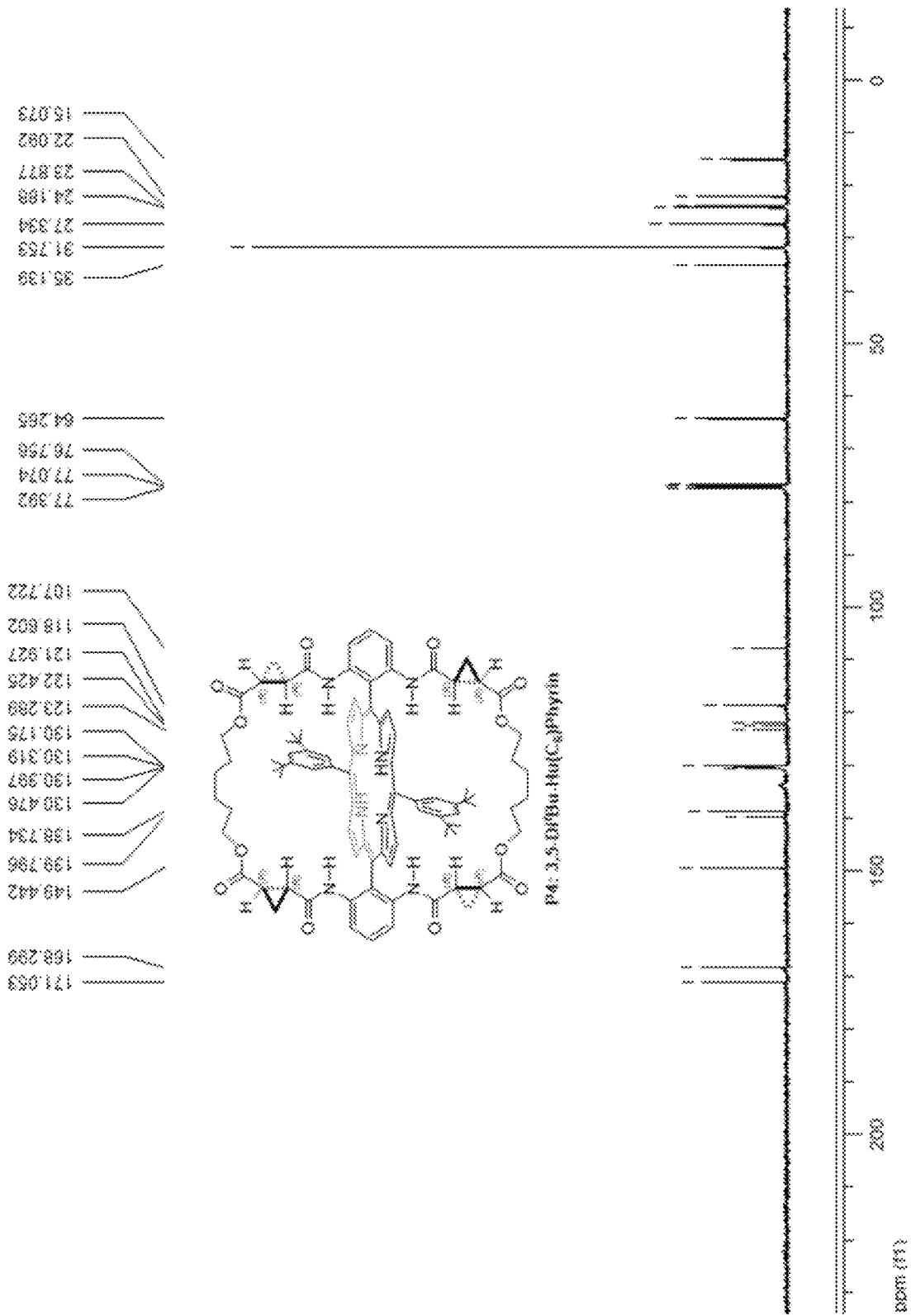

122.4, 121.9, 118.6, 107.7, 64.3, 35.1, 31.8, 27.3, 24.2, 23.9, 22.1, 15.1; HRMS (ESI) m/z calcd for [M+Na]$^+$ 1533.7515, obsd; 1533.7542; UV-vis (CHCl$_3$), $\lambda_{max}$ nm (log ε): 420 (5.33), 516 (4.73), 551 (4.36), 590 (4.23), 645 (4.20). (See also FIGS. 16A-16B.)

Example 5: General Procedure C (Cobalt Insertion Reactions)

The desired porphyrin (1.0 equiv) and CoCl$_2$ (8.0 equiv) were placed in an oven dried, resealable Schlenk tube. The tube was capped with a Teflon screw cap, evacuated, and backfilled with nitrogen. The screw cap was replaced with a rubber septum. 2,6-Lutidine (4.0 equiv) and THF (0.05 M) were added and the tube was purged with nitrogen for 1 min and sealed with a Teflon screw cap. The reaction mixture was stirred at 100° C. for 12 h prior to being cooled to r.t. The reaction mixture was diluted with DCM and washed with brine. The organic layer was separated, dried, and concentrated. The residue was purified by flash silica gel chromatography (Hexanes:EtOAc 1:1) to give the title compound.

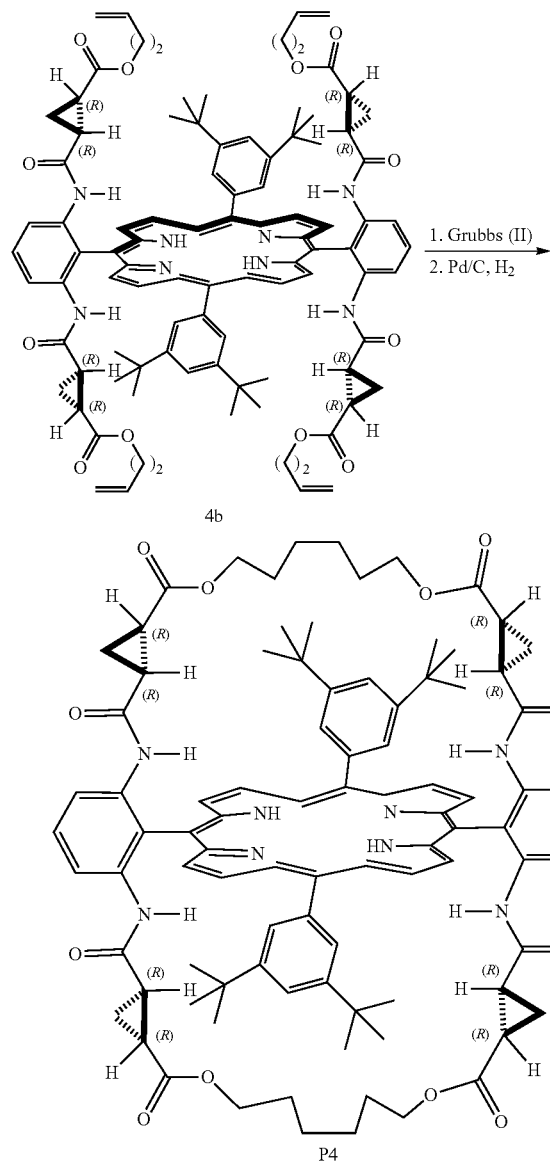

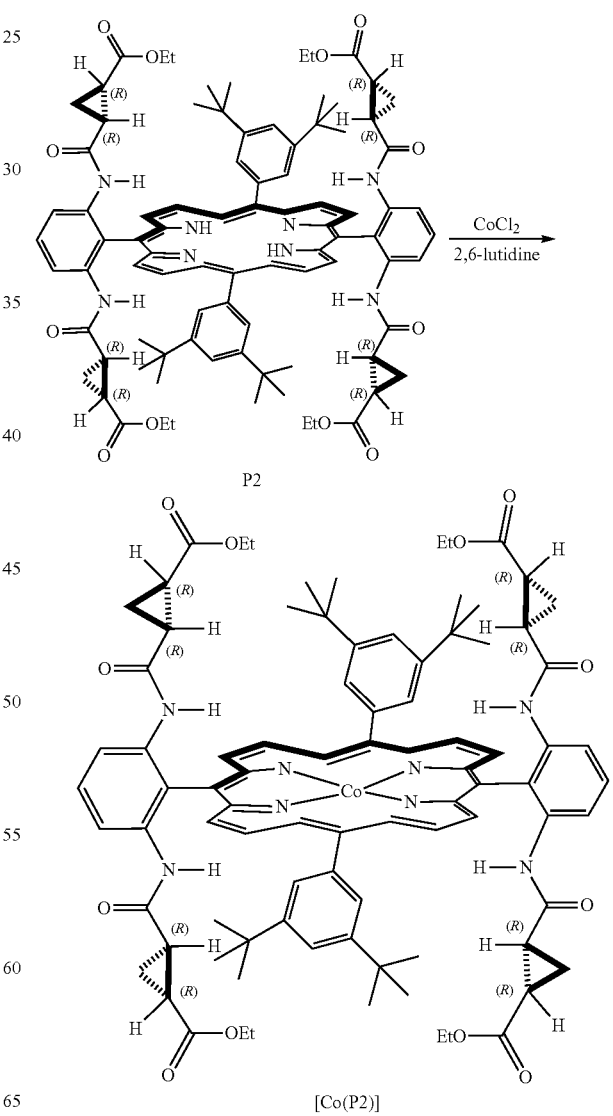

3,5-Di$^t$Bu-Hu(C$_6$)Phyrin (P4) was synthesized following General Procedure B (230 mg, 85% yield.); TLC R$_f$=0.37 (Hexanes/EtOAc 2:1). $^1$H NMR (400 MHz, CDCl$_3$) δ ppm 9.07 (d, J=4.8 Hz, 4H), 8.87 (d, J=4.8 Hz, 4H), 8.43 (d, J=8.3 Hz, 4H), 8.12 (s, 4H), 7.92-7.82 (m, 4H), 6.66 (s, 4H), 3.73-3.38 (m, 8H), 1.99-1.85 (m, 4H), 1.57 (s, 36H), 1.22-0.91 (m, 12H), 0.90-0.70 (m, 8H), 0.66-0.55 (m, 8H), −2.52 (s, 2H); $^{13}$C NMR (100 MHz, CDCl$_3$) δ ppm 171.1, 168.3, 149.4, 139.8, 138.7, 130.5, 130.4, 130.3, 130.2, 123.3,

[Co(P2)] (P2=3,5-Di$^t$Bu-(Et)TaoPhyrin) was synthesized following General Procedure C (58 mg, 93% yield). HRMS (ESI) m/z calcd for [M+H]$^+$ 1516.6558, obsd 1516.6588. UV-vis (CHCl$_3$), $\lambda_{max}$ nm (log ε): 413 (4.93), 529 (4.74), 558 (5.36).

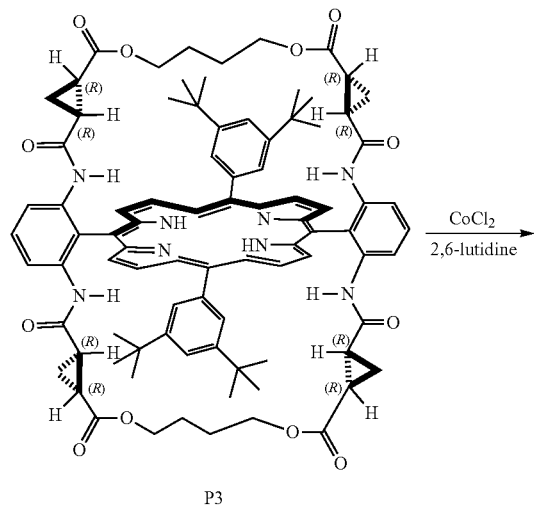

P3

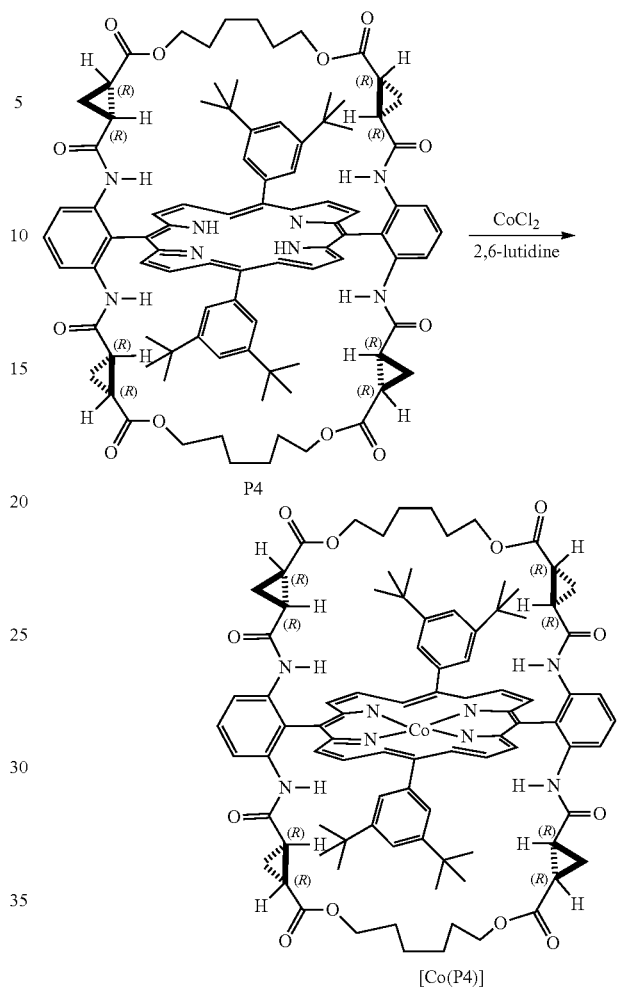

P4

[Co(P4)]

[Co(P4)] (P4=3,5-Di$^t$Bu-Hu(C$_6$)Phyrin) was synthesized following General Procedure C (215 mg, 90% yield). HRMS (ESI) m/z calcd for [M+H]$^+$ 1568.6871, obsd 1568.6894. UV-vis (CHCl$_3$), $\lambda_{max}$ nm (log ε): 412 (5.29), 529 (4.06), 556 (3.71).

Example 6: General Procedure for Cyclopropanation Reaction

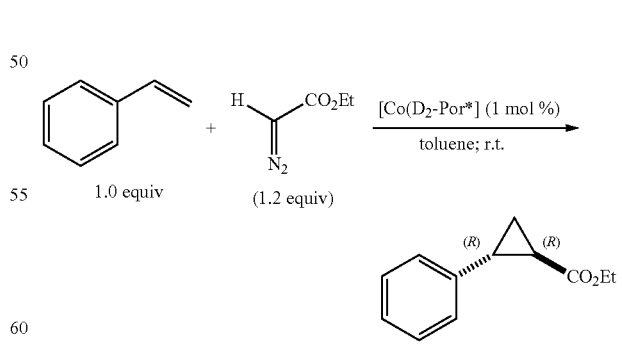

[Co(P3)]

[Co(P3)] (P3=3,5-Di$^t$Bu-Hu(C$_4$)Phyrin) was synthesized following General Procedure C (169 mg, 94% yield). HRMS (ESI) m/z calcd for [M+H]$^+$ 1512.6245, obsd 1512.6259. UV-vis (CHCl$_3$), $\lambda_{max}$ nm (log ε): 413 (4.93), 529 (4.44), 557 (4.16).

An oven dried Schlenk tube, that was previously charged with catalyst (0.001 mmol), was evacuated and backfilled with nitrogen gas. The Teflon screw cap was replaced with a rubber septum, and 0.5 ml of anhydrous toluene and styrene (0.1 mmol) were added followed by ethyl diazoacetate (0.12 mmol, 1.2 equiv) and the remaining solvent (total 1.0 mL). The Schlenk tube was then purged with nitrogen for 2 minutes and the rubber septum was replaced with a Teflon screw cap. Following completion of the reaction (1 h), the reaction mixture was purified via flash column chromatography (Hexanes/EtOAc 8:1) to afford compound 5; TLC $R_f$=0.65 (Hexanes/EtOAc 8:1). Known compound. $^1$H NMR (400 MHz, CDCl$_3$) δ ppm 7.31-7.16 (m, 3H), 7.15-7.10 (m, 2H), 4.17 (q, J=7.2 Hz, 2H), 2.52 (ddd, J=9.2, 6.4, 4.2 Hz, 1H), 1.90 (ddd, J=8.4, 5.3, 4.2 Hz, 1H), 1.67-1.52 (m, 1H), 1.32 (td, J=3.8, 2.0 Hz, 1H), 1.29 (t, J=7.2 Hz, 3H); $^{13}$C NMR (100 MHz, CDCl$_3$) δ ppm 173.3, 140.1, 128.4, 126.4, 126.1, 60.7, 26.1, 24.2, 17.0, 14.2; HPLC analysis: ee=96%. Chiral OJ-H (1% isopropanol-hexanes, 0.8 ml/min): Major t=10.48 min., Minor t=20.86 min.

Example 7: General Procedure for Aziridination Reactions

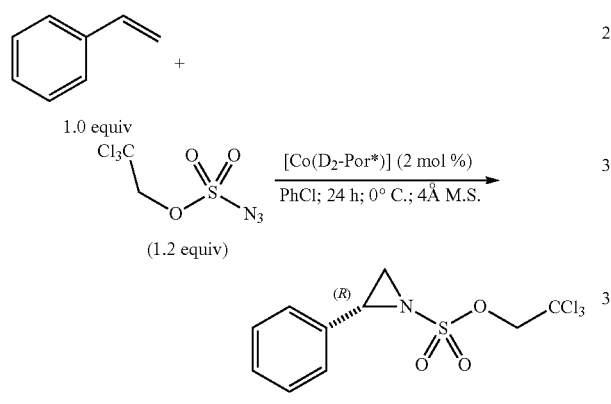

6

An oven dried Schlenk tube that was previously charged with catalyst (0.002 mmol) was evacuated and backfilled with nitrogen gas. The Teflon screw cap was replaced with a rubber septum, and 0.5 mL of anhydrous chlorobenzene and styrene (0.1 mmol) were added. The solution was cooled to 0° C. prior to the addition of TcesN$_3$ (0.12 mmol, 1.2 equiv) and the remaining chlorobenzene (0.5 mL). The Schlenk tube was then purged with nitrogen for 2 minutes and the rubber septum was replaced with a Teflon screw cap. Following completion of the reaction (24 h), the reaction mixture was purified via flash chromatography (Hexanes/EtOAc 8:1) to afford the compound 6; TLC $R_f$=0.45 (Hexanes/EtOAc 4:1). Known Compound. $^1$H NMR (400 MHz, CDCl$_3$) δ ppm 7.32-7.26 (m, 5H); 4.88, 4.81 (AB q, J=10.9 Hz, each 1H), 3.88 (dd, J=7.2, 4.6 Hz, 1H), 3.09 (d, J=7.2 Hz, 1H), 2.63 (d, J=4.6 Hz, 1H); HPLC analysis: ee=92%. Chiral OD-H (1% isopropanol-hexanes, 0.8 ml/min): Major t=24.08 min., Minor t=27.18 min.

Example 8: X-Ray Crystallography of P1, P3, and P4

X-ray diffraction data of P1 were collected using Bruker-AXS SMART-APEXII CCD diffractometer (CuKα, λ=1.54178 Å). Indexing was performed using APEX2 (Difference Vectors method). Data integration and reduction were performed using SaintPlus 6.01. Absorption correction was performed by multi-scan method implemented in SADABS. Space group was determined using XPREP implemented in APEX2. The structure was solved using SHELXS-97 (direct methods) and refined using SHELXL-97 (full-matrix least-squares on F2) contained in APEX2 and WinGX v1.70.01 programs packages.

Figure 7:
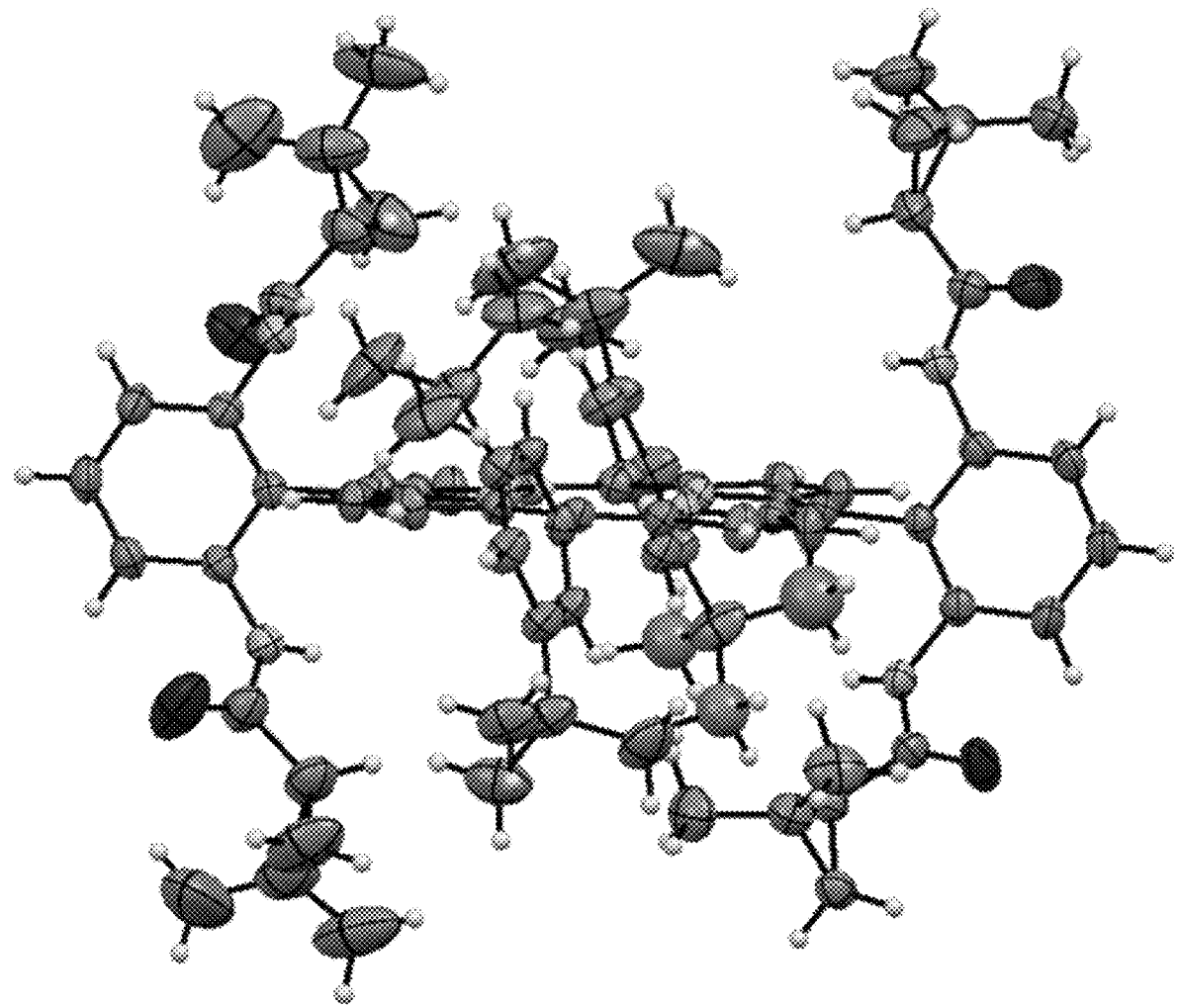
FIG. 7 shows an X-ray crystal structure for chiral amidoporphyrin P1 of the present disclosure.

P1 (FIG. 7): All non-hydrogen atoms (except disordered) were refined anisotropically. Hydrogen atoms were placed in geometrically calculated positions and included in the refinement process using riding model with isotropic thermal parameters: $U_{iso}(H)=1.5U_{eq}$(—CH$_3$), $U_{iso}(H)=1.2U_{eq}$ (—CH$_2$,—CH,—NH). Structural voids are partially occupied by disordered solvent molecules (CHCl$_3$, C$_6$H$_{14}$). Disordered groups (t-butyl, —NHCOC$_5$H$_9$)/molecules (CHCl$_3$, C$_6$H$_{14}$) have been refined using geometry restraints (DFIX, DANG). Targeted distances have been taken from CSD (Cambridge Structural Database) search of similar fragments. Crystal data and refinement conditions are shown in Table 1.

TABLE 1

| Crystal Data and Refinement Conditions for P1 | |
|---|---|
| Temperature/K | 228(2) |
| Crystal system | monoclinic |
| Space group | P2$_1$ |
| a/Å | 17.8323(2) |
| b/Å | 18.4144(2) |
| c/Å | 25.7409(4) |
| α/° | 90.00 |
| β/° | 105.8270(10) |
| γ/° | 90.00 |
| Volume/Å$^3$ | 8132.13(18) |
| Z | 4 |
| $ρ_{calc}$ mg/mm$^3$ | 1.126 |
| m/mm$^{-1}$ | 1.111 |
| F(000) | 2952.0 |
| Crystal size/mm$^3$ | 0.21 × 0.17 × 0.13 |
| 2Θ range for data collection | 3.56 to 140.4° |
| Index ranges | −21 ≤ h ≤ 21, −22 ≤ k ≤ 22, −31 ≤ l ≤ 31 |
| Reflections collected | 97753 |
| Independent reflections | 28950[R(int) = 0.0425] |
| Data/restraints/parameters | 28950/42/1847 |
| Goodness-of-fit on F$^2$ | 1.036 |
| Final R indexes [I > = 2σ (I)] | R$_1$ = 0.0648, wR$_2$ = 0.1756 |
| Final R indexes [all data] | R$_1$ = 0.0790, wR$_2$ = 0.1906 |
| Largest diff. peak/hole/e Å$^{-3}$ | 0.88/−0.32 |
| Flack parameter | 0.033(19) |
| Temperature/K | 228(2) |

The X-ray diffraction data for P3 was measured on a Bruker D8 Venture PHOTON 100 CMOS system equipped with a Cu Kα INCOATEC Imus micro-focus source (λ=1.54178 Å). Indexing was performed using APEX (Difference Vectors method). Data integration and reduction were performed using SaintPlus 6.01. Absorption correction was performed by multi-scan method implemented in SADABS. Space groups were determined using XPREP implemented in APEX2. The structure was solved using SHELXS-97 (direct methods) and refined using SHELXL-97 (full-matrix least-squares on F2) contained in APEX2 and WinGX v1.70.01 programs packages.

Figure 8:
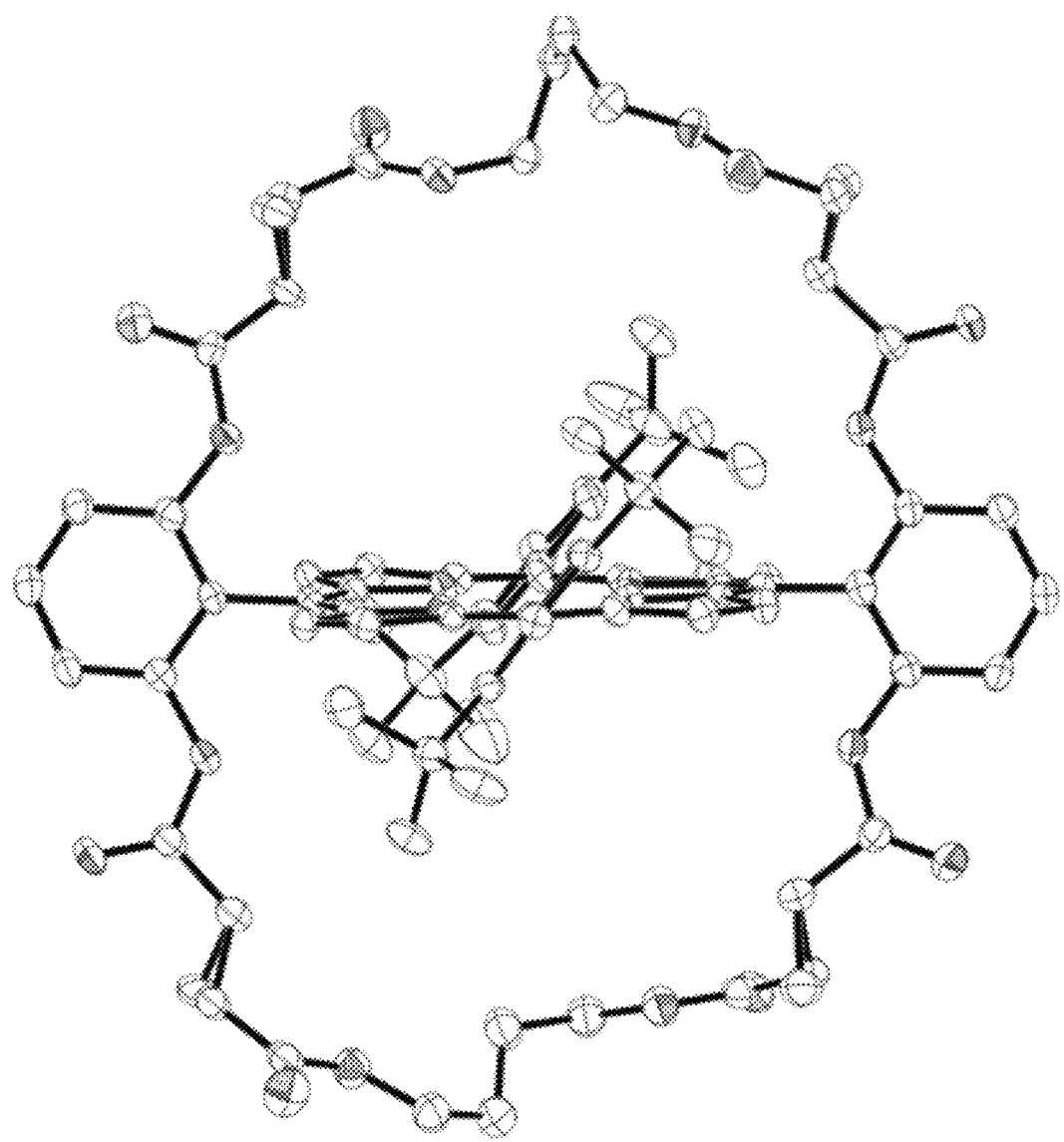
FIG. 8 shows an X-ray crystal structure for chiral bridged-amidoporphyrin P3 of the present disclosure.

P3 (FIG. 8): All non-hydrogen atoms were refined anisotropically. Part of the chain in the porphyrin molecule is disordered over two positions with approximate refined occupancy ratio of 0.55:0.44. Those disordered parts have been refined using distance restraints (targeted distances were taken from Cambridge Structural Database). The following atoms have been refined using ISOR: C86B C86A C87B C87A and SIMU C87A C87B. Crystal data and refinement conditions are shown in Table 2.

TABLE 2

Crystal Data and Refinement Conditions for P3

| | |
|---|---|
| Empirical formula | $C_{100.7}H_{125.25}N_8O_{14}$ |
| Moiety Formula | '$C_{88}H_{94}N_8O_{12}$, $2(C_4H_{10}O)$, $0.94(C_5H_{12})$' |
| Formula weight | 1671.77 |
| Temperature/K | 105.04 |
| Crystal system | triclinic |
| Space group | P1 |
| a/Å | 12.0664(4) |
| b/Å | 13.7802(4) |
| c/Å | 14.8398(5) |
| α/° | 105.4310(10) |
| β/° | 91.875(2) |
| γ/° | 98.674(2) |
| Volume/Å³ | 2344.49(13) |
| Z | 1 |
| $\rho_{calc}$ mg/mm³ | 1.184 |
| m/mm$^{-1}$ | 0.630 |
| F(000) | 897.0 |
| Crystal size/mm³ | 0.16 × 0.13 × 0.11 |
| Radiation | CuKα (λ = 1.54178) |
| 2Θ range for data collection | 6.196 to 138.214° |
| Index ranges | $-14 \le h \le 14$, $-16 \le k \le 16$, $-17 \le l \le 17$ |
| Reflections collected | 35810 |
| Independent reflections | 15847[R(int) = 0.0371] |
| Data/restraints/parameters | 15847/68/1263 |
| Goodness-of-fit on F² | 1.035 |
| Final R indexes [I >= 2σ (I)] | $R_1 = 0.0487$, $wR_2 = 0.1253$ |
| Final R indexes [all data] | $R_1 = 0.0560$, $wR_2 = 0.1306$ |
| Largest diff. peak/hole/e Å$^{-3}$ | 0.85/−0.38 |
| Flack parameter | 0.06(8) |

Figure 9:
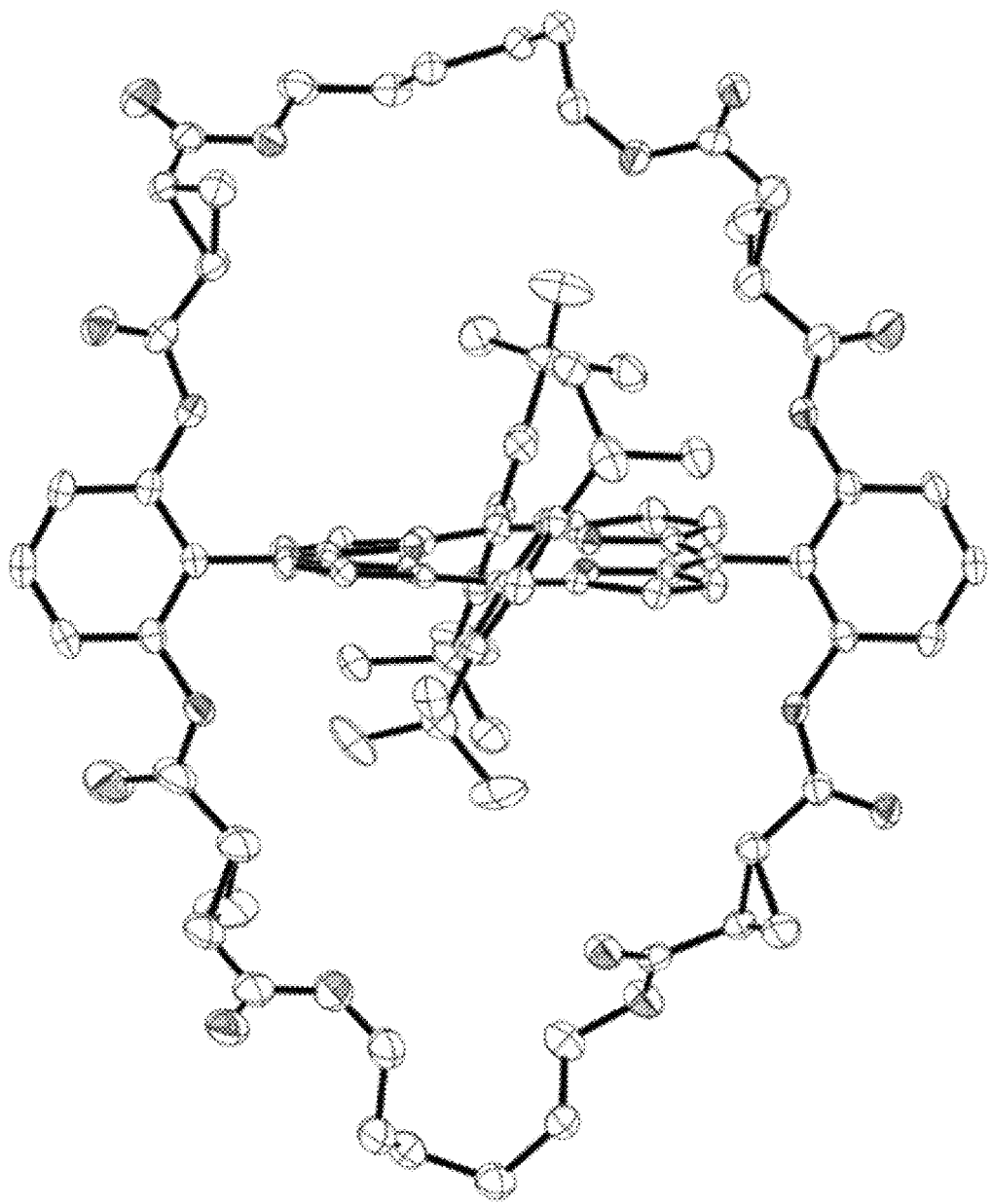
FIG. 9 shows an X-ray crystal structure for chiral bridged-amidoporphyrin P4 of the present disclosure.

P4 (FIG. 9): A similar procedure was followed as for P3. Several solvent molecules inside the porphyrin cavities could not be satisfactorily refined; the program SQUEEZE was used to address this. Crystal data and refinement conditions are shown in Table 3.

TABLE 3

Crystal Data and Refinement Conditions for P4

| | |
|---|---|
| Identification code | $C_{92}H_{102}N_8O_{12}$ (k0l-441) |
| Empirical formula | $C_{185}H_{205}Cl_3N_{16}O_{24}$ |
| Formula weight | 3142.99 |
| Temperature | 100(2) K |
| Wavelength | 1.54178 Å |
| Crystal system | Monoclinic |
| Space group | P2$_1$ |
| Unit cell dimensions | a = 14.5614(5) Å |
| | b = 24.3949(8) Å |
| | c = 25.7886(8) Å |
| Volume | 9130.3(5) A³ |
| Z | 2 |
| Density (calculated) | 1.143 mg/m³ |
| Absorption coefficient | 0.998 mm$^{-1}$ |
| F(000) | 3340 |
| Crystal size | 0.480 × 0.220 × 0.200 mm³ |
| Theta range for data collection | 2.497 to 68.328°. |
| Index ranges | $-17 \le h \le 16$, $-28 \le k \le 29$, $-23 \le l \le 30$ |
| Reflections collected | 78357 |
| Independent reflections | 31557 [R(int) = 0.0316] |
| Completeness to theta = 67.679° | 99.4% |
| Absorption correction | Semi-empirical from equivalents |
| Max. and min. transmission | 0.7531 and 0.6022 |
| Refinement method | Full-matrix least-squares on F² |
| Data/restraints/parameters | 31557/1914/2117 |
| Goodness-of-fit on F² | 1.037 |
| Final R indices [I > 2sigma(I)] | R1 = 0.0438, wR2 = 0.1146 |
| R indices (all data) | R1 = 0.0469, wR2 = 0.1174 |
| Absolute structure parameter | 0.047(6) |

TABLE 3-continued

Crystal Data and Refinement Conditions for P4

| | |
|---|---|
| Extinction coefficient | n/a |
| Largest diff. peak and hole | 0.869 and −0.393 e.Å$^{-3}$ |

Example 9: Cavity-Size Approximation for P3 and P4 Based on X-Ray

Figure 10A:
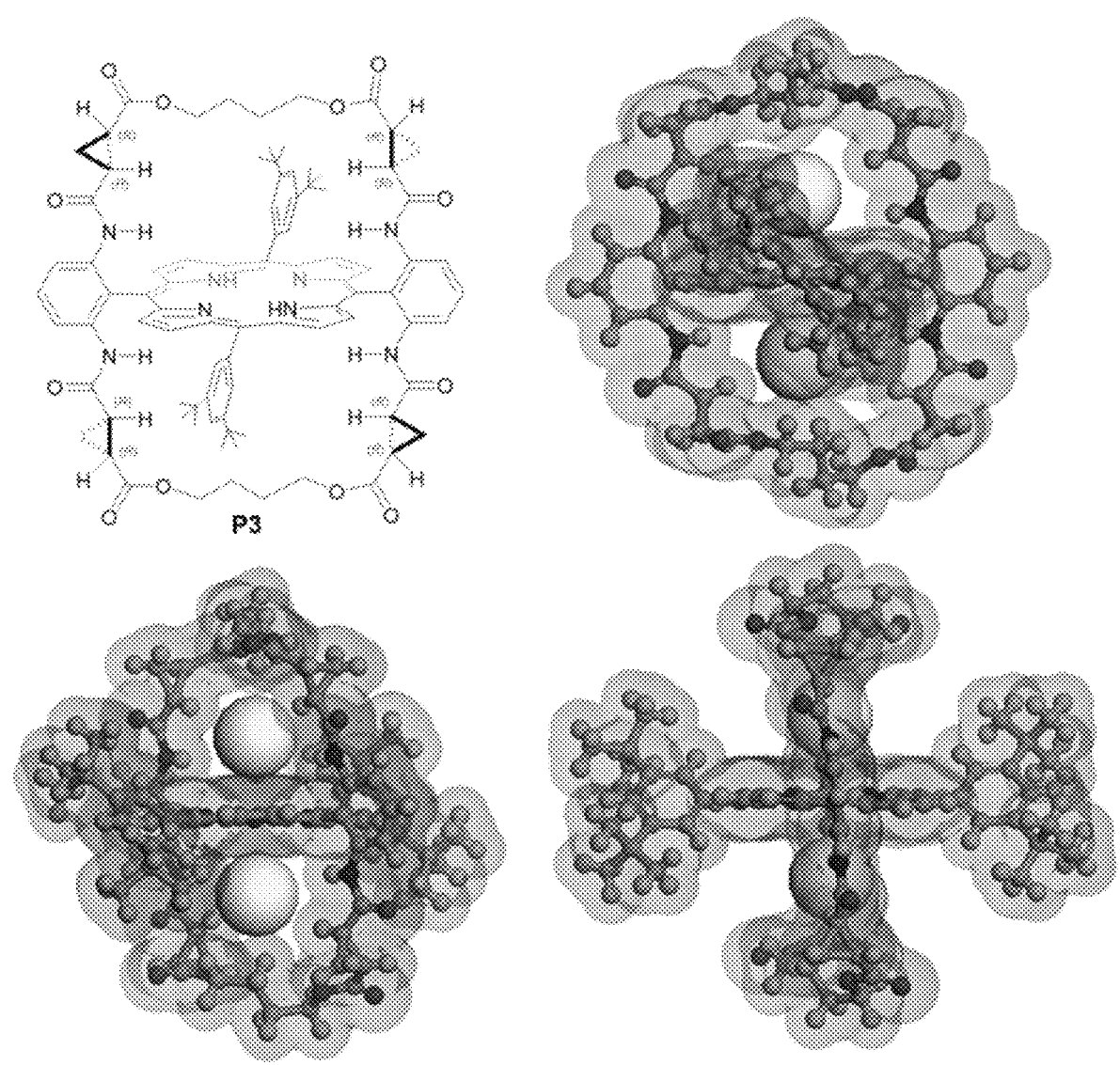
FIG. 10A shows a cavity-size approximation for P3 (3,5-di$^t$bu-Hu($C_4$)phyrin).
Figure 10B:
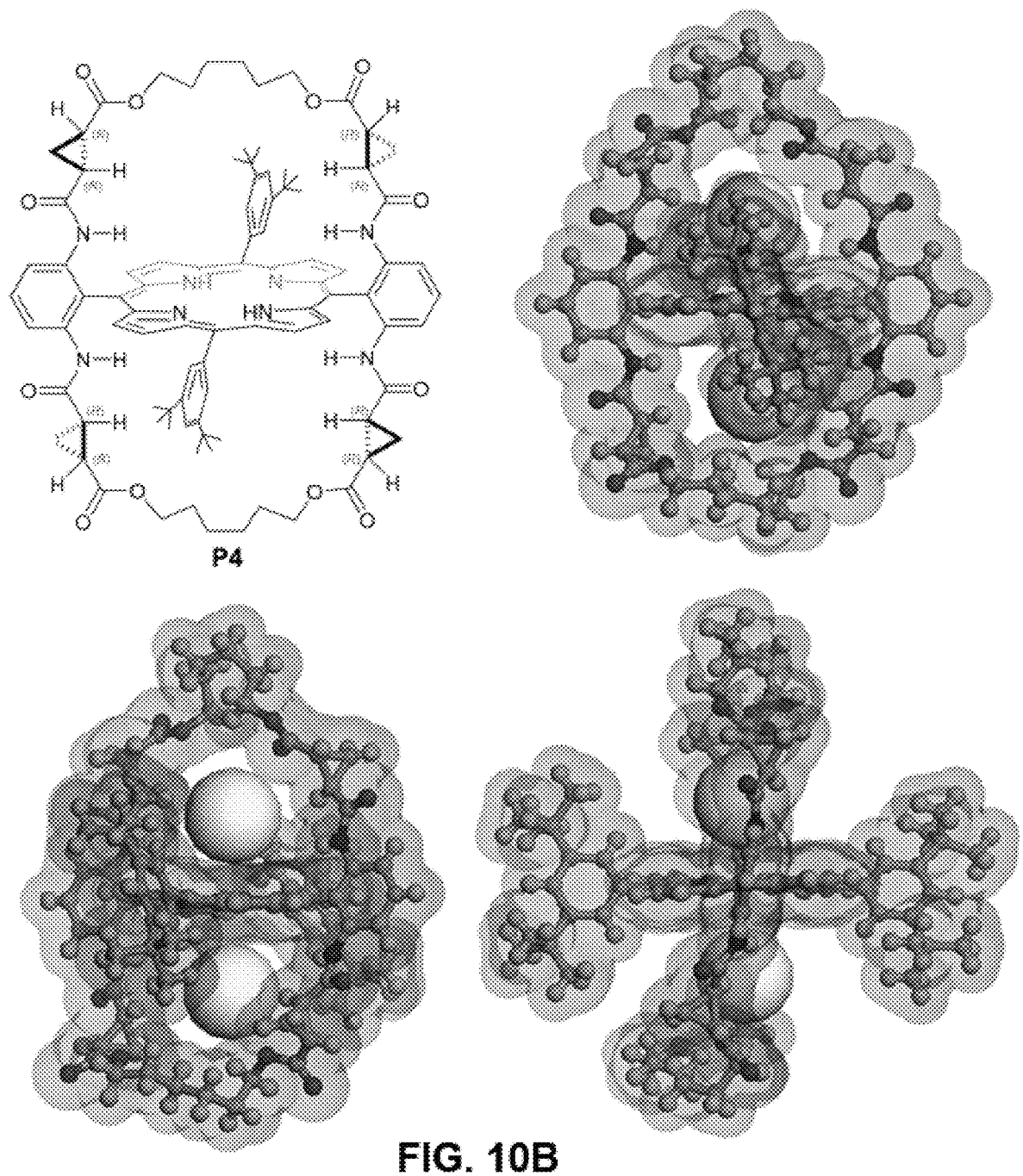
FIG. 10B shows a cavity-size approximation for P4 (3,5-di$^t$bu-Hu($C_6$)phyrin).

The spheres were placed at the center which just touches van der Waals surface of porphyrin. All measurements are approximate (radius). The graph was generated with Accelrys Materials Studio (FIG. 10A for P3 and FIG. 10B for P4).

Figure 3:
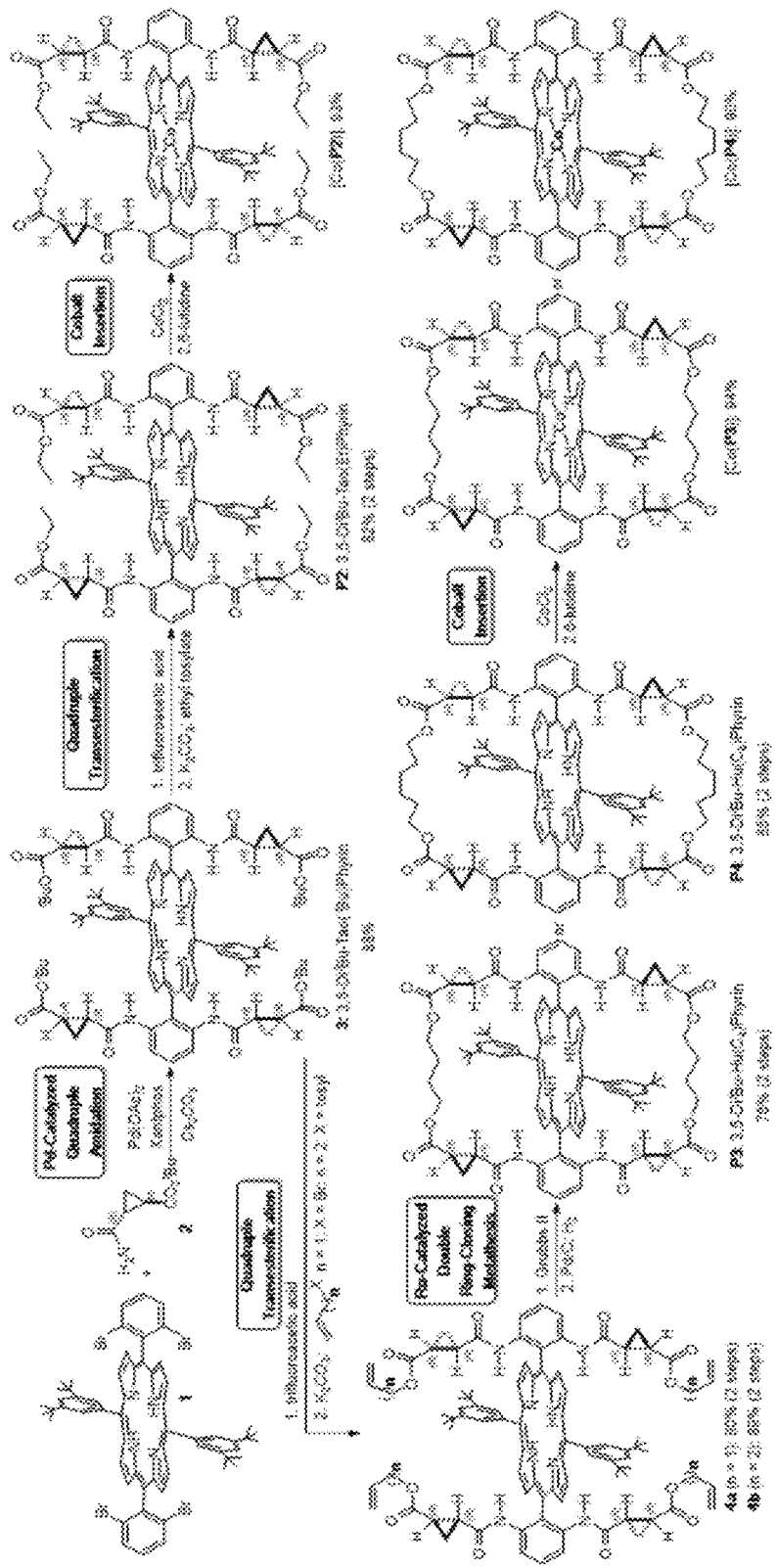
FIG. 3 shows synthesis of $D_2$-symmetric chiral bridged-amidoporphyrins and cobalt (II) complexes.

Example 10: Synthesis and Characterization of Specific Chiral Bridged Amidoporphyrins For construction of the bridges, 3,5-Di$^t$Bu-Tao(Bu)Phyrin (3) (FIG. 3), a new $D_2$-symmetric chiral amidoporphyrin that carries tert-butyl ester moieties, was selected as the scaffold structure, considering that the ester functionalities in 3 may serve as convenient handles for building the bridges. Following a previously established procedure, 3 was prepared in 88% yield through Pd-catalyzed quadruple amidation reaction of tetrabromoporphyrin 1 with the optically pure chiral amide 2 (FIG. 3). The tert-butyl esters in 3 could readily undergo transesterification involving the first generation of the corresponding porphyrin carboxylic acids by hydrolysis and then subsequent O-alkylation with alkyl halides or tosylates. For example, the use of ethyl tosylate afforded 3,5-Di$^t$Bu-Tao(Et)Phyrin (P2) in 82% yield for the two-step transformation, which was metallated to form Co(II) complex [Co(P2)] in 93% yield. When the transesterification operation was carried out with allyl bromide and homoallyl tosylate, 4a and 4b were formed in 80% and 89% yields, respectively. With the second-generation Grubbs catalyst, 4a and 4b underwent ring-closing metathesis to form olefin-bridged porphyrins as a non-consequential mixture of cis and trans-isomers. They were directly hydrogenated to form the alkyl-bridged porphyrins P3 (3,5-Di$^t$Bu-Hu(C$_4$)Phyrin) and P4 (3,5-Di$^t$Bu-Hu(C$_6$)Phyrin) in 76% and 85% yields, respectively. The five-step synthesis was accomplished in high overall yields (54% for P3 and 67% for P4). Metallation gave Co(II) complexes [Co(P3)] and [Co(P4)] in 94% and 90% yields, respectively, on the scale of hundreds of milligrams.

Example 11: Effect of Bridging on Conformation of $D_2$-Poprhyrins

Figure 4:
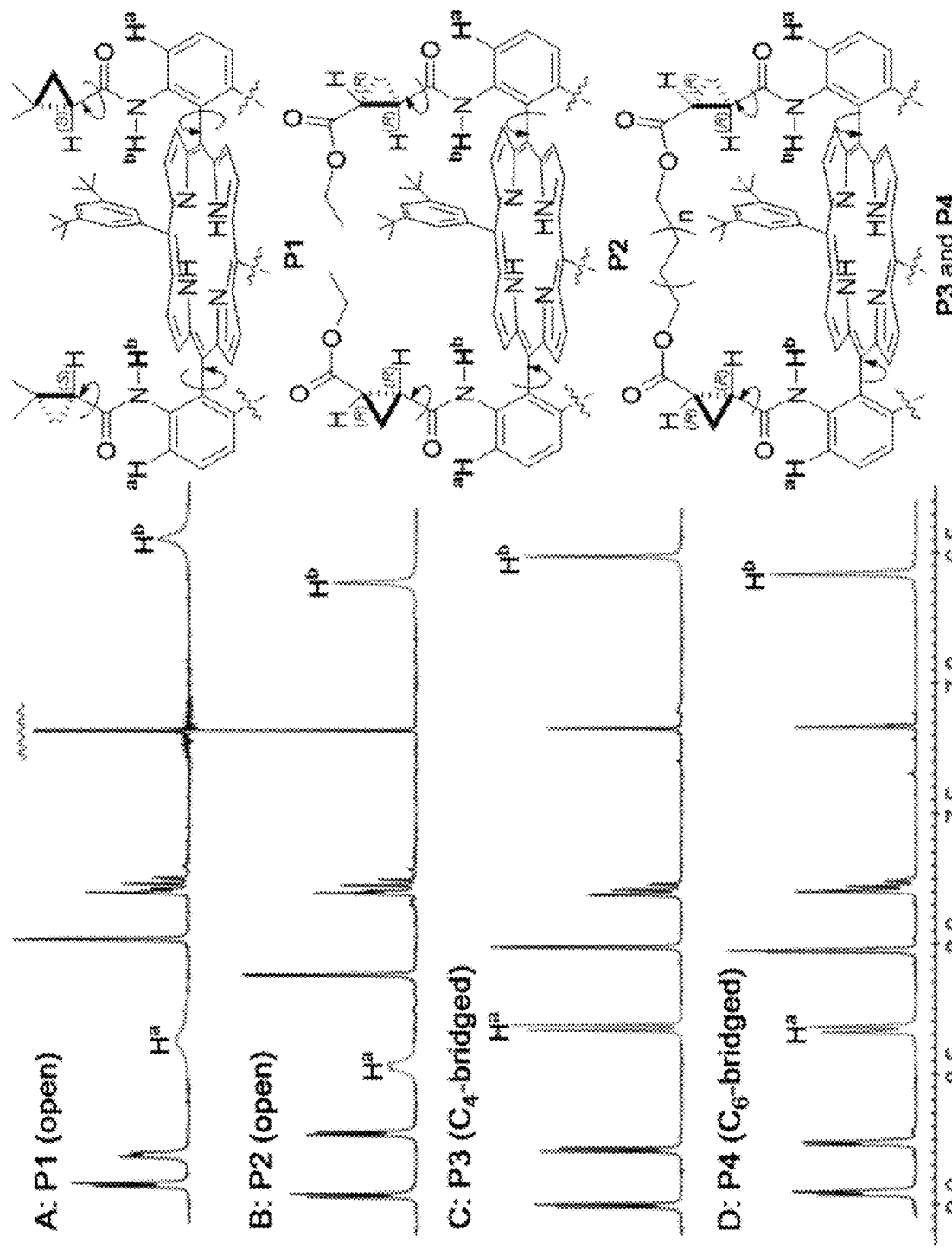
FIG. 4 shows low-field region $^1$H-NMR spectra of chiral amidoporphyrins.

To examine the bridging effect on the conformation of $D_2$-Por*, the $^1$H-NMR spectra of $C_4$-bridged P3 and $C_6$-bridged P4 were analyzed in comparison with the open counterparts P2 and P1. As illustrated by the low-field region of their $^1$H-NMR spectra (FIG. 4), both the line width and chemical shift of the signals corresponding to the aromatic protons H$^a$ and the amide protons H$^b$ vary significantly. Although existing $D_2$-Por*, as represented by P1, have a relatively-defined configuration that directs the ortho-chiral amide units toward the center of the porphyrin where the Co(II) ion is situated, they bear a certain degree of conformational flexibility owing to the existence of rotational freedom between the meso-phenyl rings and the porphyrin plane as well as between the trans-amides and the cyclopropyl groups (FIG. 4A). This rotational freedom is manifested by the broad $H^a$ and $H^b$ signals at 8.45 and 6.52 ppm, respectively (FIG. 4A). Due to steric effects of —CO$_2$Et, the $H^a$ and $H^b$ signals in P2 became less broad and shifted to the lower field at 8.55 and 6.69 ppm, respectively, (FIG. 4B) As a result of the bridging, both $H^a$ (8.41 ppm) and $H^b$ (6.60 ppm) signals in P3 were notably sharpened, signifying the rigidification of the conformational freedom (FIG. 4C). Similar but slightly less sharpening of the $H^a$ (8.44 ppm) and $H^b$ (6.66 ppm) signals in P4 indicates relatively reduced rigidification in conformation upon elongation of the bridge from $C_4$ to $C_6$ (FIG. 4D). Consequently, the more rigid conformation in P3 and P4 should enhance H-bonding capability of the chiral amide units for stabilizing the catalytic intermediates.

Example 12: Effect of Bridge Length on Cavity Size

Figure 5:
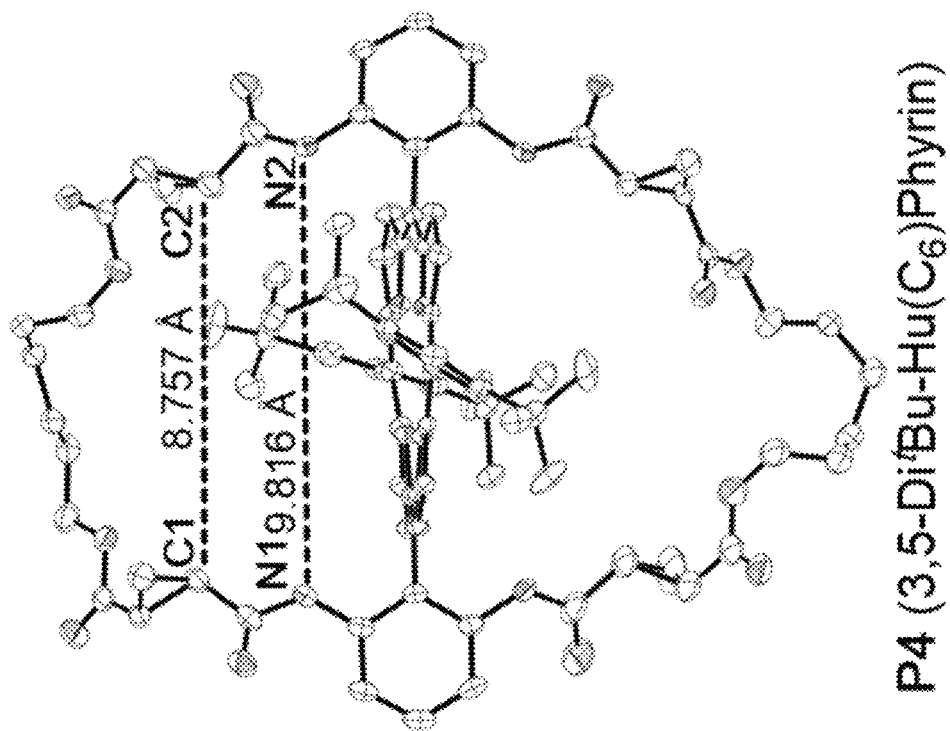
FIG. 5 shows X-ray structures of bridged amidoporphyrins. The distances between N1 and N2 and between C1 and C2 are averaged values of those on both sides of the porphyrin plane.
Figure 5:
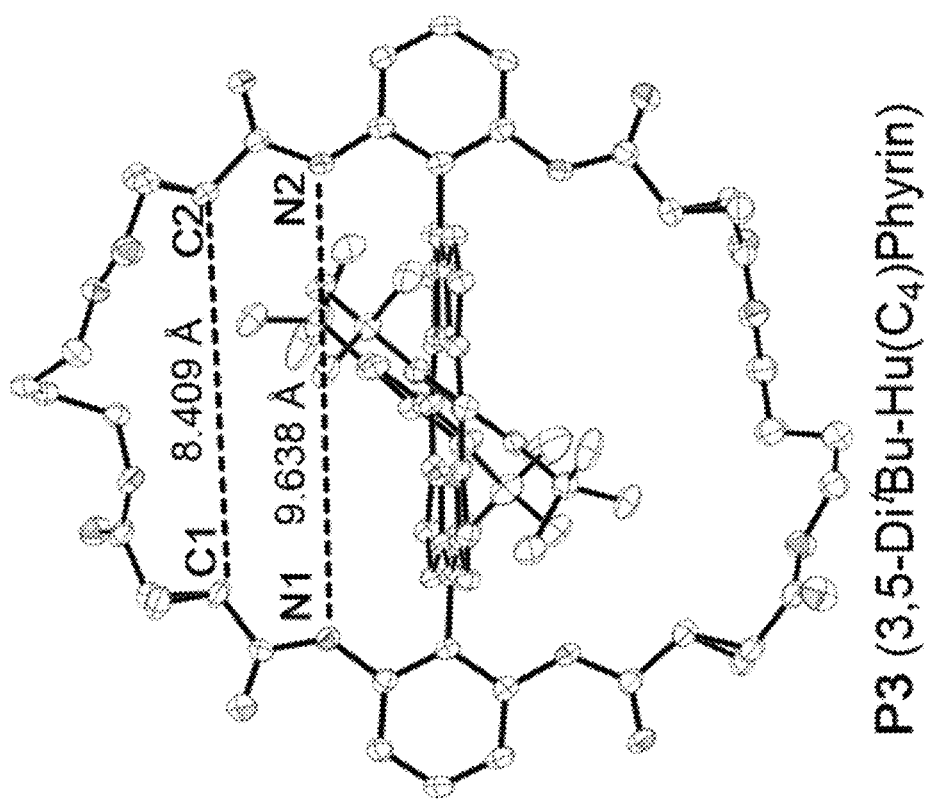

X-ray diffraction analysis unveiled the structural details of P3 and P4, including the double alkyl-bridges and associated dual cavities (FIG. 5). The 38- and 42-membered macrocyclic structures in P3 and P4 created by the double ring-closing olefin metathesis are bisected by the porphyrin core. In addition to the porphyrin ring, the macrocycles consist of multiple small rings (2 benzenes and 4 cyclopropanes) and functional groups (4 amides and 4 esters). As shown, $C_6$-bridged P4 contains a significantly larger cavity than $C_4$-bridged P3. The observation that the cavity size can be varied by simple change of the bridge length suggests a new dimension for catalyst engineering.

Example 13: Effect of Bridge Length on Catalytic Performance

Figure 6A:
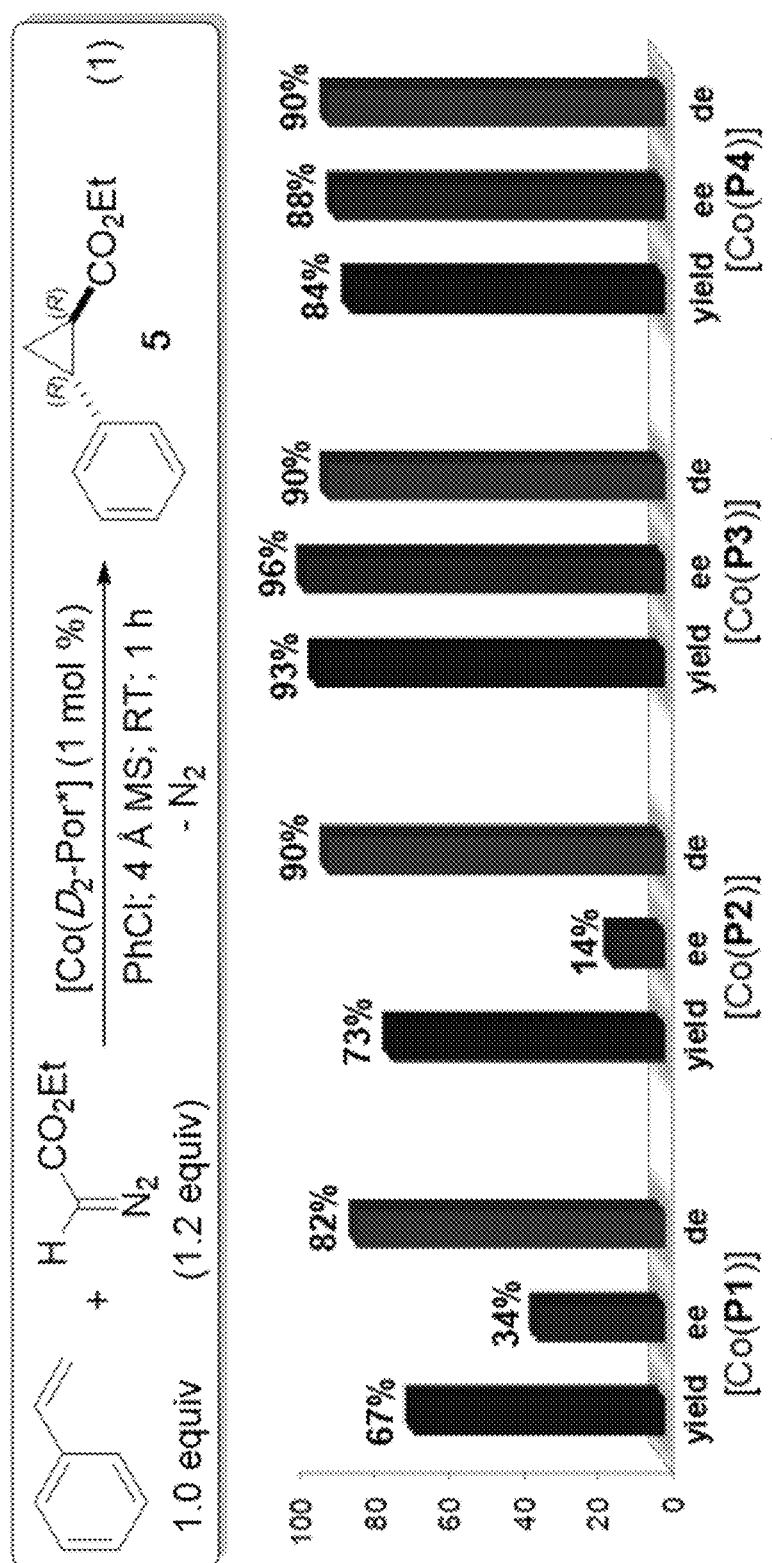
FIGS. 6A and 6B each show the effects of bridges in chiral amidoporphyrins on Co(II)-catalyzed radical cyclopropanation and aziridination.
Figure 6B:
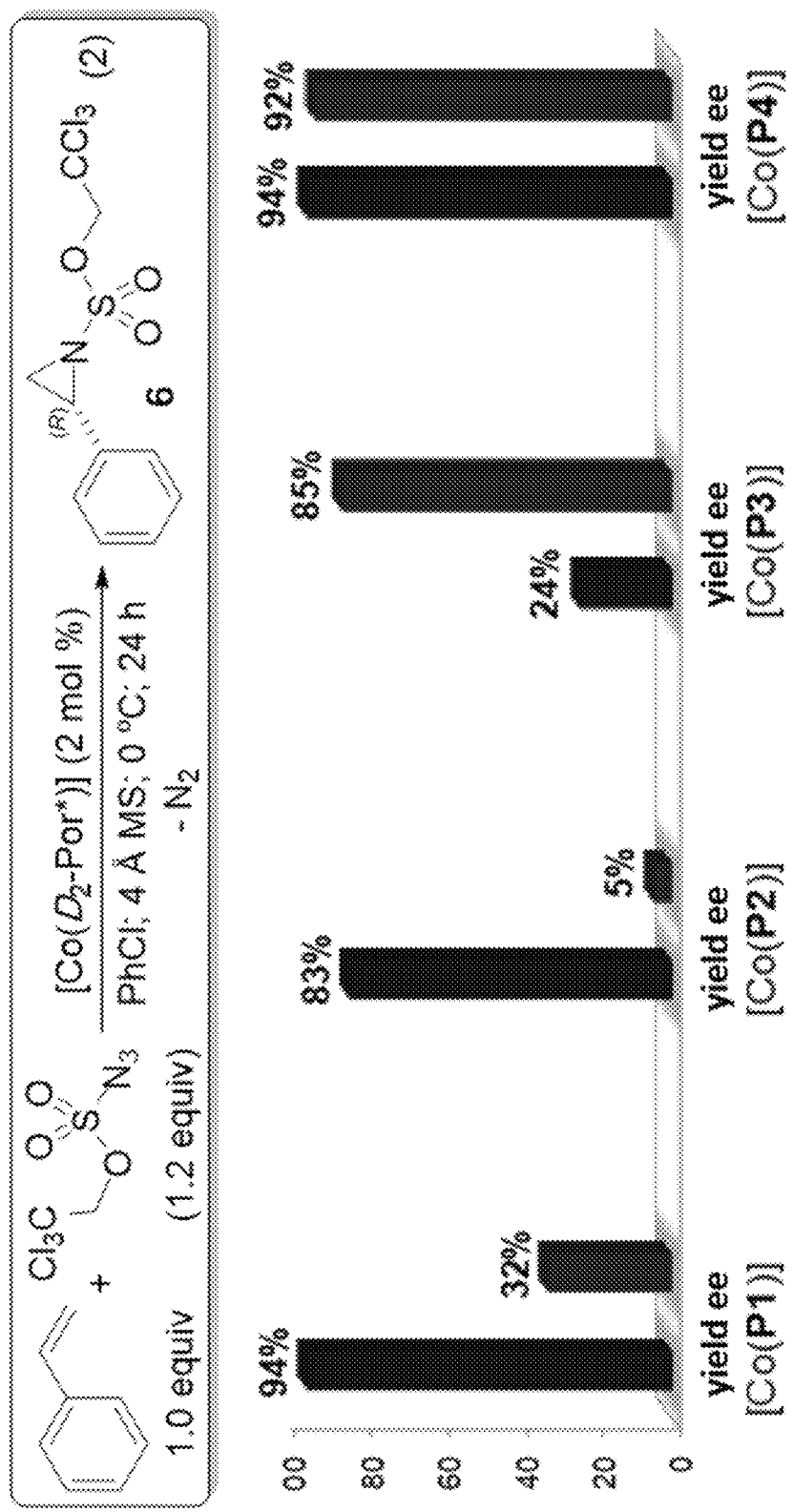
Figure 17A:
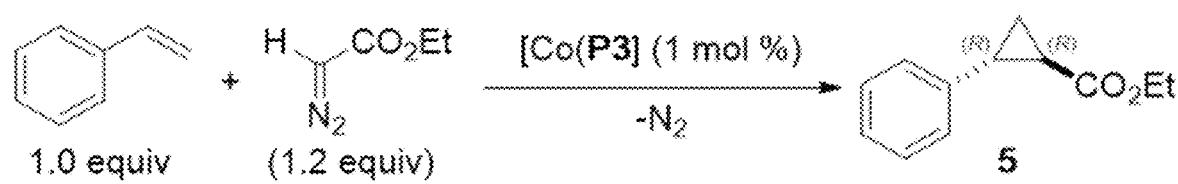
FIG. 17A shows a synthesis scheme and chiral HPLC separation of stereoisomers.
Figure 17A:
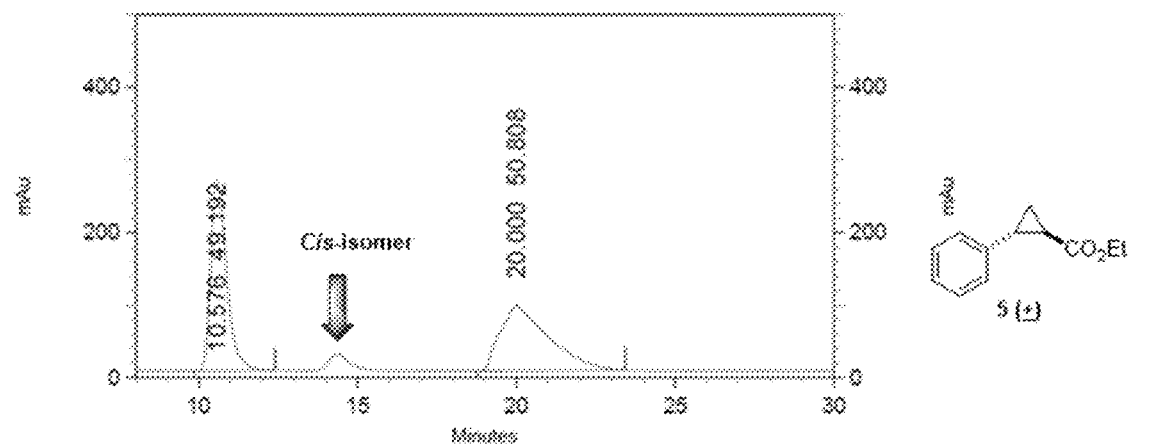
Figure 17A:
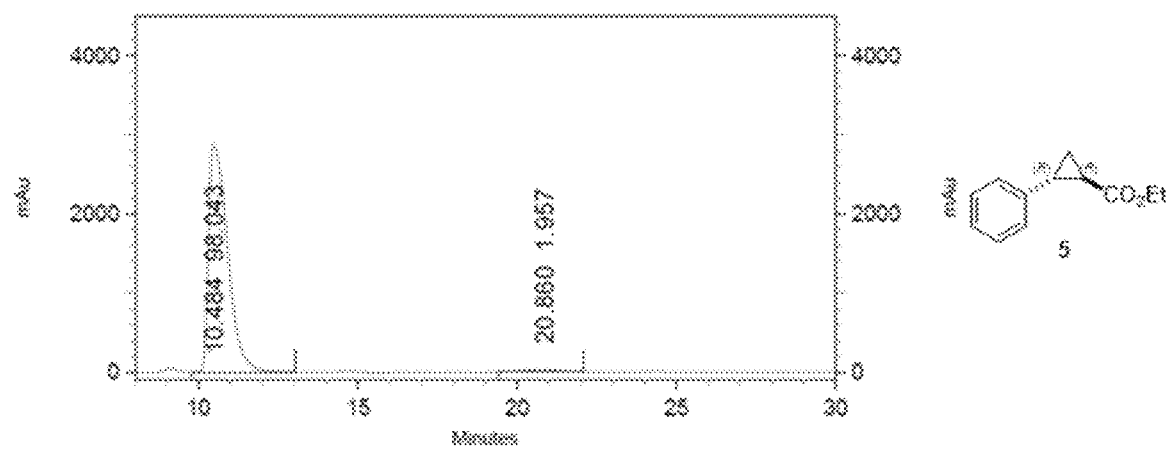
Figure 17B:
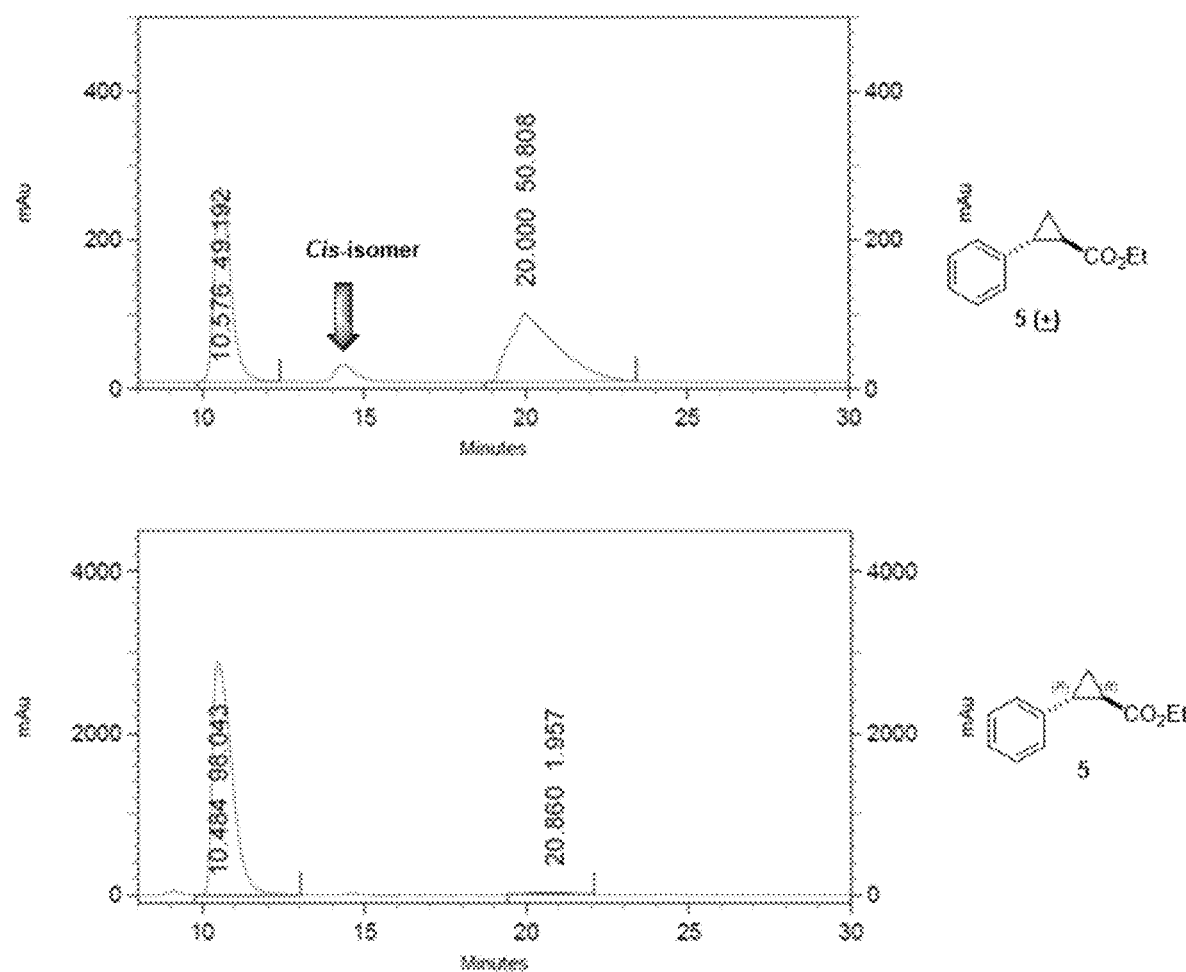
FIG. 17B shows $^1$H NMR characterization of compound 5.
Figure 18A:
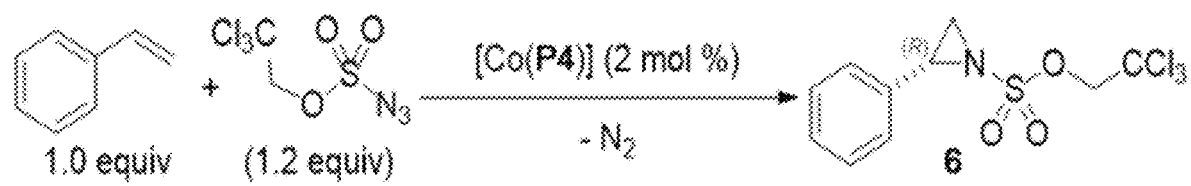
FIG. 18A shows a synthesis scheme and chiral HPLC separation of stereoisomers.
Figure 18A:
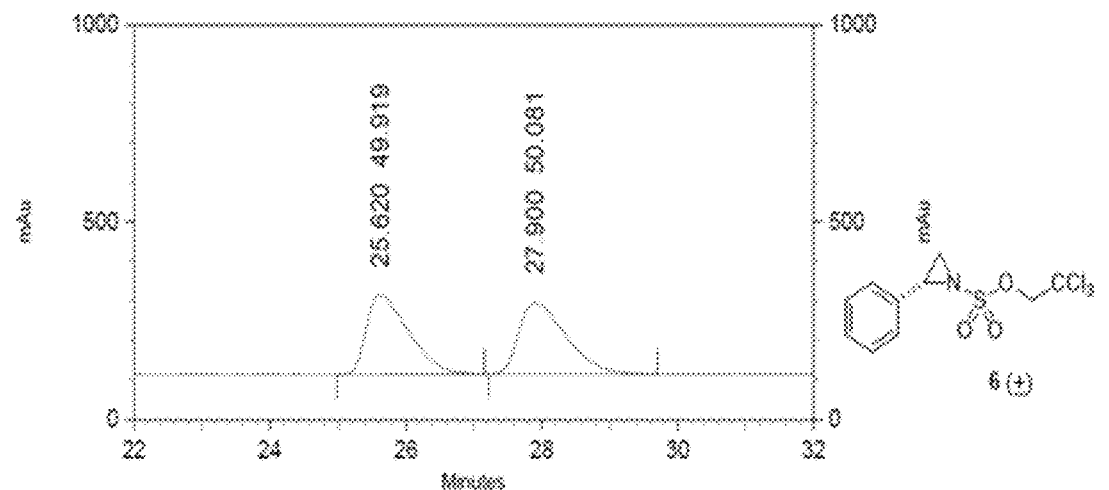
Figure 18A:
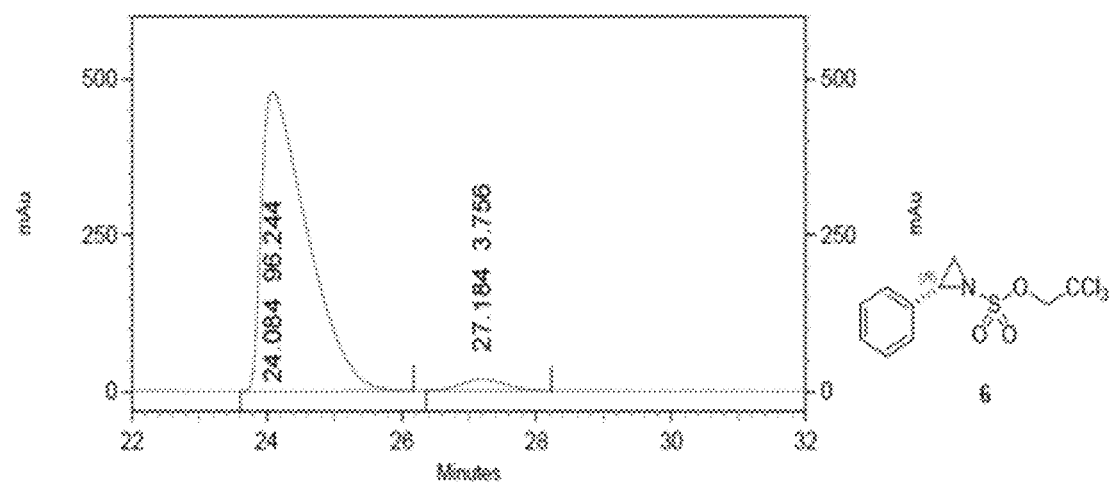
Figure 18B:
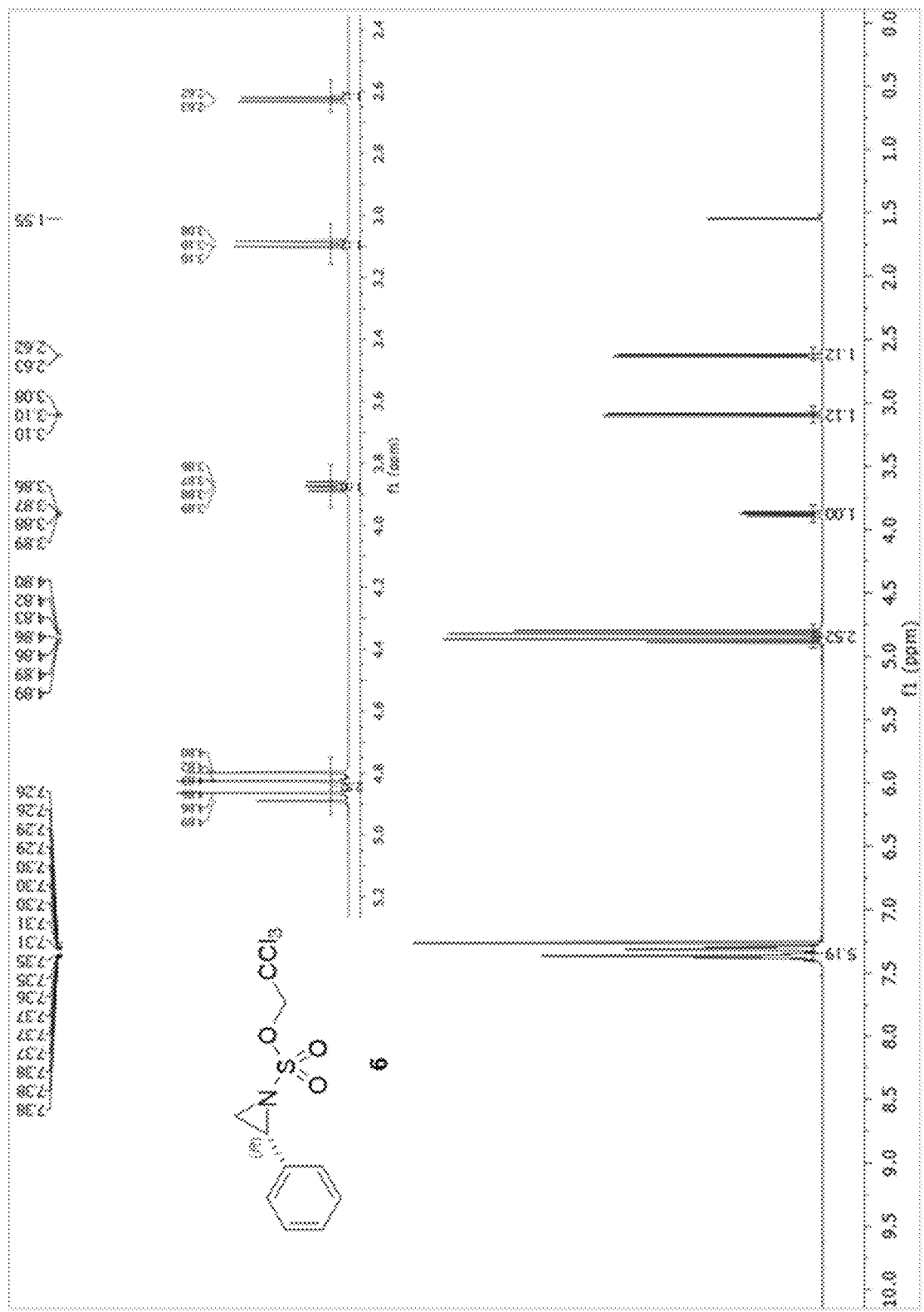
FIG. 18B shows $^1$H NMR characterization of compound 6.

The bridging effect on the catalytic performance of [Co(D$_2$-Por*)] was demonstrated with cyclopropanation and aziridination as two model reactions. The catalytic reactions by bridged catalysts [Co(P3)] and [Co(P4)] were conducted in direct comparison with the open catalysts [Co(P1)] and [Co(P2)] (FIGS. 6A-B). Asymmetric cyclopropanation of styrene with ethyl diazoacetate (EDA) (eq. 1 in FIG. 6A) was carried out at room temperature using 1 mol % catalyst in the absence of additives with the alkene as the limiting reagent without slow addition of the diazo reagent, a practical condition that is atypical for other catalytic systems. Within only 1 h, [Co(P3)] could catalyze the efficient formation of cyclopropane 5 in high yield (93%) with high diastereoselectivity (90% de) and excellent enantioselectivity (96% ee) (see also FIGS. 17A-17B). By comparing the results with [Co(P1)] and [Co(P2)] under the same conditions, it is evident that [Co(P3)] is a superior catalyst for the reaction in terms of both reactivity and stereoselectivity, indicating the positive bridging effect on catalytic performance. While [Co(P4)] could also catalyze the reaction effectively, it differed in both reactivity (84% yield vs 93% yield) and enantioselectivity (88% ee vs 96% ee) from [Co(P3)]. Enantioselective radical aziridination of styrene with trichloroethoxysulfonyl azide (TcesN$_3$) (eq. 2 in FIG. 6B) was carried out at 0° C. for 24 h with 2 mol % catalyst loading in the absence of additives with the alkene as the limiting reagent. While both [Co(P1)] and [Co(P2)] could generate the desired aziridine 6 in high yields, the enantioselectivities were inferior. Under the same conditions, the use of [Co(P3)] resulted in dramatic improvement in enantioselectivity (85% ee) but a considerable decrease in reactivity (24% yield). Switching from [Co(P3)] to [Co(P4)] led to further improvement in enantioselectivity (92% ee) while significantly enhancing reactivity (94% yield) (see also FIGS. 18A-18B). Considering that [Co(P3)] and [Co(P4)] differs only in the length of the distal bridge by merely two methylene units, the observed ligand effect is truly remarkable and may have an important implication in catalyst design and development.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

What is claimed is:

1. A catalyst for the synthesis of chiral cyclopropane derivatives and chiral aziridine derivatives, the catalyst comprising Formula I:

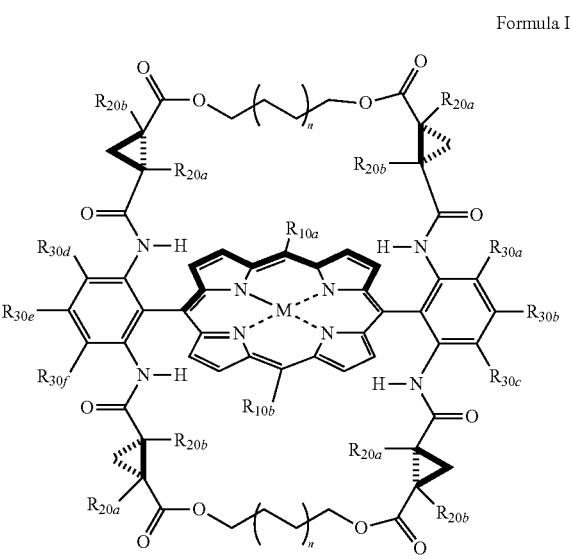

Formula I wherein $R_{10a}$ and $R_{10b}$ are

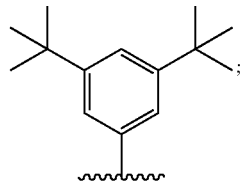

wherein $R_{20a}$ and $R_{20b}$ are hydrogen; wherein each of $R^{30a}$, $R^{30b}$, $R^{30c}$, $R^{30d}$, $R^{30e}$, and $R^{30f}$ are hydrogen; wherein n is 1 or 2; and wherein M is cobalt.

2. The catalyst of claim 1, wherein stereocenters in the catalyst have the (R) configuration.

3. The catalyst of claim 1, wherein n is 1.

4. The catalyst of claim 1, wherein n is 2.

5. A method for the stereoselective synthesis of a chiral cyclopropane derivative, the method comprising contacting a diazo substrate and a vinyl-containing substrate with the catalyst of claim 1 in a solvent and wherein the solvent comprises toluene, chlorobenzene, or a combination thereof.

6. The method of claim 5, wherein the diazo substrate comprises ethyl diazoacetate and wherein the vinyl-containing substrate comprises styrene.

7. The method of claim 5, wherein the chiral cyclopropane derivative comprises a structure of Formula III:

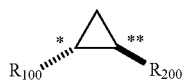

Formula III wherein $R_{100}$ is C1-C10 substituted alkyl, substituted aryl, substituted heteroaryl, substituted cycloalkyl, and substituted heteroalkyl; wherein $R_{200}$ is —(C=O)$R_{40}$; wherein $R_{40}$ is selected from substituted alkyl, substituted aryl, substituted heteroaryl, substituted cycloalkyl, and substituted heteroalkyl, —$NR_{41}R_{42}$, —$OR_{41}$, —$SR_{41}$; and herein each of $R_{41}$ and $R_{42}$ is independently selected from hydrogen, substituted alkyl, substituted aryl, substituted heteroaryl, substituted cycloalkyl, and substituted heteroalkyl.

8. The method of claim 7, wherein the structure of Formula III comprises:

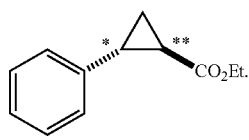 [SMILES: CCOC(=O)[C@@H]1C[C@H]1c1ccccc1]

9. The method of claim 7, wherein the ratio of (R) enantiomer at * to (S) enantiomer at * is from about 5:95 to about 95:5.

10. The method of claim 7, wherein the ratio of (R) enantiomer at  to (S) enantiomer at  is from about 5:95 to about 95:5.

11. The method of claim 7, wherein the chiral cyclopropane derivative comprises a mixture of diastereomers and wherein the mixture of diastereomers comprises at least 80% of a compound having (R) configuration at * and **.

12. A method for the stereoselective synthesis of a chiral aziridine derivative, the method comprising contacting an azido-containing substrate and a vinyl-containing substrate with the catalyst of claim 1 in a solvent and wherein the solvent comprises toluene, chlorobenzene, or a combination thereof.

13. The method of claim 12, wherein the azido-containing substrate comprises trichloroethoxysulfonyl azide and wherein the vinyl-containing substrate comprises styrene.

14. The method of claim 12, wherein the chiral aziridine derivative comprises a structure of Formula IV:

wherein $R_{300}$ is C1-C10 substituted alkyl, substituted aryl, substituted heteroaryl, substituted cycloalkyl, and substituted heteroalkyl; wherein $R_{400}$ is —(C=O)$R_{40}$; wherein $R_{40}$ is selected from substituted alkyl, substituted aryl, substituted heteroaryl, substituted cycloalkyl, and substituted heteroalkyl, —$NR_{41}R_{42}$, —$OR_{41}$, —$SR_{41}$; and herein each of $R_{41}$ and $R_{42}$ is independently selected from hydrogen, substituted alkyl, substituted aryl, substituted heteroaryl, substituted cycloalkyl, and substituted heteroalkyl.

15. The method of claim 14, wherein the structure of Formula IV comprises:

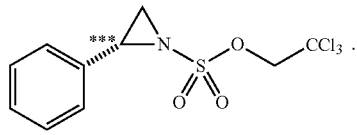

16. The method of claim 14, wherein the ratio of (R) enantiomer at * to (S) enantiomer at* is from about 5:95 to about 95:5.

* * * * *